US010967160B2

(12) United States Patent
Sverdlik et al.

(10) Patent No.: US 10,967,160 B2
(45) Date of Patent: Apr. 6, 2021

(54) TISSUE TREATMENT

(75) Inventors: Ariel Sverdlik, Tel-Aviv (IL); Iris Szwarcfiter, Tel-Aviv (IL); Or Shabtay, Kibbutz Farod (IL)

(73) Assignee: CardioSonic Ltd., Tel-Aviv (IL)

( * ) Notice: Subject to any disclaimer, the term of this patent is extended or adjusted under 35 U.S.C. 154(b) by 0 days.

(21) Appl. No.: 13/449,539

(22) Filed: Apr. 18, 2012

(65) Prior Publication Data

US 2012/0265227 A1    Oct. 18, 2012

Related U.S. Application Data

(63) Continuation-in-part of application No. PCT/IB2011/054640, filed on Oct. 18, 2011.

(Continued)

(51) Int. Cl.
*A61H 1/00* (2006.01)
*A61M 31/00* (2006.01)
(Continued)

(52) U.S. Cl.
CPC .............. *A61M 31/00* (2013.01); *A61B 8/12* (2013.01); *A61B 8/481* (2013.01);
(Continued)

(58) Field of Classification Search
CPC .............. A61N 7/00; A61N 2007/0026; A61N 2007/0039; A61N 2007/0082; A61H 23/0245; A61M 31/00; A61M 25/10; A61M 25/007; A61M 2025/091; A61M 2025/1052; A61B 8/12; A61B 8/481; A61B 17/22012; A61B 2017/320069;
(Continued)

(56) References Cited

U.S. PATENT DOCUMENTS 4,319,580 A    3/1982    Colley et al.
5,038,789 A    8/1991    Frazin
(Continued)

FOREIGN PATENT DOCUMENTS

CN    1279595    1/2001
CN    101610735    12/2009
(Continued)

OTHER PUBLICATIONS

Restriction Official Action dated Aug. 30, 2012 From the US Patent and Trademark Office Re. U.S. Appl. No. 13/049,013.
(Continued)

*Primary Examiner* — Hien N Nguyen

(57) ABSTRACT

There is provided in accordance with an exemplary embodiment of the invention a method of treating a subject suffering from a nerve related disorder, the method comprising causing a damage region to one or both of a lumen wall or nearby surrounding tissues, the damage region encompassing a volume having dimensions of less than about 6.8 mm in a substantially radial direction, less than about 5.8 mm in a direction substantially tangential to the lumen, less than about 10 mm in a substantially axial direction, the damage region being located no closer than about 0.2 mm from an inner wall of the lumen, the damage region comprises of greater than about 60% of collagen denatured tissue.

24 Claims, 39 Drawing Sheets
(15 of 39 Drawing Sheet(s) Filed in Color)

Related U.S. Application Data

(60) Provisional application No. 61/393,947, filed on Oct. 18, 2010, provisional application No. 61/453,239, filed on Mar. 16, 2011.

(51) Int. Cl.

| | |
|---|---|
| *A61B 17/22* | (2006.01) |
| *A61M 25/10* | (2013.01) |
| *A61B 8/12* | (2006.01) |
| *A61B 8/08* | (2006.01) |
| *A61B 17/32* | (2006.01) |
| *A61B 17/00* | (2006.01) |
| *A61M 25/00* | (2006.01) |
| *A61M 25/09* | (2006.01) |
| *A61N 7/00* | (2006.01) |
| *A61F 7/00* | (2006.01) |
| *A61B 6/12* | (2006.01) |
| *A61B 6/00* | (2006.01) |

(52) U.S. Cl.
CPC ....... *A61B 17/22012* (2013.01); *A61M 25/10* (2013.01); *A61B 6/12* (2013.01); *A61B 6/504* (2013.01); *A61B 2017/00106* (2013.01); *A61B 2017/22027* (2013.01); *A61B 2017/320069* (2017.08); *A61F 2007/0063* (2013.01); *A61M 25/007* (2013.01); *A61M 2025/091* (2013.01); *A61M 2025/1052* (2013.01); *A61N 2007/0026* (2013.01); *A61N 2007/0039* (2013.01); *A61N 2007/0082* (2013.01)

(58) Field of Classification Search
CPC . A61B 6/12; A61B 6/504; A61B 2017/00106; A61B 2017/22027; A61F 2007/0063
USPC .......................................................... 601/2
See application file for complete search history.

(56) References Cited

U.S. PATENT DOCUMENTS

| | | | |
|---|---|---|---|
| 5,226,847 A | 7/1993 | Thomas, III et al. |
| 5,421,338 A | 6/1995 | Crowley et al. |
| 5,467,251 A | 11/1995 | Katchmar |
| 5,471,988 A | 12/1995 | Fujio et al. |
| 5,524,630 A | 6/1996 | Crowley |
| 5,590,653 A | 1/1997 | Aida et al. |
| 5,620,417 A | 4/1997 | Jang et al. |
| 5,657,760 A | 8/1997 | Ying et al. |
| 5,699,804 A | 12/1997 | Rattner |
| 5,707,367 A | 1/1998 | Nilsson |
| 5,735,280 A | 4/1998 | Sherman et al. |
| 5,762,066 A | 6/1998 | Law et al. |
| 5,772,642 A | 6/1998 | Ciamacco, Jr. et al. |
| 5,895,355 A | 4/1999 | Schacr |
| 5,895,356 A | 4/1999 | Andrus et al. |
| 5,971,949 A | 10/1999 | Levin et al. |
| 6,007,499 A | 12/1999 | Martin et al. |
| 6,042,556 A | 3/2000 | Beach et al. |
| 6,073,048 A | 6/2000 | Kieval et al. |
| 6,077,225 A | 6/2000 | Brock-Fisher |
| 6,117,101 A | 9/2000 | Diederich et al. |
| 6,119,041 A | 9/2000 | Pomeranz et al. |
| 6,165,127 A | 12/2000 | Crowley |
| 6,210,393 B1 | 4/2001 | Brisken |
| 6,216,041 B1 | 4/2001 | Tierney et al. |
| 6,235,024 B1 | 5/2001 | Tu |
| 6,261,233 B1 | 7/2001 | Kantorovich |
| 6,296,619 B1 | 10/2001 | Brisken et al. |
| 6,379,320 B1 | 4/2002 | Lafon et al. |
| 6,428,477 B1 | 8/2002 | Mason |
| 6,451,013 B1 | 9/2002 | Bays et al. |
| 6,500,121 B1 | 12/2002 | Slayton et al. |
| 6,511,428 B1 | 1/2003 | Azuma et al. |
| 6,511,436 B1 | 1/2003 | Asmar |
| 6,514,249 B1 | 2/2003 | Maguire et al. |
| 6,527,759 B1 | 3/2003 | Tachibana et al. |
| 6,547,788 B1 | 4/2003 | Maguire et al. |
| 6,599,288 B2 | 7/2003 | Maguire et al. |
| 6,607,502 B1 | 8/2003 | Maguire et al. |
| 6,645,147 B1 | 11/2003 | Jackson et al. |
| 6,740,040 B1 | 5/2004 | Mandrusov et al. |
| 6,752,805 B2 | 6/2004 | Maguire et al. |
| 6,953,460 B2 | 10/2005 | Maguire et al. |
| 6,955,173 B2 | 10/2005 | Lesh |
| 6,978,174 B2 | 12/2005 | Gelfand et al. |
| 7,001,336 B2 | 2/2006 | Mandrusov et al. |
| 7,037,271 B2 | 5/2006 | Crowley |
| 7,084,004 B2 | 8/2006 | Vaiyapuri et al. |
| 7,156,816 B2 | 1/2007 | Schwartz et al. |
| 7,162,303 B2 | 1/2007 | Levin et al. |
| 7,166,098 B1 | 1/2007 | Steward et al. |
| 7,220,233 B2 | 5/2007 | Nita et al. |
| 7,220,258 B2 | 5/2007 | Myhr |
| 7,220,261 B2 | 5/2007 | Truckai et al. |
| 7,285,116 B2 | 10/2007 | De la Rama et al. |
| 7,326,201 B2 | 2/2008 | Fjield et al. |
| 7,341,583 B2 | 3/2008 | Shiono et al. |
| 7,344,529 B2 | 3/2008 | Torchia et al. |
| 7,347,859 B2 | 3/2008 | Garabedian et al. |
| 7,410,486 B2 | 8/2008 | Fuimaono et al. |
| 7,460,369 B1 | 12/2008 | Blish, II |
| 7,470,241 B2 | 12/2008 | Weng et al. |
| 7,479,106 B2 | 1/2009 | Banik et al. |
| 7,510,536 B2 | 3/2009 | Foley et al. |
| 7,538,425 B2 | 5/2009 | Myers et al. |
| RE40,815 E | 6/2009 | Kudaravalli et al. |
| 7,540,846 B2 | 6/2009 | Harhen et al. |
| 7,540,870 B2 | 6/2009 | Babaev |
| 7,563,260 B2 | 7/2009 | Whitmore et al. |
| 7,617,005 B2 | 11/2009 | Demarais et al. |
| 7,620,451 B2 | 11/2009 | Demarais et al. |
| 7,621,929 B2 | 11/2009 | Nita et al. |
| 7,647,115 B2 | 1/2010 | Levin et al. |
| 7,653,438 B2 | 1/2010 | Deem et al. |
| 7,655,005 B2 | 2/2010 | Bhola |
| 7,678,104 B2 | 3/2010 | Keidar |
| 7,704,212 B2 | 4/2010 | Wekell et al. |
| 7,713,210 B2 | 5/2010 | Byrd et al. |
| 7,717,948 B2 | 5/2010 | Demarais et al. |
| 7,727,228 B2 | 6/2010 | Abboud et al. |
| 7,736,317 B2 | 6/2010 | Stephens et al. |
| 7,756,583 B2 | 7/2010 | Demarais et al. |
| 7,762,954 B2 | 7/2010 | Nix et al. |
| 7,771,372 B2 | 8/2010 | Wilson |
| 7,819,868 B2 | 10/2010 | Cao et al. |
| 7,824,348 B2 | 11/2010 | Barthe et al. |
| 7,850,683 B2 | 12/2010 | Elkins et al. |
| 7,850,685 B2 | 12/2010 | Kunis et al. |
| 7,853,333 B2 | 12/2010 | Demarais |
| 7,854,733 B2 | 12/2010 | Govari |
| 7,883,506 B2 | 2/2011 | McIntyre et al. |
| 7,940,969 B2 | 5/2011 | Nair et al. |
| 8,216,216 B2 | 7/2012 | Warnking et al. |
| 8,221,402 B2 | 7/2012 | Francischelli et al. |
| 8,401,667 B2 | 3/2013 | Gustus et al. |
| 8,419,729 B2 | 4/2013 | Ibrahim et al. |
| 8,540,662 B2 | 9/2013 | Stehr et al. |
| 8,568,403 B2 | 10/2013 | Soltesz et al. |
| 8,585,695 B2 | 11/2013 | Shih |
| 8,974,446 B2 | 3/2015 | Nguyen et al. |
| 2001/0014780 A1 | 8/2001 | Martin et al. |
| 2001/0053885 A1 | 12/2001 | Gielen et al. |
| 2002/0002371 A1 | 1/2002 | Acker et al. |
| 2002/0019627 A1 | 2/2002 | Maguire et al. |
| 2002/0022833 A1 | 2/2002 | Maguire et al. |
| 2002/0026127 A1* | 2/2002 | Balbierz et al. .............. 600/567 |
| 2002/0048310 A1 | 4/2002 | Heuser |
| 2002/0055754 A1 | 5/2002 | Ranucci et al. |
| 2002/0065512 A1 | 5/2002 | Fjield et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |

(56) References Cited

U.S. PATENT DOCUMENTS

| | | |
|---|---|---|
| 2003/0013968 A1 | 1/2003 | Fjield et al. |
| 2003/0092667 A1 | 5/2003 | Tachibana et al. |
| 2003/0125726 A1 | 7/2003 | Maguire et al. |
| 2003/0151417 A1 | 8/2003 | Koen |
| 2003/0181901 A1 | 9/2003 | Maguire et al. |
| 2003/0195496 A1 | 10/2003 | Maguire et al. |
| 2003/0199747 A1 | 10/2003 | Michlitsch et al. |
| 2003/0199768 A1 | 10/2003 | Cespededs et al. |
| 2004/0006333 A1 | 1/2004 | Arnold et al. |
| 2004/0082859 A1 | 4/2004 | Schaer |
| 2004/0102361 A1 | 5/2004 | Bodin |
| 2004/0102769 A1 | 5/2004 | Schwartz et al. |
| 2005/0015079 A1 | 1/2005 | Keider |
| 2005/0020967 A1 | 1/2005 | Ono |
| 2005/0096542 A1 | 5/2005 | Weng |
| 2005/0096647 A1 | 5/2005 | Steinke et al. |
| 2005/0215946 A1 | 9/2005 | Hansmann et al. |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |
| 2006/0079816 A1 | 4/2006 | Barthe et al. |
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |
| 2006/0264809 A1 | 11/2006 | Hansmann et al. |
| 2007/0043297 A1 | 2/2007 | Miyazawa |
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0203479 A1 | 8/2007 | Auth et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0249997 A1 | 10/2007 | Goodson, IV et al. |
| 2007/0282407 A1 | 12/2007 | Demarais et al. |
| 2008/0039745 A1 | 2/2008 | Babev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0125829 A1 | 5/2008 | Velasco et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0214966 A1 | 9/2008 | Slayton et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1 | 4/2010 | Sverdlik et al. |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0168649 A1 | 7/2010 | Schwartz et al. |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1 | 9/2010 | Sliwa et al. |
| 2010/0331686 A1 | 12/2010 | Hossack et al. |
| 2010/0331950 A1 | 12/2010 | Strommer |
| 2011/0009779 A1 | 1/2011 | Romano et al. |
| 2011/0028962 A1 | 2/2011 | Werneth et al. |
| 2011/0034809 A1 | 2/2011 | Eberle et al. |
| 2011/0066217 A1 | 3/2011 | Diller et al. |
| 2011/0092781 A1* | 4/2011 | Gertner ................ 600/301 |
| 2011/0092880 A1 | 4/2011 | Gertner |
| 2011/0112400 A1 | 5/2011 | Emery et al. |
| 2011/0178441 A1* | 7/2011 | Tyler ................ 601/2 |
| 2011/0201973 A1 | 8/2011 | Stephens et al. |
| 2011/0257563 A1 | 10/2011 | Thapliyal et al. |
| 2011/0264086 A1 | 10/2011 | Ingle |
| 2011/0270247 A1 | 11/2011 | Sherman |
| 2011/0282249 A1 | 11/2011 | Tsoref et al. |
| 2011/0319765 A1 | 12/2011 | Gertner et al. |
| 2012/0016273 A1 | 1/2012 | Diederich |
| 2012/0053577 A1 | 3/2012 | Lee et al. |
| 2012/0065494 A1 | 3/2012 | Gertner et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0123270 A1 | 5/2012 | Klee et al. |
| 2012/0209116 A1 | 8/2012 | Hossack et al. |
| 2012/0215106 A1 | 8/2012 | Sverdlik et al. |
| 2012/0232409 A1 | 9/2012 | Stahmann et al. |
| 2012/0232436 A1 | 9/2012 | Warnking |
| 2012/0268886 A1 | 10/2012 | Leontiev et al. |
| 2012/0283605 A1 | 11/2012 | Lewis, Jr. |
| 2012/0310233 A1* | 12/2012 | Dimmer et al. ........ 606/33 |
| 2012/0316559 A1 | 12/2012 | Mayse et al. |
| 2013/0072928 A1 | 3/2013 | Schaer |
| 2013/0131668 A1 | 5/2013 | Schaer |
| 2013/0197555 A1 | 8/2013 | Schaer |
| 2013/0204167 A1 | 8/2013 | Sverdlik et al. |
| 2013/0204242 A1 | 8/2013 | Sverdlik et al. |
| 2013/0207519 A1 | 8/2013 | Chaggares et al. |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0225595 A1 | 8/2013 | Gillies et al. |
| 2013/0267875 A1 | 10/2013 | Thapliyal et al. |
| 2013/0296836 A1 | 11/2013 | Barbut et al. |
| 2013/0310822 A1 | 11/2013 | Mayse et al. |
| 2014/0012133 A1 | 1/2014 | Sverdlik et al. |
| 2014/0039286 A1 | 2/2014 | Hoffer |
| 2014/0039477 A1 | 2/2014 | Sverdlik et al. |
| 2014/0074076 A1 | 3/2014 | Gertner |
| 2014/0088585 A1 | 3/2014 | Hill et al. |
| 2014/0180197 A1 | 6/2014 | Sverdlik et al. |
| 2014/0180277 A1 | 6/2014 | Chen |
| 2014/0194866 A1 | 7/2014 | Wang |
| 2014/0276135 A1 | 9/2014 | Agah et al. |
| 2015/0057599 A1 | 2/2015 | Chen |
| 2015/0073400 A1 | 3/2015 | Sverdlik et al. |
| 2015/0272668 A1 | 10/2015 | Chen |
| 2016/0059044 A1 | 3/2016 | Gertner |
| 2016/0113699 A1 | 4/2016 | Sverdlik et al. |
| 2016/0374710 A1 | 12/2016 | Sinelnikov et al. |
| 2017/0027645 A1 | 2/2017 | Ben Oren et al. |
| 2018/0326227 A1 | 11/2018 | Sverdlik et al. |

FOREIGN PATENT DOCUMENTS

| | | |
|---|---|---|
| CN | 101820820 | 9/2010 |
| EP | 1424100 | 6/2004 |
| EP | 1799302 | 3/2006 |

(56) References Cited

FOREIGN PATENT DOCUMENTS

| | | |
|---|---|---|
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| JP | 07-227394 | 8/1995 |
| JP | 09-122139 | 5/1997 |
| JP | 10-248854 | 9/1998 |
| JP | 2008-536562 | 9/2008 |
| JP | 2010-517695 | 5/2010 |
| WO | WO 91/10405 | 7/1991 |
| WO | WO 99/16366 | 4/1999 |
| WO | WO 00/67648 | 10/2000 |
| WO | WO 01/45550 | 6/2001 |
| WO | WO 2004/054448 | 7/2004 |
| WO | WO 06/022790 | 3/2006 |
| WO | WO 06/041881 | 4/2006 |
| WO | WO 2006/041847 | 4/2006 |
| WO | WO 2006/042163 | 4/2006 |
| WO | WO 2007/001981 | 1/2007 |
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/098101 | 8/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO 2012/061713 | 5/2012 |
| WO | WO 2013/030743 | 3/2013 |
| WO | WO 2013/111136 | 8/2013 |
| WO | WO 2013/134479 | 9/2013 |
| WO | WO 2013/157009 | 10/2013 |
| WO | WO 2013/157011 | 10/2013 |
| WO | WO 2013/162694 | 10/2013 |
| WO | WO 2014/188430 | 11/2014 |
| WO | WO 2016/084081 | 6/2016 |
| WO | WO 2018/173052 | 9/2018 |
| WO | WO 2018/173053 | 9/2018 |

OTHER PUBLICATIONS

Restriction Official Action dated Oct. 5, 2012 From the US Patent and Trademark Office Re. U.S. Appl. No. 13/049,151.
International Search Report and the Written Opinion dated Jun. 22, 2012 From the International Searching Authority Re. Application No. PCT/IB2011/054640.
Official Action dated Jan. 29, 2013 From the US Patent and Trademark Office Re. U.S. Appl. No. 13/049,151.
Ahmed et al. "Renal Sympathetic Denervation Using an Irrigated Radiofrequency Ablation Catheter for the Management of Drug-Resistant Hypertension", Journal of the American College of Cardiology: Cardiovascular Interventions, JACC, 5(7): 758-765, 2012.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.
Brinton et al. "Externally Focused Ultrasound for Sympathetic Renal Denervation", WAVE I First-In-Man Study, Kona Medical Inc., PowerPont Presentation, TCT 2012, 15 P., 2012.

Davies et al. "First-in-Man Safety Evaluation of Renal Denervation for Chronic Systolic Heart Failure: Primary Outcome From REACH-Pilot Study", International Journal of Cardiology, 162: 189-192, 2013.
Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.
Fischell PeriVascular Renal Denervation (PVRD™) Ablative Solutions Inc., TransCatheter Therapeutics Meeting, Miami, FL, USA, Oct. 24, 2012, PowerPoint Presentation, 14 P., Oct. 2012.
Goswami "Renal Denervation: A Percutaneous Therapy for HTN", Prairie Heart Institute, Synvacor, The VEINS: Venous Endovascular Interventions Strategies, Chicago, USA, 42 P., 2012.
Hering et al. "Renal Denervation in Moderate to Severe CKD", Journal of the American Society of Nephrology, 23: 1250-1257, 2012.
Hering et al. "Substantial Reduction in Single Sympathetic Nerve Firing After Renal Denervation in Patients With rRsistant Hypertension", Hypertension, 61: 1-14, Nov. 19, 2012.
Joner "Histopathological Characterization of Renal Arteries After Radiofrequency Catheter Based Sympathetic Denervation in a Healthy Porcine Model", Deutsches Herzzentrum M?nchen, Technische Universit?t M?nchen, PowerPoint Presentation, TCT 2012, 15 P., 2012.
Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.
Lambert et al. "Redo of Percutaneous Renal Denervation in a Patient With Recurrent Resistant Hypertension After Primary Treatment Success", Catheterization and Cardiovascular Interventions, p. 1-11, 2012.
Mabin et al. "First Experience With Endovascular Ultrasound Renal Denervation for the Treatment of Resistant Hypertension", EuroIntervention, 8: 57-61, 2012.
Mahfoud et al. "Effect of Renal Sympathetic Denervation on Glucose Metabolism in Patients With Resistant Hypertension: A Pilot Study", Circulation, 123: 1940-1946, 2011.
Mahfoud et al. "Renal Hemodynamics and Renal Function After Catheter-Based Renal Sympathetic Denervation in Patients With Resistant Hypertension", Hypertension, 60: 419-424, 2012.
Mazor "Efficacy of Renal Denervation Is Positively Impacted by Longitudinal Treatments", Vessix Vascular Inc., PowerPoint Presentation, TCT 2012, 20 P., 2012.
Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.
Ong et al. "Successful Treatment of Resistant Hypertension With Percutaneous Renal Denervation Therapy", Heart, 98(23): 1754-1755, Dec. 2012.
Ormiston "One Shot (Covidien)", Maya Medical, Auckland, New Zealand, PowerPoint Presentation.
Ormiston et al. "First-in-Human Use of the OneShot™ Renal Denervation System From Covidien", EuroIntervention, 8: 1090-1094, 2013.
Page et al. "The Effect of Renal Denervation on Patients Suffering From Nephritis", The Journal of Clinical Investigation, 14(4): 443-458, Jul. 1935.
Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.
Prochnau et al. "Catheter-Based Renal Denervation for Drug-Resistant Hypertension by Using a Standard Electrophysiology Catheter", EuroIntervention, 7: 1077-1080, 2012.
Prochnau et al. "Efficacy of Renal Denervation With a Standard EP Catheter in the 24-h Ambulatory Blood Pressure Monitoring—Long-Term Follow-Up", International Journal of Cardiology, 157(3): 447-448, Jun. 14, 2012.

(56) References Cited

OTHER PUBLICATIONS

Rothman "FIM Evaluation of a New, Multi-Electrode RF System for Renal Denervation (Medtronic)", Medtronic Inc., PowerPoint Presentation, 8 P., 2012.
Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.
Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.
Scheinert "Cardiosonic TIVUS™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.
Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.
Sievert et al. "Catheter-Based Technology Alternatives for Renal Denervation", CardioVascular Center Frankfurt, Germany, TCT 2012, Miami, FL, USA, Oct. 22-26, 2012, PowerPoint Presentation, 35 P., Oct. 2012.
Stefanadis "Vincristine Local Delivery for Renal Artery Denervation", Athens, Greece, PowerPoint Presentation, TCT 2012, 21 P., 2012.
Steigerwald et al. "Morphological Assessment of Renal Arteries After Radiofrequency Catheter-Based Sympathetic Denervation in a Porcine Model", Journal of Hypertension, 30(11): 2230-2239, Nov. 2012.
Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.
Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.
Virmani "Translation Medicine and Renal Denervation: Pre-Clinical Animal Models and Histoanatomy", CVPath Institute, Gaithersburg, MD, USA, PowerPoint Presentation.
Voskuil et al. "Percutaneous Renal Denervation for the Treatment of Resistant Essential Hypertension; The First Dutch Experience", Netherlands Heart Journal, 19(7-8): 319-323, Aug. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
International Preliminary Report on Patentability dated May 2, 2013 From the International Bureau of WIPO Re. Application No. PCT/IB2011/054634.
International Preliminary Report on Patentability dated May 2, 2013 From the International Bureau of WIPO Re. Application No. PCT/IB2011/054635.
International Preliminary Report on Patentability dated May 2, 2013 From the International Bureau of WIPO Re. Application No. PCT/IB2011/054636.
International Preliminary Report on Patentability dated May 2, 2013 From the International Bureau of WIPO Re. Application No. PCT/IB2011/054638.
International Preliminary Report on Patentability dated May 2, 2013 From the International Bureau of WIPO Re. Application No. PCT/IB2011/054639.
International Preliminary Report on Patentability dated May 2, 2013 From the International Bureau of WIPO Re. Application No. PCT/IB2011/054640.
International Preliminary Report on Patentability dated May 2, 2013 From the International Bureau of WIPO Re. Application No. PCT/IB2011/054641.
Schwartz "Strategies to Model Efficacy of Hypertension Devices", EuroPCR 2013, The Leading Cardiovascular Course, 24 P., 2013.
Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.
Notice of Allowance dated Jun. 21, 2013 From the US Patent and Trademark Office Re. U.S. Appl. No. 13/049,151.
Invitation to Pay Additional Fees dated Jul. 24, 2013 From the International Searching Authority Re. Application No. PCT/IL2013/050068.
Official Action dated Jul. 17, 2013 From the US Patent and Trademark Office Re. U.S. Appl. No. 13/049,013.
Official Action dated May 8, 2013 From the US Patent and Trademark Office Re. U.S. Appl. No. 13/462,956.
Failla et al. "Sympathetic Tone Restrains Arterial Distensibility of Healthy and Atherosclerotic Subjects", Journal of Hypertension, 17: 1117-1123, 1999.
Grassi et al. "Sympathetic Mechanisms, Organ Damage, and Antihypertensive Treatment", Current Hypertension Report, 13: 303-308, 2011.
Kleinlogel et al. "A Gene-Fusion Strategy for Stoichiometric and Co-Localized Expression of Light-Gated Membrane Proteins", Nature Methods, 8(12): 1083-1091, Dec. 2011.
Lopez et al. "Effects of Sympathetic Nerves on Collateral Vessels in the Limb of Atherosclerosis Primates", Atherosclerosis, 90: 183-188, 1991.
Mangoni et al. "Effect of Sympathectomy on Mechanical Properties of Common Carotid and Femoral Arteries", Hypertension, 30: 1085-1088, 1997.
Olafsson et al. "Ultrasound Current Source Density Imaging", IEEE Transactions on Biomedical Engineering, 55(7): 1840-1848, Jul. 2008.
Swierblewska et al. "An Independent Relationship Between Muscle Sympathetic Nerve Activity and Pulse Wave Velocity in Normal Humans", Journal of Hypertension, 28: 979-984, 2010.
Wikswo Jr. et al. "Magnetic Field of a Nerve Impulse: First Measurements", Science, 208: 53-55, Apr. 4, 1980.
Witte et al. "Imaging Current Flow in Lobster Nerve Cord Using the Acoustoelectric Effect", Applied Physics Letters, 90: 163902-1-163902-3, 2007.
Official Action dated Oct. 24, 2012 From the US Patent and Trademark Office Re. U.S. Appl. No. 13/049,013.
International Search Report and the Written Opinion dated Oct. 29, 2013 From the International Searching Authority Re. Application No. PCT/IL2013/050339.
Notice of Allowance dated Nov. 7, 2013 From the US Patent and Trademark Office Re. U.S. Appl. No. 13/049,013.
International Search Report and the Written Opinion dated Feb. 7, 2012 From the International Searching Authority Re. Application No. PCT/IB2011/054641.
International Search Report and the Written Opinion dated Jan. 23, 2012 From the International Searching Authority Re. Application No. PCT/IB2011/054635.
International Search Report and the Written Opinion dated Jan. 25, 2012 From the International Searching Authority Re. Application No. PCT/IB2011/054636.
International Search Report and the Written Opinion dated Jan. 27, 2012 From the International Searching Authority Re. Application No. PCT/IB2011/054634.
International Search Report and the Written Opinion dated Jan. 27, 2012 From the International Searching Authority Re. Application No. PCT/IB2011/054638.
International Search Report and the Written Opinion dated Jan. 31, 2012 From the International Searching Authority Re. Application No. PCT/IB2011/054639.
Invitation to Pay Additional Fees dated Apr. 17, 2012 From the International Searching Authority Re. Application No. PCT/IB2011/054640.

(56) References Cited

OTHER PUBLICATIONS

Anonymus "Indication for and Results of Sympathectomy in Patients With Peripheral Vascular Disease", Lumbar Sympathectomy, Poster, 34 P., 2009.
Aoyama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h col., p. 1249, r-h col.
Baker et al. "Operative Lumbar Sympathectomy for Severe Lower Limb Ischaemia: Still a Valuable Treatment Option", Annals of the Royal College of Surgeons of England, 76(1): 50-53, Jan. 1994.
Bharat et al. "Monitoring Stiffness Changes in Lesions After Radiofrequency Ablation at Different Temperatures and Durations of Ablation", Ultrasound in Medicine & Biology, 31(3): 415-422, 2005.
Blankestijn et al. "Renal Denervation: Potential Impact on Hypertension in Kidney Disease?", Nephrology, Dialysis, Transplantation, 26(9): 2732-2734, Apr. 19, 2011.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.
Campese et al. "Sympathetic Renal Innervation and Resistant Hypertension", International Journal of Hypertension, 2011(Art.ID 814354): 1-6, 2011.
Copty et al. "Localized Heating of Biological Media Using a 1-W Microwave Near-Field Probe", IEEE Transactions on Microwave Theory and Techniques, 52(8): 1957-1963, Aug. 2004.
Copty et al. "Low-Power Near-Field Microwave Applicator for Localized Heating of Soft Matter", Applied Physics Letters, 84(25): 5109-5111, Jun. 21, 2004.
Damianou et al. "Dependence of Ultrasonic Attenuation and Absorpteion in Dog Soft Tissues on Temperature and Thermal Dose", Journal of the Acoustical Society of America, 102(1): 628-634, Jul. 1997.
Deneke et al. "Histopathology of Intraoperatively Induced Linear Radiofrequency Ablation Lesions in Patients With Chronic Atrial Fibrillation", European Heart Journal, 26: 1797-1803, 2005.
DiBona "Neural Control of Renal Function: Cardiovascular Implications", Hypertension, 13: 539-548, 1989.
DiBona "Neural Control of the Kidney: Past, Present, and Future", Hypertension, 41: 621-624, Dec. 16, 2002.
DiBona "Physiology in Perspective: The Wisdom of the Body. Neural Control of the Kidney", American Journal of Physiology, Regulatory, Integrative and Comparative Physiology, 289(3): R633-R641, Sep. 2005.
DiBona et al. "Differentiated Sympathetic Neural Control of the Kidney", American Journal of Physiology, 271: R84-R90, 1996.
DiBona et al. "Translational Medicine: The Antihypertensive Effect of Renal Denervation", American Journal of Physiology, Regulatory, Integrative and Comparative Physiology, 298(2): R245-R253, Feb. 2010.
Diederich et al. "Induction of Hyperthermia Using an Intracavitary Multielement Ultrasonic Applicator", IEEE Transactions on Biomedical Engineering, 36(4): 432-438, Apr. 1989.
Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.

Fort Wayne Metals "HHS Tube", Fort Wayne Metals Research Products Corporation, 2 P., 2009.
Fujikura et al. "Effects of Ultrasonic Exposure Parameters on Myocardial Lesions Induced by High-Intensity Focused Ultrasound", Journal of Ultrasound Medicine, 25: 1375-1386, 2006.
Glazier et al. "Laser Balloon Angioplasty Combined With Local Intrcoronary Heparin Therapy: Immediate and Short-Term Follow-Up Results", American Heart Journal, 134: 266-273, 1997.
Granada et al. "A Translational Overview for the Evaluation of Peri-Renal Denervation Technologies", Cardiovascular Research Foundation, Columbai University Medical Center, New York, USA, Alizee Pathology, 25 P., 2011.
Griffiths et al. "Thoraco-Lumbar Splanchnicectomy and Sympathectomy. Anaesthetic Procedure", Anaesthesia, 3(4): 134-146, Oct. 1948.
Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.
Janssen et al. "Role of Afferent Renal Nerves in Spontaneous Hypertension in Rats", Hypertension, 13: 327-333, 1989.
Katholi "Renal Nerves in the Pathogenesis of Hypertension in Experimental Animals and Humans", American Journal of Physiology, 245: F1-F14, 1983.
Katholi et al. "Intrarenal Adenosine Produces Hypertension by Activating the Sympathetic Nervous System Via the Renal Nerves in the Dog", Journal of Hypertension, 2: 349-359, 1984.
Katholi et al. "Renal Nerves in the Maintenance of Hypertension: A Potential Therapeutic Target", Current Hypertension Reports, 12(3): 196-204, Jun. 2010.
Kline et al. "Functional Reinnervation and Development of Supersensitivity to NE After Renal Denervation in Rats", American Journal of Physiology, 238: R353-R358, 1980.
Kolh "Carotid Denervation by Adventitial Stripping: A Promising Treatment of Carotid Sinus Syndrome?", European Journal of Vascular and Endovascular Surgery, 39(2): 153-154, Feb. 2010.
Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.
Lele "Effects of Focused Ultrasonic Radiation on Peripheral Nerve, With Observations on Local Heating", Experimental Neurology, 8: 47-83, 1963.
Lemoine et al. "Amputations and Sympathectomy in Peripheral Vascular Disease of the Lower Extremity. Experience With 180 Patients", Journal of the National Medical Association, 61(3): 219-221, May 1969.
Li et al. "Acoustic Proximity Ranging in the Presence of Secondary Echoes", IEEE Transactions on Instrumentation and Measurement, XP011102759, 52(5): 1593-1605, Oct. 1, 2003. p. 1593.
Liu et al. "A Helical Microwave Antenna for Welding Plaque During Balloon Angioplasty", IEEE Transactions on Microwave Theory and Techniques, 44(10): 1819-1831, Oct. 1996.
Mahfoud et al. "Is There a Role for Renal Sympathetic Denervation in the Future Treatment of Resistant Hypertension?", Future Cardiology, 7(5): 591-594, 2011.
Makris et al. "Resistant Hypertension Workup and Approach to Treatment", International Journal of Hypertension, 2011(Art. ID598694): 1-10, 2011.
Manasse et al. "Clinical Histopathology and Ultrstructural Analysis of Myocardium Following Microwave Energy Ablation", European Journal of Cardio-Thoracic Surgery, 23: 573-577, 2003.
Martin et al. "Premise, Promise, and Potential Limitations of Invasive Devices to Treat Hypertension", Current Cardiology Reports, 13(1): 86-92, Feb. 2011.
Mogil et al. "Renal Innervation and Renin Activity in Salt Metabolism and Hypertension", American Journal of Physiology, 216(4): 693-697, Apr. 1969.
Ohkubo et al. "Histological Findings After Angioplasty Using Conventional Balloon, Radiofrequency Thermal Balloon, and Stent for Experimental Aortic Coarctation", Pediatrics International, 46: 39-47, 2004.

(56) References Cited

OTHER PUBLICATIONS

Papademetriou et al. "Renal Sympathetic Denervation for the Treatment of Difficult-to-Control or Resistant Hypertension", International Journal of Hypertension, 2011(Art.ID196518): 1-8, Jan. 2011.
Para Tech Coating "Parylene Properties", Para Tech Coating Inc., 1 P.
Quinn "Pre-Eclampsia and Partial Uterine Denervation", Medical Hypotheses, 64(3): 449-454, 2005. Abstract.
Rappaport "Treating Cardiac Disease With Catheter-Based Tissue Heating", IEEE Microwave Magazine, p. 57-64, Mar. 2002.
Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.
Sanni et al. "Is Sympathectomy of Benefit in Critical Leg Ischaemia Not Amenable to Revascularisation?", Interactive CardioVascular and Thoracic Surgery, 4: 478-483, 2005.
Schlaich et al. "Renal Sympathetic-Nerve Ablation for Uncontrolled Hypertension", New England Journal of Medicine, 361(9): 932-934, Aug. 27, 2009.
Souchon et al. "Monitoring the Formation of Thermal Lesions With Heat-Induced Echo-Strain Imaging: A Feasibility Study", Ultrasound in Medicine & Biology, 31(2): 251-259, 2005.
Szabo "Diagnostic Ultrasound Imaging: Inside Out", Academic Press Series in Biomedical Engineering, 2004. Book: Diagnostic Ultrasound Imaging Inside Out—Bronzino ; Academic Press Series in Biomedical Engineering ,Joseph Bronzino, Series Editor ; Trinity College—Hartford, Connecticut "Diagnostic Ultrasound Imaging Inside Out", Academic Press Series in Biomedical Engineering, 2004.
Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.
Toorop et al. "Clinical Results of Carotid Denervation by Adventitial Stripping in Caotid Sinus Syndrome", Europan Journal of Vascular and Endovascular Syndrome, 39: 146-152, 2010.
Tyreus et al. "Two-Dimensional Acoustic Attenuation Mapping of High-Temperature Interstitial Ultrasound Lesions", Physics in Medicine and Biology, 49: 533-546, 2004.
Warwick et al. "Trackless Lesions in Nervous Tissues Produced by High Intensity Focused Ultrsound (High-Frequency Mechanical Waves)", Journal of Anatomy, 102(3): 387-405, 1968.
Wilcox "Resistant Hypertension and the Role of the Sympathetic Nervous System", Medtronic, 30 P.
Williams et al. "Laser Energy Source in Surgical Atrial Fibrillation Ablation: Preclinical Experience", The Annals of Thoracic Surgery, 82: 2260-2264, 2006.
Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.
Xu et al. "Experimental Nerve Thermal Injury", Brain, 117. 375-384, 1994.
Invitation to Pay Additional Fees dated Sep. 3, 2013 From the International Searching Authority Re. Application No. PCT/IL2013/050339.
International Search Report and the Written Opinion dated Sep. 19, 2013 From the International Searching Authority Re. Application No. PCT/IL2013/050068.
Official Action dated Sep. 25, 2013 From the US Patent and Trademark Office Re. U.S. Appl. No. 13/462,956.
Lin et al. "Utility of the PlasmaKinetic™ Bipolar Forceps® for Control of the Renal Artery in a Porcine Model", JTUA, 14(3): 118-121, Sep. 2003.
Invitation to Pay Additional Fees dated Aug. 5, 2013 From the International Searching Authority Re. Application No. PCT/IL2013/050341.
Official Action dated Dec. 19, 2013 From the US Patent and Trademark Office Re. U.S. Appl. No. 13/049,022.
International Search Report and the Written Opinion dated Oct. 11, 2013 From the International Searching Authority Re. Application No. PCT/IL2013/050341.
Communication Pursuant to Article 94(3) EPC dated Nov. 4, 2014 From the European Patent Office Re. Application No. 11833950.6.
Communication Pursuant to Article 94(3) EPC dated Jun. 10, 2014 From the European Patent Office Re. Application No. 117822476.3.
Communication Pursuant to Article 94(3) EPC dated Jun. 10, 2014 From the European Patent Office Re. Application No. 11784782.2.
Communication Pursuant to Article 94(3) EPC dated Apr. 14, 2014 From the European Patent Office Re. Application No. 11782221.3.
Communication Pursuant to Article 94(3) EPC dated Sep. 26, 2014 From the European Patent Office Re. Application No. 11782222.1.
Communication Pursuant to Article 94(3) EPC dated Oct. 30, 2014 From the European Patent Office Re. Application No. 11782221.3.
Communication Pursuant to Rules 70(2) and 70a(2) EPC dated Mar. 28, 2014 From the European Patent Office Re. Application No. 11833950.6.
Communication Under Rule 71(3) EPC dated Apr. 24, 2014 From the European Patent Office Re. Application No. 11782223.9.
International Preliminary Report on Patentability dated Aug. 7, 2014 From the International Bureau of WIPO Re. Application No. PCT/IL2013/050068.
International Preliminary Report on Patentability dated Oct. 30, 2014 From the International Bureau of WIPO Re. Application No. PCT/IL2013/050339.
International Preliminary Report on Patentability dated Oct. 30, 2014 From the International Bureau of WIPO Re. Application No. PCT/IL2013/050341.
International Search Report and the Written Opinion dated Nov. 20, 2014 From the International Searching Authority Re. Application No. PCT/IL2014/050457.
Invitation Pursuant to Rule 137(4) EPC dated Apr. 4, 2014 From the European Patent Office Re. Application No. 11785792.0.
Invitation Pursuant to Rule 137(4) EPC dated Apr. 8, 2014 From the European Patent Office Re. Application No. 11782222.1.
Invitation Pursuant to Rule 137(4) EPC dated Apr. 10, 2014 From the European Patent Office Re. Application No. 11782476.3.
Invitation to Pay Additional Fees dated Sep. 4, 2014 From the International Searching Authority Re. Application No. PCT/IL2014/050457.
Notice of Allowance dated Oct. 6, 2014 From the US Patent and Trademark Office Re. U.S. Appl. No. 13/880,061.
Notice of Allowance dated Jan. 8, 2015 From the US Patent and Trademark Office Re. U.S. Appl. No. 13/880,061.
Notification of Office Action and Search Report dated Dec. 1, 2014 From the State Intellectual Property Office of the People's Republic of China Re. Application No. 201180060862.8.
Office Action dated Jul. 30, 2014 From the State Intellectual Property Office of the People's Republic of China Re. Application No. 201180060741.3 and Its Summary in English.
Official Action dated Dec. 3, 2014 From the US Patent and Trademark Office Re. U.S. Appl. No. 13/462,956.
Official Action dated Nov. 4, 2014 From the US Patent and Trademark Office Re. U.S. Appl. No. 13/879,400.
Official Action dated Nov. 5, 2014 From the US Patent and Trademark Office Re. U.S. Appl. No. 13/049,022.
Official Action dated Feb. 6, 2015 From the US Patent and Trademark Office Re. U.S. Appl. No. 14/190,113.

(56) References Cited

OTHER PUBLICATIONS

Official Action dated Oct. 7, 2014 From the US Patent and Trademark Office Re. U.S. Appl. No. 13/880,109.
Official Action dated Sep. 10, 2014 From the US Patent and Trademark Office Re. U.S. Appl. No. 14/049,238.
Official Action dated Apr. 14, 2014 From the US Patent and Trademark Office Re. U.S. Appl. No. 13/879,400.
Official Action dated Apr. 23, 2014 From the US Patent and Trademark Office Re. U.S. Appl. No. 13/880,061.
Restriction Official Action dated Jul. 7, 2014 From the US Patent and Trademark Office Re. U.S. Appl. No. 14/049,238.
Restriction Official Action dated Nov. 17, 2014 From the US Patent and Trademark Office Re. U.S. Appl. No. 13/880,066.
Restriction Official Action dated Feb. 27, 2015 From the US Patent and Trademark Office Re. U.S. Appl. No. 13/905,224.
Restriction Official Action dated Oct. 30, 2014 From the US Patent and Trademark Office Re. U.S. Appl. No. 13/880,083.
Search Report dated Jul. 17, 2014 From the State Intellectual Property Office of the People's Republic of China Re. Application No. 201180060741.3 and Its Machine Translation in English.
Supplementary European Search Report dated Mar. 12, 2014 From the European Patent Office Re. Application No. 11833950.6.
Cardiosonic "Cardiosonic New Applications", Cardiosonic, p. 1-20, Mar. 2014.
Cardiosonic "Histological Map of Swin Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Cardiosonic "PAH Preliminary Development Meeting Minutes", Cardiosonic, 2 P., Mar. 23, 2014.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Drake et al. "Problematic Anatomical Sites Around the Pulmonary Artery", Gray's Anatomy for Students, 9 P., 2004.
Gander et al. "Least-Squares Fitting of Circles and Ellipses", BIT Numerical Mathematics, 34(4): 558-578, Dec. 1994.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.
Lafon "Miniature Devices for Minimally Invasive Thermal Ablation by High Intensity Ultrasound", Cargese Workshop 2009, University of Lyon, France, INSERM U556, Presentation, 39 P., 2009.
Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.

Reddy "Sound Intervention", Mount Sinai School of Medicine, MSSM, Presentation, 19 P., 2012.
Schelegle et al. "Vagal Afferents Contribute to Exacerbates Airway Responses Following Ozone and Allergen Challenge", Respiratory Physiology & Neurobiology, 181(3): 277-285, May 31, 2012.
Tibshirani "Regression Shrinkage and Selection Via the Lasso: A Retrospective", Journal of the Royal Statistical Society, Series B: Statistical Methodology, 73(Pt.3): 273-282, 2011.
Tibshirani "Regression Shrinkage and Selection Via the Lasso", Journal of the Royal Statistical Society, Series B: Methodological, 58(1): 267-288, 1996.
Zeller "Percutaneous Renal Denervation System. The New Ultrasound Solution for the Management of Hypertension", Paradise Ultrasound Denervation System, ReCor Medical, 27 P., 2013.
International Preliminary Report on Patentability dated Dec. 3, 2015 From the International Bureau of WIPO Re. Application No. PCT/IL2014/050457.
Notice of Allowance dated Dec. 8, 2015 From the US Patent and Trademark Office Re. U.S. Appl. No. 14/049,238.
Notice of Non-Compliant Amendment dated Sep. 23, 2015 From the US Patent and Trademark Office Re. U.S. Appl. No. 13/880,124.
Notice of Reason for Rejection dated Aug. 25, 2015 From the Japanese Patent Office Re. Application No. 2013-534435.
Official Action dated Jan. 5, 2016 From the US Patent and Trademark Office Re. U.S. Appl. No. 13/880,124.
Official Action dated Sep. 11, 2015 From the US Patent and Trademark Office Re. U.S. Appl. No. 13/880,066.
Official Action dated Sep. 25, 2015 From the US Patent and Trademark Office Re. U.S. Appl. No. 14/190,113.
Translation dated Nov. 18, 2015 of Notice of Reason for Rejection dated Aug. 25, 2015 From the Japanese Patent Office Re. Application No. 2013-534435.
Schnyder et al. "Common Femoral Artery Anatomy Is Influenced by Demographics and Comorbidity: Implications for Cardiac and Peripherial Invasive Studies", Catheterization and Cardiovascular Interventions, 53(3): 289-295, Jul. 2001.
Wu et al. "A Quality Control Program for MR-Guided Focused Ultrasound Ablation Therapy", Journal of Applied Clinical Medical Physics, 3(2): 162-167, Spring 2002.
Communication Pursuant to Article 94(3) EPC dated Apr. 10, 2015 From the European Patent Office Re. Application No. 11782222.1.
Official Action dated Jul. 2, 2015 From the US Patent and Trademark Office Re. U.S. Appl. No. 13/879,400.
Official Action dated Aug. 5, 2015 From the US Patent and Trademark Office Re. U.S. Appl. No. 13/905,224.
Official Action dated Jun. 5, 2015 From the US Patent and Trademark Office Re. U.S. Appl. No. 14/049,238.
Restriction Official Action dated Apr. 14, 2015 From the US Patent and Trademark Office Re. U.S. Appl. No. 13/880,124.
Translation Dated Mar. 12, 2015 of Notification of Office Action and Search Report dated Dec. 1, 2014 From the State Intellectual Property Office of the People's Republic of China Re. Application No. 201180060862.8.
Ali et al. "Signal Processing Overview of Ultrasound Systems for Medical Imaging", Texas Instruments White Paper, SPRAB12: 1-27, Nov. 2008.
Bambi et al. "Real-Time Digital Processing of Doppler Ultrasound Signals", IEEE International Conference on Acoustics, Speech, and Signal Processing, Proceedings, (ICASSP '05), (5): v/977-v/980, 23-23 Mar. 2005.
Shung "Doppler Flow Measurements", Diagnostic Ultrasound—Imaging and Blood Flow Measurements, Chap.5:103-104, 2006.
Applicant-Initiated Interview Summary dated Feb. 22, 2016 From the US Patent and Trademark Office Re. U.S. Appl. No. 13/880,066.
Communication Pursuant to Article 94(3) EPC dated Feb. 8, 2016 From the European Patent Office Re. Application No. 11833950.6.
Communication Pursuant to Article 94(3) EPC dated Jul. 20, 2016 From the European Patent Office Re. Application No. 11782221.3.
Communication Pursuant to Article 94(3) EPC dated Jul. 27, 2016 From the European Patent Office Re. Application No. 11782222.1.
Decision of Rejection dated Apr. 28, 2016 From the Japanese Patent Office Re. Application No. 2013-534435 and Its Machine Translation in English.

(56) References Cited

OTHER PUBLICATIONS

International Search Report and the Written Opinion dated May 2, 2016 From the International Searching Authority Re. Application No. PCT/IL2015/051145.
Invitation Pursuant to Rule 137(4) EPC dated Mar. 21, 2016 From the European Patent Office Re. Application No. 11782222.1.
Invitation to Pay Additional Fees dated Mar. 4, 2016 From the International Searching Authority Re. Application No. PCT/IL2015/051145.
Notice of Allowance dated Jul. 18, 2016 From the US Patent and Trademark Office Re. U.S. Appl. No. 13/879,400.
Official Action dated Jun. 3, 2016 From the US Patent and Trademark Office Re. U.S. Appl. No. 13/880,066.
Official Action dated Jun. 10, 2016 From the US Patent and Trademark Office Re. U.S. Appl. No. 14/190,113.
Official Action dated 126 Jul. 2016 From the US Patent and Trademark Office Re. U.S. Appl. No. 13/880,124.
Official Action dated Apr. 29, 2016 From the US Patent and Trademark Office Re. U.S. Appl. No. 13/905,224.
Shelton Jr. et al. "A Nondestructive Technique to Measure Pulmonary Artery Diameter and Its Pulsatile Variations", Journal of Applied Physiology, 33(4): 542-544, Oct. 1972.
Applicant-Initiated Interview Summary dated Apr. 25, 2018 From the US Patent and Trademark Office Re. U.S. Appl. No. 14/394,276. (3 pages).
Communication Pursuant to Rule 164(1) EPC: Supplementary Partial European Search Report and the European Provisional Opinion dated May 18, 2018 From the European Patent Office Re. Application No. 15862313.2. (15 Pages).
Restriction Official Action dated May 24, 2018 From the US Patent and Trademark Office Re. U.S. Appl. No. 14/889,890. (8 pages).
International Search Report and the Written Opinion dated Aug. 28, 2018 From the International Searching Authority Re. Application No. PCT/IL2018/050322. (40 Pages).
International Search Report and the Written Opinion dated Aug. 29, 2018 From the International Searching Authority Re. Application No. PCT/IL2018/050321. (16 Pages).
Invitation to Pay Additional Fees dated Jun. 21, 2018 From the International Searching Authority Re. Application No. PCT/IL2018/050322. (3 Pages).
Invitation to Pay Additional Fees dated Jun. 25, 2018 From the International Searching Authority Re. Application No. PCT/IL2018/050321. (2 Pages).
Official Action dated Aug. 10, 2018 From the US Patent and Trademark Office Re. U.S. Appl. No. 14/190,113. (11 pages).
Official Action dated Oct. 11, 2018 From the US Patent and Trademark Office Re. U.S. Appl. No. 14/394,276. (200 Pages).
Official Action dated Oct. 31, 2018 From the US Patent and Trademark Office Re. U.S. Appl. No. 13/905,224. (23 pages).
Restriction Official Action dated Jan. 4, 2019From the US Patent and Trademark Office Re. U.S. Appl. No. 15/529,137. (8 pages).
Supplementary European Search Report and the European Search Opinion dated Sep. 5, 2018 From the European Patent Office Re. Application No. 15862313.2. (13 Pages).
Van Campen et al. "Bisoprolol in Idiopathic Pulmonary Arterial Hypertension: an Explorative Study", European Respiratory Journal, 48: 787-796, 2016.
International Preliminary Report on Patentability dated Oct. 3, 2019 From the International Bureau of WIPO Re. Application No. PCT/IL2018/050322. (16 Pages).

\* cited by examiner

FIG. 12A

CAROTID

10 MHz

| w/cm^2 | 1-10 | 11-20 | 21-30 | 31-40 | 41-50 | 51-60 |
|---|---|---|---|---|---|---|
| AREA | | | PA | M | | M |
| DAMAGE | | | S | S | | L |
| NERVE | | | N | N | | Y |
| pig | | | 7 | 7 | | 8 |
| point | | | 6 | 7 | | 6 |

15 MHz

| w/cm^2 | 1-10 | 11-20 | 21-30 | 31-40 | 41-50 | 51-60 |
|---|---|---|---|---|---|---|
| AREA | | | M | | | |
| DAMAGE | | | L | | | |
| NERVE | | | Y | | | |
| pig | | | 9 | | | |
| point | | | 4 | | | |

20 MHz

| w/cm^2 | 1-10 | 11-20 | 21-30 | >31 |
|---|---|---|---|---|
| AREA | PA | PA | M | IEL |
| DAMAGE | L | L | L | S |
| NERVE | N | Y | Y | Y |
| pig | 7 | 7 | 7 | 7 |
| point | 2 | 3 | 5 | 8 |

RENAL

10 MHz

| w/cm^2 | 1-10 | 11-20 | 21-30 | 31-40 | >40 |
|---|---|---|---|---|---|
| AREA | | | PA | PA | M |
| DAMAGE | | | S | M | L |
| NERVE | | | Y | Y | Y |
| pig | | | 5 | 8 | 8 |
| point | | | 5 | 2 | 2 |

15 MHz

| w/cm^2 | 1-10 | 11-20 | 21-30 | 31-40 | 41-50 | 51-60 | >60 |
|---|---|---|---|---|---|---|---|
| AREA | | | | | | | M |
| DAMAGE | | | | | | | L |
| NERVE | | | | | | | Y |
| pig | | | | | | | 9 |
| point | | | | | | | 1 |

20 MHz

| w/cm^2 | 1-10 | 11-20 | 21-30 | 31-40 | 41-50 | 51-60 | 51-60 | 51-60 |
|---|---|---|---|---|---|---|---|---|
| AREA | | | | M | M | M | M | IEM |
| DAMAGE | | | | M | M | M | M | S |
| NERVE | | | | Y | Y | Y | Y | N |
| pig | | | | 7 | 7 | 7 | 7 | 6 |
| point | | | | 1 | 1 | 1 | 1 | 2 |

FIG.12B: US parameters vs Thermal effects for 10 Mhz

| Pig no. | R/L | F | I | T | slide no. | Location (mm) | loc no. | Med | L | Th | W | S |
|---|---|---|---|---|---|---|---|---|---|---|---|---|
| 25 | R | 10 | 20 | 10 | RR5+10 | 13 | 2 | 0.66 | 1.49 | 1 | 2.78 | 1 |
|  |  |  |  |  | RR6+10 | 16 | 2 | 0.66 | 2.29 | 0.06 | 0.06 | 0.5 |
|  |  |  |  |  |  |  |  | 0.66 | 1.73 | 0.17 | 0.48 | 0.5 |
| 25 | L | 10 | 20 | 10 | RL2+15 | 4.5 | 1 | 0.78 | 4.18 | 0.64 | 1.27 | 1 |
|  |  |  |  |  | RL3+10 | 7 | 1 | 0.62 | 1.32 | 0.19 | 0.89 | 0.5 |
|  |  |  |  |  |  |  | average | 0.676 | 2.202 | 0.412 | 0.996 | 0.7 |
|  |  |  |  |  |  |  | stdev | 0.060663004 | 1.16489055 | 0.39669888 | 1.0917097 | 0.27386128 |
| 24 | R | 10 | 20 | 30 | RR2+05 | 3.5 | 1 | 0.53 | 2.27 | 2.56 | 0.53 | 0.5 |
| 24 | L | 10 | 20 | 30 | RL2+10 | 4 | 1 | 0.48 | 1.49 | 3.14 | 2.38 | 1 |
|  |  |  |  |  |  |  | average | 0.505 | 1.88 | 2.85 | 1.455 | 0.75 |
|  |  |  |  |  |  |  | stdev | 0.035355339 | 0.55154329 | 0.41012193 | 1.3081475 | 0.35355339 |
| 30 | R | 10 | 25 | 30 | RR2+00 | 3 | 1 | 0.59 | 2.8 | 2.79 | 1.48 | 1 |
|  |  |  |  |  | RR5+00 | 12 | 3 | 0.53 | 3.38 | 0.25 | 0.45 | 0.5 |
| 30 | L | 10 | 25 | 30 | RL2+10 | 4 | 1 | 0.65 | 2.42 | 2.64 | 1.75 | 1 |
|  |  |  |  |  | RL3+05 | 6.5 |  | 0.76 | 1.47 | 3.32 | 3.28 | 1 |
|  |  |  |  |  | RL4+05 | 9.5 | 2 | 0.55 | 3.12 | 4.8 | 3.14 | 1 |
|  |  |  |  |  |  |  | average | 0.616 | 2.638 | 2.76 | 2.02 | 0.9 |
|  |  |  |  |  |  |  | stdev | 0.092628289 | 0.74513086 | 1.64245243 | 1.1907351 | 0.2236068 |
| 38 | R | 10 | 30 | 10 | RR2+10 | 4 | 1 | 0.48 | 3.84 | 0.7 | 0.46 | 0.5 |
|  |  |  |  |  | RR2+15 | 4.5 | 1 | 0.44 | 2.12 | 0.86 | 1.38 | 1 |
|  |  |  |  |  | RR3+00 | 6 | 1 | 0.56 | 0 | 0.44 | 1.6 | 2 |
|  |  |  |  |  | RR5+10 | 13 | 2 | 0.49 | 2.22 | 1.15 | 3 | 1 |
|  |  |  |  |  |  |  | average | 0.4925 | 2.045 | 0.7875 | 1.61 | 1.125 |
|  |  |  |  |  |  |  | stdev | 0.049916597 | 1.57483332 | 0.2972513 | 1.0500159 | 0.62915287 |
| 32 | R | 10 | 30 | 30 | RR2+15 | 4.5 | 1 | 0.5 | 1.56 | 0.47 | 0.54 | 0.5 |
|  |  |  |  |  |  |  |  | 0.5 | 3.33 | 0.6 | 1.39 | 1 |
|  |  |  |  |  |  |  |  | 0.5 | 0.34 | 2.29 | 4.08 | 2 |
|  |  |  |  |  | RR3+05 | 6 | 1 | 0.44 | 1.4 | 2.26 | 1.37 | 1 |
|  |  |  |  |  |  |  |  | 0.44 | 1.63 | 1.18 | 1.03 | 0.5 |
|  |  |  |  |  |  |  |  | 0.44 | 0 | 0.54 | 1.43 | 2 |
|  |  |  |  |  |  |  |  | 0.44 | 0 | 1.65 | 0.74 | 2 |
|  |  |  |  |  |  |  |  | 0.44 | 0 | 0.29 | 0.25 | 2 |
|  |  |  |  |  |  |  |  | 0.44 | 4.12 | 1.26 | 3.01 | 1 |
|  |  |  |  |  | RR4+15 | 10.5 | 2 | 0.46 | 1.27 | 1.92 | 2.31 | 1 |
|  |  |  |  |  |  |  |  | 0.46 | 2.03 | 1.06 | 1.93 | 1 |
|  |  |  |  |  |  |  |  | 0.46 | 0 | 0.5 | 0.5 | 2 |
| 32 | L | 10 | 30 | 30 | RL3+00 | 6 | 1 | 0.53 | 6.01 | 3.1 | 4.1 | 1 |
|  |  |  |  |  |  | 9.5 | 2 | 0.43 | 1.81 | 2.73 | 3.88 | 1 |
|  |  |  |  |  |  |  |  | 0.43 | 2.33 | 0.3 | 2.56 | 1 |
|  |  |  |  |  |  |  |  | 0.43 | 1.6 | 3.71 | 4.86 | 1 |
|  |  |  |  |  |  |  |  | 0.43 | 1.12 | 3.81 | 2.04 | 1 |
| 23 | R | 10 | 30 | 30 | RR2+15 | 4.5 | 1 | 0.55 | 1.11 | 2.21 | 1.16 | 1 |
|  |  |  |  |  | RR3+10 | 7 | 2 | 0.51 | 0.88 | 0.54 | 0.4 | 1 |
|  |  |  |  |  |  |  |  | 0.51 | 1.65 | 1.47 | 0.64 | 1 |
|  |  |  |  |  | RR4+00 | 9 | 2 | 0.67 | 1.54 | 1.67 | 1.78 | 1 |
|  |  |  |  |  | RR4+15 | 10.5 | 2 | 0.54 | 3.31 | 2.42 | 0.27 | 0.5 |
| 23 | L | 10 | 30 | 30 | RL2+05 | 3.5 | 1 | 0.66 | 3.44 | 1 | 0.45 | 1 |
|  |  |  |  |  |  |  |  | 0.66 | 4.29 | 4.92 | 4.16 | 1 |
|  |  |  |  |  | RL2+15 | 4.5 | 1 | 0.84 | 4.01 | 1.5 | 1.68 | 1 |
|  |  |  |  |  | RL3+00 | 6 | 1 | 0.56 | 3.48 | 2.28 | 1.45 | 1 |
|  |  |  |  |  |  |  |  | 0.56 | 2.95 | 0.41 | 0.7 | 1 |
|  |  |  |  |  |  |  | average | 0.512222222 | 2.04481481 | 1.70703704 | 1.8040741 | 1.12962963 |
|  |  |  |  |  |  |  | stdev | 0.098071141 | 1.54292273 | 1.20306281 | 1.3761185 | 0.45133547 |

| Pig no. | R/L | F | I | T | slide no. | Location (mm) | loc no. | Med | L | Th | W | S |
|---|---|---|---|---|---|---|---|---|---|---|---|---|
| 31 | R | 10 | 35 | 30 | RR2+15 | 4.5 | 1 | 0.59 | 1.81 | 2.81 | 4.87 | 1 |
|  |  |  |  |  |  |  | 1 | 0.59 | 1.64 | 1.06 | 0.68 | 1 |
|  |  |  |  |  |  |  | 1 | 0.50 | 1.8 | 1.44 | 1.18 | 1 |
|  |  |  |  |  | RR3+10 | 7 | 1 | 0.48 | 0.28 | 2.82 | 4.11 | 2 |
|  |  |  |  |  |  |  | 1 | 0.48 | 0.5 | 2 | 2.18 | 1 |
|  |  |  |  |  | RR4+10 | 10 | 2 | 0.62 | 1.72 | 0.1 | 0.1 | 0.5 |
|  |  |  |  |  | RR4+15 | 10.5 | 2 | 0.7 | 0.44 | 4.87 | 3.99 | 2 |
|  |  |  |  |  |  |  | 2 | 0.7 | 2.67 | 0.37 | 0.61 | 0.5 |
|  |  |  |  |  |  |  | 2 | 0.7 | 0.14 | 0.44 | 0.54 | 2 |
| 31 | R | 10 | 35 | 30 | RL3+15 | 7.5 | 1 | 0.53 | 1.64 | 3.9 | 3.47 | 1 |
|  |  |  |  |  | RL4+05 | 9.5 | 2 | 0.81 | 1.6 | 7.64 | 5.1 | 1 |
|  |  |  |  |  |  |  | 2 | 0.81 | 2 | 6.89 | 3.21 | 2 |
|  |  |  |  |  |  |  | average | 0.633333333 | 1.35333333 | 2.86166667 | 2.5033333 | 1.25 |
|  |  |  |  |  |  |  | stdev | 0.112519359 | 0.80374502 | 2.52055489 | 1.833151 | 0.58387421 |

FIG.12C: US parameters vs Thermal effects for 20 Mhz

| Pig no. | R/L | F | I | T | slide no. | Location (mm) | loc no. | Med | L | Th | W | S |
|---|---|---|---|---|---|---|---|---|---|---|---|---|
| 34 | R | 20 | 10 | 30 | RR5+05 | 12.5 | 1 | 0.47 | 1.24 | 0.74 | 1.64 | 0.5 |
|  |  |  |  |  |  |  |  | 0.47 | 1.03 | 0.26 | 0.87 | 0.5 |
|  |  |  |  |  | RR5+15 | 13.5 |  | 0.6 | 2.49 | 0.61 | 0.55 | 1 |
|  |  |  |  |  |  |  |  | 0.6 | 1.81 | 2.81 | 0.8 | 1 |
|  |  |  |  |  |  |  | average | 0.535 | 1.6425 | 1.105 | 0.965 | 0.75 |
|  |  |  |  |  |  |  | stdev | 0.0750555 | 0.6540833 | 1.1545995 | 0.4704962 | 0.2886751 |
| 29 | R | 20 | 20 | 10 | RR1+10 | 1 | 1 | 0.6 | 1 | 1.52 | 3.49 | 1 |
|  |  |  |  |  | RR2+05 | 3.5 | 1 | 0.65 | 0.28 | 2.3 | 3.72 | 2 |
|  |  |  |  |  | RR4+15 | 10.5 | 2 | 0.62 | 1.36 | 0.23 | 0.17 | 0.5 |
|  |  |  |  |  |  |  |  | 0.62 | 2.74 | 0.3 | 0.44 | 0.5 |
|  |  |  |  |  | RR5+10 | 13 | 2 | 0.54 | 1.35 | 3.7 | 2.7 | 1 |
|  |  |  |  |  |  |  |  | 0.54 | 1.53 | 0.27 | 0.31 | 0.5 |
| 29 | R | 20 | 20 | 10 | RL1+05 | 0.5 | 1 | 0.73 | 0.91 | 1.57 | 1.63 | 1 |
|  |  |  |  |  | RL1+15 | 1.5 | 1 | 0.67 | 1.03 | 3.93 | 2.79 | 1 |
|  |  |  |  |  | RL3+10 | 7 | 1 | 0.54 | 5 | 0.26 | 0.94 | 0.5 |
| 40 | R | 20 | 20 | 10 | RR6+05 | 15.5 | 1 | 0.52 | 0.3 | 2.7 | 3.36 | 2 |
|  |  |  |  |  |  |  |  | 0.52 | 0.2 | 3.51 | 2.18 | 2 |
|  |  |  |  |  |  |  |  | 0.52 | 0.23 | 3.14 | 2.86 | 2 |
|  |  |  |  |  |  |  | average | 0.5891667 | 1.3275 | 1.9525 | 2.0491667 | 1.1666667 |
|  |  |  |  |  |  |  | stdev | 0.0698646 | 1.3659437 | 1.4524658 | 1.3067758 | 0.6513389 |
| 27 | L | 20 | 20 | 30 | RL2+15 | 4.5 | 1 | 0.6 | 0.42 | 3.79 | 5.75 | 2 |
|  |  |  |  |  | RL3+00 | 6 | 1 | 0.6 | 0.42 | 2.1 | 1.73 | 2 |
|  |  |  |  |  | RL3+05 | 6.5 | 1 | 0.63 | 0.12 | 1.67 | 2.6 | 2 |
|  |  |  |  |  |  |  |  | 0.63 | 2.64 | 0.21 | 0.18 | 0.5 |
|  |  |  |  |  |  |  |  | 0.63 | 2.23 | 4.47 | 5.73 | 1 |
| 27 | R | 20 | 20 | 30 | RR2+00 | 3 | 1 | 0.5 | 0 | 3.85 | 2.68 | 2 |
|  |  |  |  |  |  |  |  | 0.5 | 7.16 | 2.15 | 3 | 1 |
|  |  |  |  |  |  |  |  | 0.5 | 1.49 | 2.16 | 1.97 | 1 |
|  |  |  |  |  | RR2+10 | 4 | 1 | 0.48 | 0 | 2.54 | 2.07 | 2 |
|  |  |  |  |  |  |  |  | 0.48 | 0.88 | 1.39 | 3.15 | 1 |
|  |  |  |  |  |  |  | average | 0.555 | 1.536 | 2.433 | 2.884 | 1.45 |
|  |  |  |  |  |  |  | stdev | 0.0677003 | 2.1852241 | 1.2861402 | 1.7214348 | 0.5986095 |
| Pig no. | R/L | F | I | T | slide no. | Location (mm) | loc no. | Med | L | Th | W | S |
| 33 | L | 20 | 30 | 10 | RL3+05 | 6.5 | 1 | 0.72 | 1.17 | 3.95 | 1.42 | 1 |
| 33 | R | 20 | 30 | 10 | RR3+15 | 7.5 | 1 | 0.65 | 0 | 3.34 | 1.88 | 2 |
|  |  |  |  |  | RR4+10 | 10 | 2 | 0.67 | 1.06 | 2.13 | 4.53 | 1 |
|  |  |  |  |  |  |  |  | 0.67 | 0.31 | 6.81 | 4.56 | 2 |
|  |  |  |  |  | RR5+10 | 13 | 2 | 0.58 | 1.5 | 0.54 | 0.12 | 0.5 |
|  |  |  |  |  |  |  | average | 0.658 | 0.808 | 3.354 | 3.302 | 1.3 |
|  |  |  |  |  |  |  | stdev | 0.0506952 | 0.6273516 | 2.3300279 | 1.5267351 | 0.6708204 |

For the renal arteries:

C1 = 435.9
C2 = 92.47
C3 = 1.491
C4 = 1
C5 = 47.84

For the carotid arteries:

C1 = 483.2
C2 = 93
C3 = 2.613
C4 = 3.748
C5 = 47

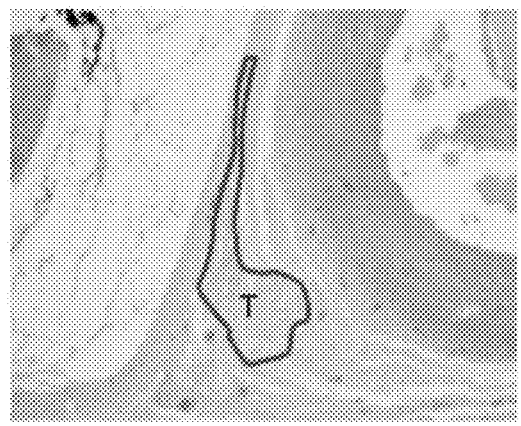 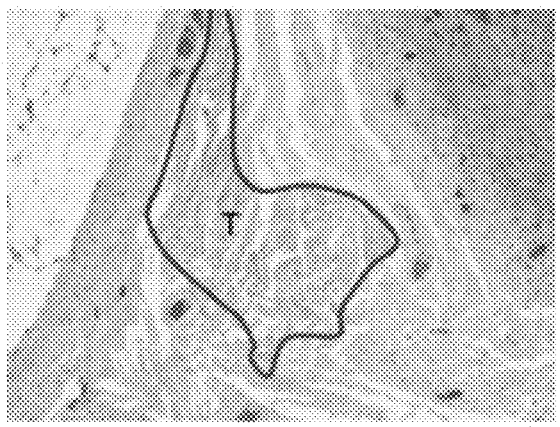
FIG. 19A  FIG. 19B
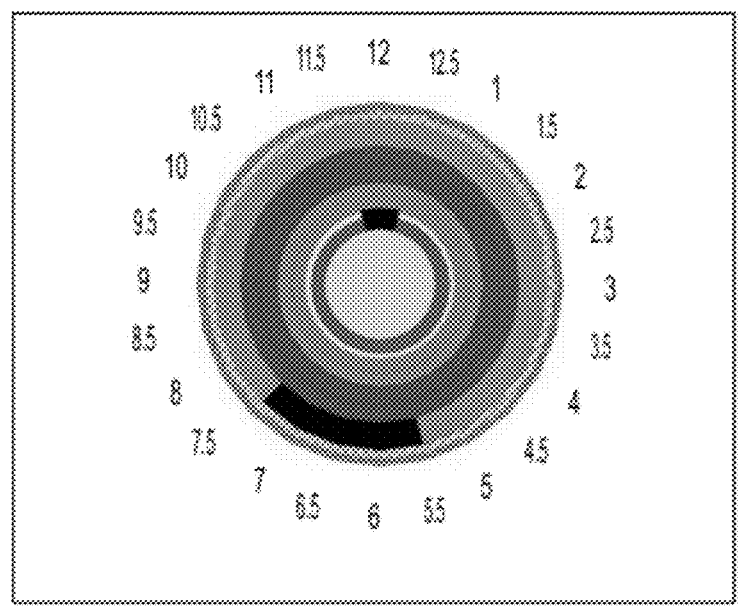
FIG. 19C

TISSUE TREATMENT

RELATED APPLICATIONS

This application is a Continuation-in-Part (CIP) of PCT Patent Application No. PCT/IB2011/054640 filed on Oct. 18, 2011, which claims the benefit of priority of U.S. Provisional Patent Application Nos. 61/393,947 filed on Oct. 18, 2010, and 61/453,239 filed on Mar. 16, 2011. The contents of the above applications are incorporated herein by reference in their entirety.

This application is also related to co-pending and co-assigned patent applications entitled:

"THERAPEUTICS RESERVOIR" (PCT/IB2011/054634), which teaches an apparatus and a method for forming a drug reservoir as a possible application of the ultrasound energy application described herein;

"AN ULTRASOUND TRANSCEIVER AND CONTROL OF A THERMAL DAMAGE PROCESS" (PCT/IB2011/054639), which teaches an apparatus and method for performing ultrasonic imaging, such as to provide feedback about the effect of treatment on tissues as described herein;

"ULTRASOUND TRANSDUCER" (U.S. patent application Ser. No. 13/049,151), which teaches an apparatus for generating relatively high intensity ultrasound, such as to apply energy to cause the desired effects in tissue as described herein;

"AN ULTRASOUND TRANSDUCER AND USES THEREOF" (U.S. patent application Ser. No. 13/049,013), which teaches a method for feedback and control of the ultrasonic emission element, such as to use the same ultrasonic element for treatment and imaging, potentially useful when treating and imaging as described herein;

"AN ULTRASOUND TRANSDUCER AND COOLING THEREOF" (U.S. patent application Ser. No. 13/049,022), which teaches a method for cooling of the ultrasonic emission element, potentially useful when applying energy as described herein;

"SEPARATION DEVICE FOR ULTRASOUND ELEMENT" (PCT/IB2011/054638), which teaches a device to prevent the ultrasonic emission element from touching the blood vessel wall, potentially useful for preventing damage to the intima layer when applying energy as described herein;

"SELECTIVE REDUCTION OF NERVE ACTIVITY" (U.S. Provisional Application No. 61/590,423) which teaches devices and/or method for selectively reducing nerve function, potentially useful when applying energy as described herein; and "TISSUE TREATMENT" (a U.S. Provisional Application being co-filed with the instant Application and identified under U.S. Provisional Application No. 61/625,810), which teaches devices and/or methods for selectively causing tissue damage, potentially useful for applying energy as described herein.

The disclosures of the above applications are incorporated herein by reference.

FIELD AND BACKGROUND OF THE INVENTION

The present invention, in some embodiments thereof, relates to a method of treatment of tissue and, more particularly, but not exclusively, to a method of selectively targeting and treating tissue using unfocused ultrasound energy.

Sverdlik et al, in PCT/IL2008/000234, filed Feb. 21, 2008 disclose: "Described is a method of stabilizing blood vessel wall abnormality. The method includes ultrasonically heating at least a portion of the blood vessel wall having the abnormality; monitoring a parameter related to a property of at least a portion of the heated portion of the blood vessel wall; and stopping the heating when the monitored parameter changes by a predetermined factor or after the monitored parameter changes in a slow enough rate."

Additional background art includes:
EP 1769759
U.S. Pat. No. 5,699,804
U.S. Pat. No. 7,410,486
U.S. Pat. No. 7,621,929
U.S. Pat. No. 7,717,948
U.S. Pat. No. 7,771,372
US patent application 2008228111
US patent application 2009216246
US patent application 2010091112
Xu, D. S., & Pollock, M. (1994). Experimental nerve thermal-injury. Brain, 117, 375-384.
Katholi et al. "Renal nerves in the maintenance of hypertension: a potential therapeutic target" Curr Hypertens Rep. 2010 June; 12(3):196-204.
Lele, P. P. (1963). Effects of Focused Ultrasonic Radiation on Peripheral Nerve, With Observations On Local Heating. Experimental Neurology, 8(1), 47-83.
Fung L C et al. Effects of temperature on tissue thermal injury and wound strength after photothermal wound closure. Lasers Surg Med. 1999; 25(4):285-90.
Worthington, A. E., et al, Ultrasound in Med. & Biol., Vol. 28, No. 10, pp. 1311-1318, 2002.
Damianou et al, J Acoust Soc Am. 1997 July; 102(1):628-34.

SUMMARY OF THE INVENTION

An aspect of some embodiments of the invention relates to a method of selectively treating a volume of tissue using unfocused ultrasound energy having an acoustic intensity profile of over 1 Watt per square centimeter.

There is provided in accordance with an exemplary embodiment of the invention a method of treating a subject suffering from a nerve related disorder, the method comprising:

causing a damage region to one or both of a lumen wall or nearby surrounding tissues, the damage region encompassing a volume having dimensions of less than about 6.8 mm in a substantially radial direction, less than about 5.8 mm in a direction substantially tangential to the lumen, less mm in a substantially axial direction, the damage region being located no closer than about 0.2 mm from an inner wall of the lumen, the damage region comprises of greater than about 60% of collagen denatured tissue.

In an exemplary embodiment of the invention, the radial dimension is less than about 4 mm. Alternatively, the radial dimension is less than about 2 mm.

In an exemplary embodiment of the invention, the tangential direction is less than about 4 mm. Alternatively, the tangential direction is less than about 2 mm.

In an exemplary embodiment of the invention, the damage region comprises of less than about 60% of collagen denatured tissue. Alternatively, the damage region comprises of less than about 20% of collagen denatured tissue.

In an exemplary embodiment of the invention, the damage region is located no closer than about 0.5 mm from the inner wall. Alternatively, the damage region is located no closer than about 2 mm from the inner wall.

In an exemplary embodiment of the invention, the damage region has a substantially trapezoidal shape.

In an exemplary embodiment of the invention, the axial direction is less than about 8 mm. Alternatively, the axial direction is less than about 6 mm.

In an exemplary embodiment of the invention, the collagen denatured tissue comprises necrotic tissue.

In an exemplary embodiment of the invention, the nerve related disorder comprises hypertension.

In an exemplary embodiment of the invention, causing damage comprises causing damage to reduce kidney norepinephrine levels by at least 50% at 30 days after the treatment.

In an exemplary embodiment of the invention, the lumen is selected from the group comprising: renal artery, aorta, renal artery ostium.

In an exemplary embodiment of the invention, the damage region comprises at least one nerve and wherein the causing damage comprises causing damage to the at least one nerve.

In an exemplary embodiment of the invention, the causing damage comprises causing damage without significantly damaging tissue outside of the damage region.

In an exemplary embodiment of the invention, the damage region does not include an intima of the lumen.

In an exemplary embodiment of the invention, the causing damage comprises causing damage from within the lumen.

In an exemplary embodiment of the invention, the method further comprises repeating the causing damage to one or more additional damage regions, the damage regions being spaced apart. Optionally, the spaced apart damage regions are distributed around a circumference of the lumen. Optionally or alternatively or additionally, the spaced apart damage regions are distributed longitudinally along the lumen. Optionally, the spaced apart damage regions comprise 2-8 locations.

In an exemplary embodiment of the invention, the causing damage comprises causing damage without raising a blood temperature above 50 degrees Celsius. Alternatively, the causing damage comprises causing damage without raising a blood temperature above 43 degrees Celsius.

In an exemplary embodiment of the invention, causing damage comprises causing damage without causing significant stenosis as an aftermath of the treatment.

In an exemplary embodiment of the invention, causing damage comprises causing damage without causing significant contraction of the lumen.

In an exemplary embodiment of the invention, causing damage comprises causing damage without causing significant shrinkage in the damaged tissue regions.

In an exemplary embodiment of the invention, causing damage comprises causing damage without causing significant coagulation of blood in the lumen.

In an exemplary embodiment of the invention, causing damage comprises causing damage without causing significant damage to an intima. Alternatively, causing damage comprises causing damage without causing significant damage to an intima and a media. Alternatively, causing damage comprises causing damage without causing significant damage to an intima a media and an adventitia.

In an exemplary embodiment of the invention, causing damage comprises causing damage with substantially clear demarcation of the damage regions and untreated regions.

In an exemplary embodiment of the invention, causing damage comprises causing damage without significantly damaging tissue outside the damage region after repeating the causing damage to the damage region up to three additional times.

In an exemplary embodiment of the invention, the damage region is confined to one or more tissue layer selected from peri-adventitia, adventitia, media.

In an exemplary embodiment of the invention, the causing damage comprises applying intracorporeal unfocused ultrasound energy to cause the damage. Optionally, a frequency of the unfocused ultrasound energy ranges from about 10 Mhz to about 20 Mhz. Optionally or additionally, the unfocused ultrasound is applied for a time period ranging from about 5 seconds to about 180 seconds per damage region. Alternatively, the unfocused ultrasound is applied for a time period ranging from about 5 seconds to about 30 seconds per damage region. Optionally or additionally, an intensity of the unfocused ultrasound ranges from about 10 watt/cm$^2$ to about 35 watt/cm$^2$.

There is provided in accordance with an exemplary embodiment of the invention a method of treating a subject suffering from a nerve related disorder, the method comprising:

causing a damage region to one or both of a lumen wall or surrounding tissues, the damage region encompassing a volume having dimensions of less than about 3 mm in a substantially radial direction, less than about 4 mm in a direction substantially tangential to the lumen, less than about 6 mm in a substantially axial direction, the damage region being located no closer than about 0.5 mm from an inner wall of the lumen, the damage region comprises of less than about 60% of collagen denatured tissue, and the damage region having a substantially trapezoidal shape.

There is provided in accordance with an exemplary embodiment of the invention a method of treating hypertension, the method comprising:

causing a damage region to one or both of a renal wall or surrounding tissues, the damage region encompassing a volume having dimensions of less than about 4 mm in a substantially radial direction, less than about 5 mm in a direction substantially tangential to the renal artery, less than about 6 mm in a substantially axial direction, the damage region being located no closer than about 0.5 mm from an inner wall of the renal artery, the damage region comprises of less than about 60% of collagen denatured tissue, thereby reducing kidney norepinephrine levels by at least 30% at 30 days after a treatment.

There is provided in accordance with an exemplary embodiment of the invention a method of treating hypertension comprising:

applying intracorporeal unfocused ultrasound energy to one or more spaced apart locations in a wall of a renal artery, thereby damaging tissue regions and reducing kidney norepinephrine levels by at least 30% at 30 days after the treatment, but which the amount of the ultrasound energy is not significantly damaging to tissue outside the regions, and wherein an intima of the renal artery is not significantly damaged.

There is provided in accordance with an exemplary embodiment of the invention a method of forming a time insensitive area of thermal damage in one or more of a lumen wall or surrounding tissues, the method comprising:

adjusting blood flow in the lumen so that energy transmitted for a length of time of at least a factor of 1:2 within a time range forms the same area of thermal damage by raising a temperature within the area, the energy is transmitted from within the lumen.

In an exemplary embodiment of the invention, the range comprises 5 seconds to 180 seconds. Alternatively, the range comprises 5 seconds to 30 seconds.

In an exemplary embodiment of the invention, adjusting comprises adjusting blood flow along an inner wall of the lumen adjacent to the damage region and in the path of the energy.

There is provided in accordance with an exemplary embodiment of the invention a method of selectively damaging nerves in one or more of a lumen wall or surrounding tissues, the nerves damaged without significant histologically visible damage, the nerves located outside of an area of histologically visible thermal damage, the method comprising:

adjusting blood flow in the lumen so that blood flowing next to an inner wall of the lumen is slowed down and blood flow in the lumen flowing next to an energy emitter is not slowed down enough to raise a temperature of the blood beyond a safe level.

In an exemplary embodiment of the invention, the histologically visible damage comprises damage visible using H&E staining.

In an exemplary embodiment of the invention, the nerves are heated to a temperature between 47 degrees Celsius and 60 degrees Celsius.

In an exemplary embodiment of the invention, a reduction in kidney norepinephrine levels does not correlate with the visible damage.

There is provided in accordance with an exemplary embodiment of the invention a device for controlling blood flow in a lumen comprising:

a catheter having a distal end, the distal end comprising one or more extensions positioned and shaped to slow down blood flow close to a wall of the lumen in an amount sufficient to reduce cooling of the blood on tissues in the wall, and to not slow down blood flow across a surface of an ultrasound emitter element so that the blood flow is not heated past a safe level, the extension disposed at one or both of upstream or downstream relative to the ultrasound emitter, and the extension protrudes above a surface of the catheter.

In an exemplary embodiment of the invention, the distal end comprises the ultrasound emitter element.

In an exemplary embodiment of the invention, the catheter further comprises an adjustment member to change a shape of the extension and thereby control the blood flow.

In an exemplary embodiment of the invention, the extension is positioned to create turbulence in blood so that heated blood next to the ultrasound emitter is transferred next to the lumen wall.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a flowchart of a treatment method, in accordance with an exemplary embodiment of the invention;

FIG. 1B is a flowchart of a more detailed treatment method of FIG. 1A, in accordance with an exemplary embodiment of the invention;

FIG. 2 is an illustration of an embodiment of the treatment system for selectively treating tissues, in accordance with an exemplary embodiment of the invention;

FIG. 3 is an illustration of the human body showing exemplary treatment locations, useful in practicing some embodiments of the invention;

FIG. 4 is an illustration of the renal artery, showing exemplary treatment locations, in accordance with an exemplary embodiment of the invention;

FIG. 5 is an illustration of ultrasound energy treating tissues, in accordance with an exemplary embodiment of the invention;

FIG. 6A is a cross section of an arterial wall, illustrating selective tissue treatment, in accordance with an exemplary embodiment of the invention;

FIG. 6B is a cross sectional view, FIG. 6C is a side view and FIG. 6D is a top view illustrating a controllable volume of treatment to tissue, in accordance with an exemplary embodiment of the invention;

FIG. 7A is an exemplary graph illustrating a temperature profile, useful in practicing some embodiments of the invention;

FIG. 7B is an exemplary graph illustrating relative tissue attenuation, useful in practicing some embodiments of the invention;

FIG. 7C is an exemplary graph illustrating some associations between heat removal rates and treatment, useful in practicing some embodiments of the invention;

Figure 7A:
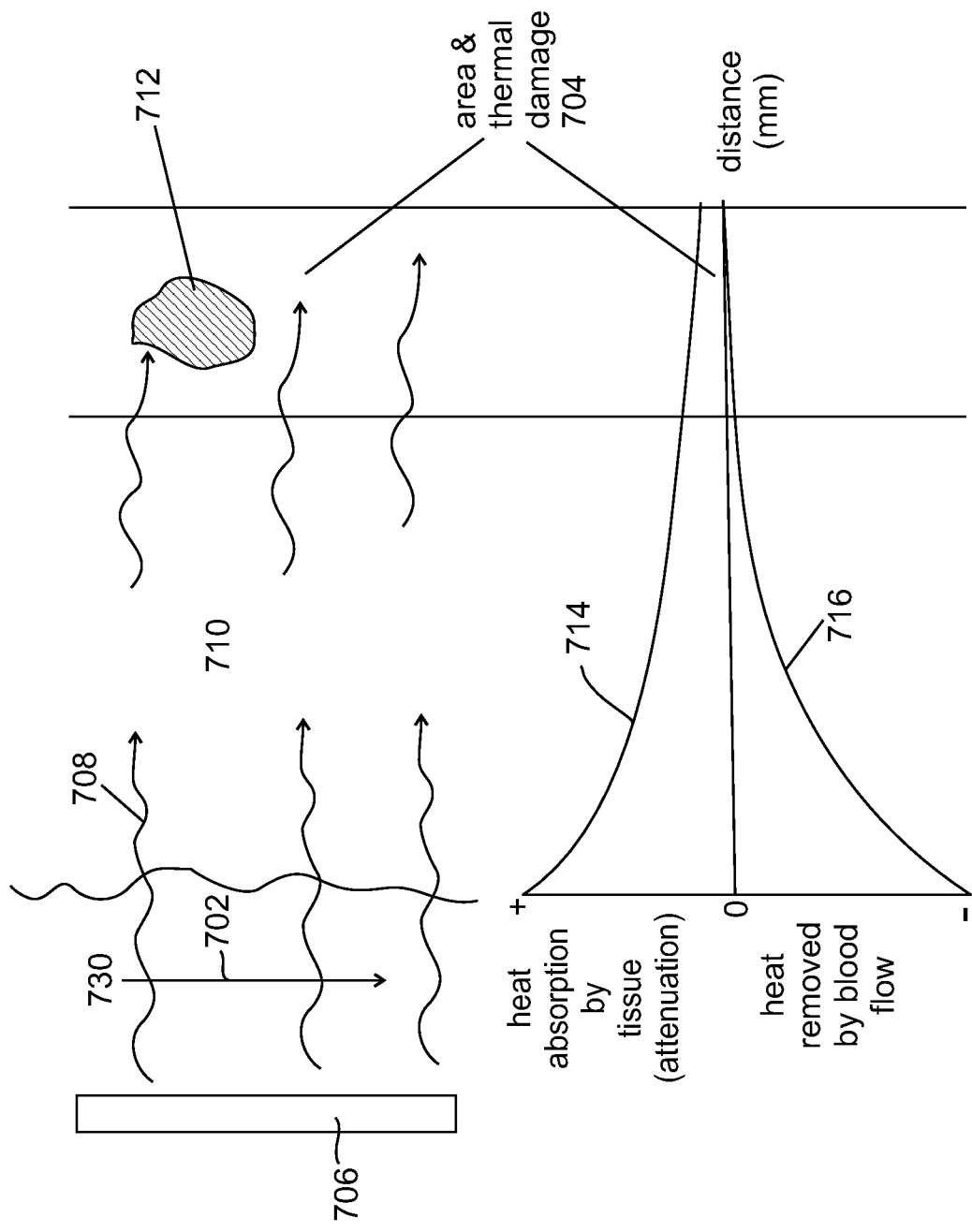
Figure 7B:
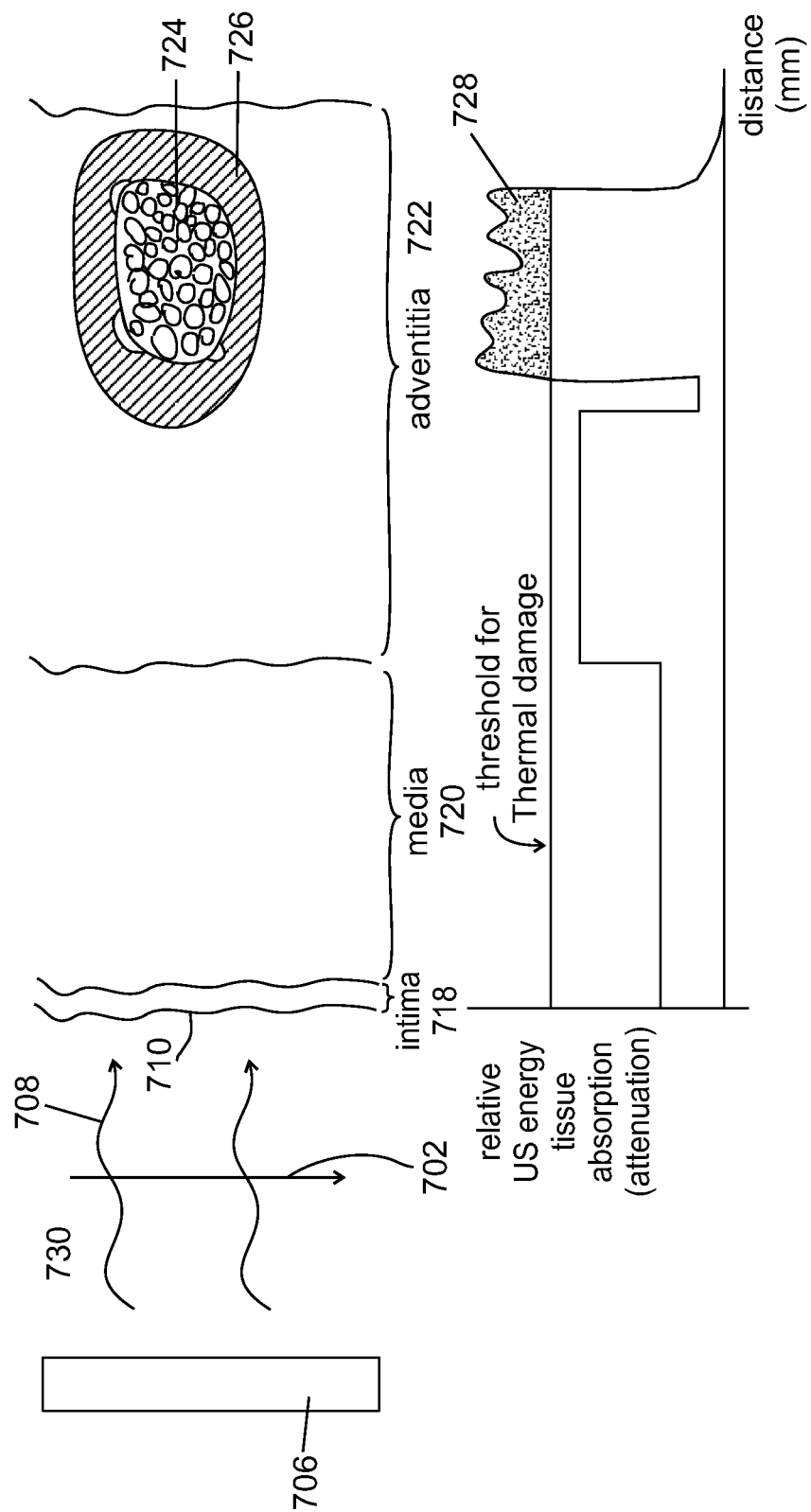
Figure 7C:
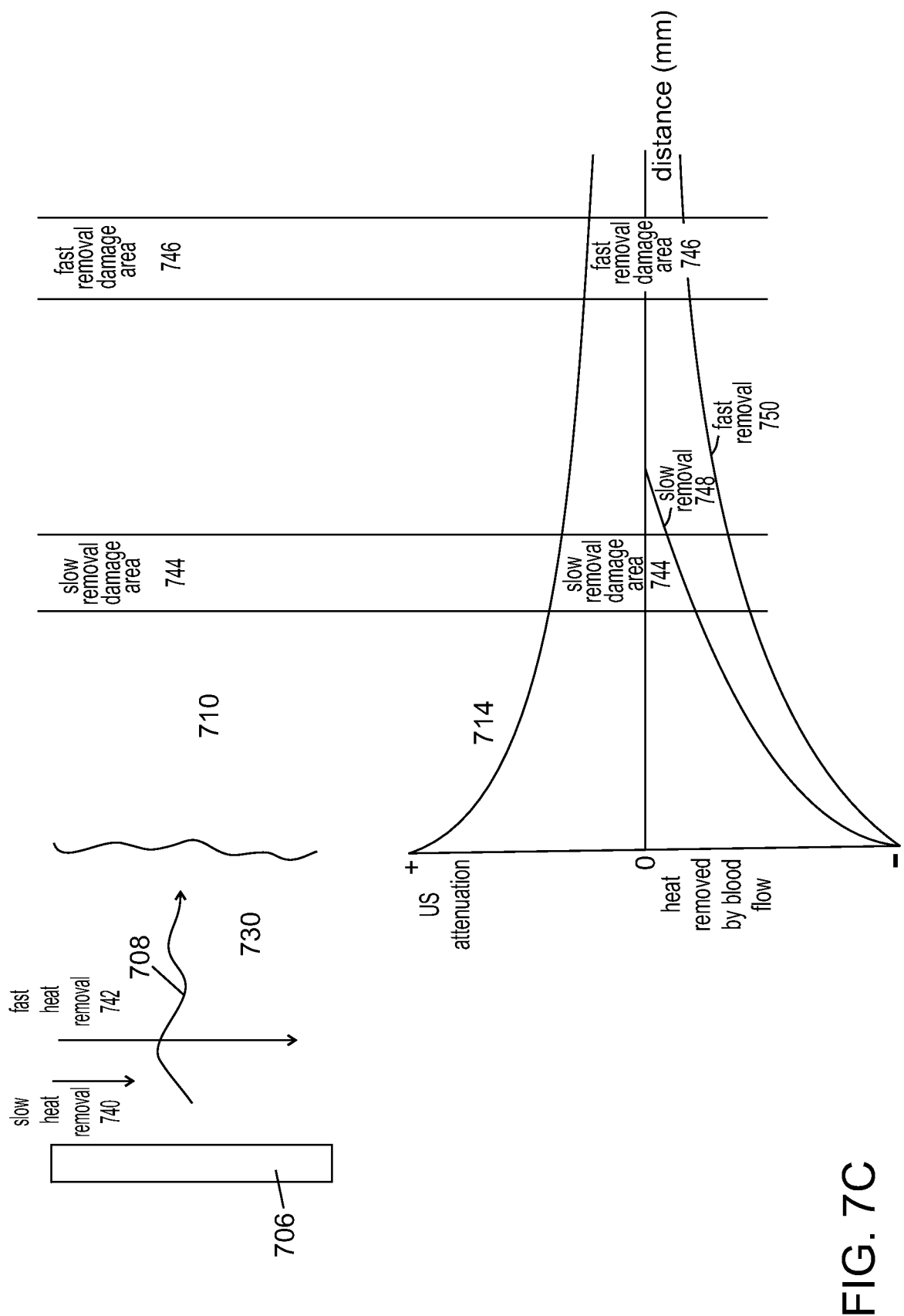
Figure 7D:
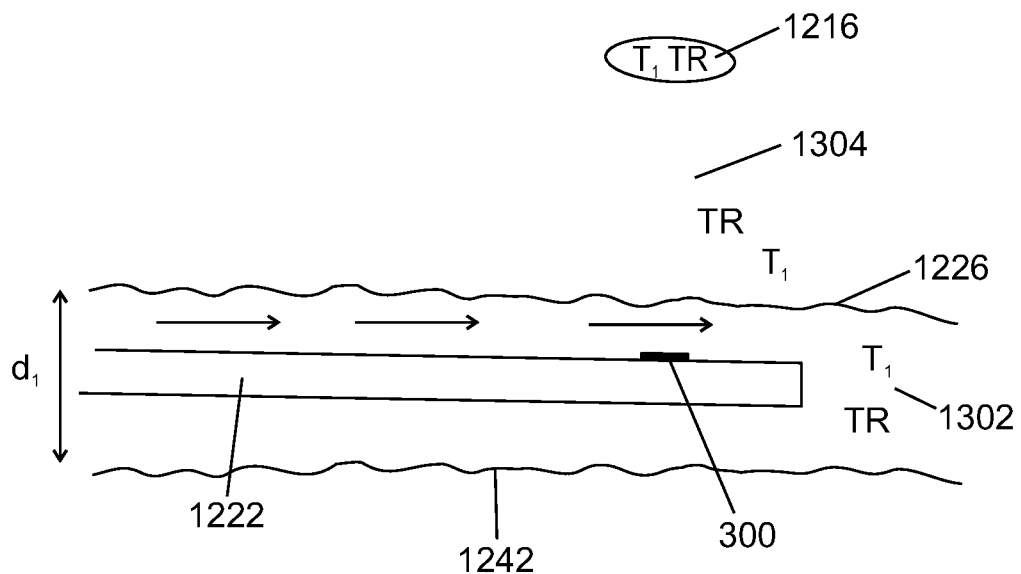
Figure 7E:
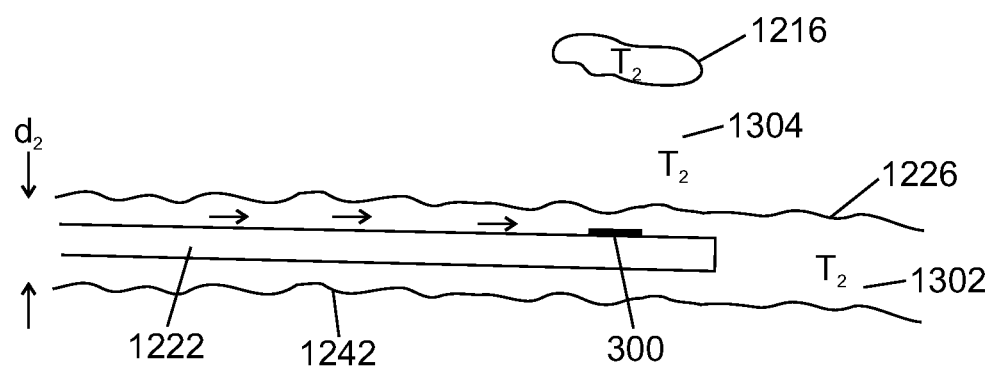
Figure 8:
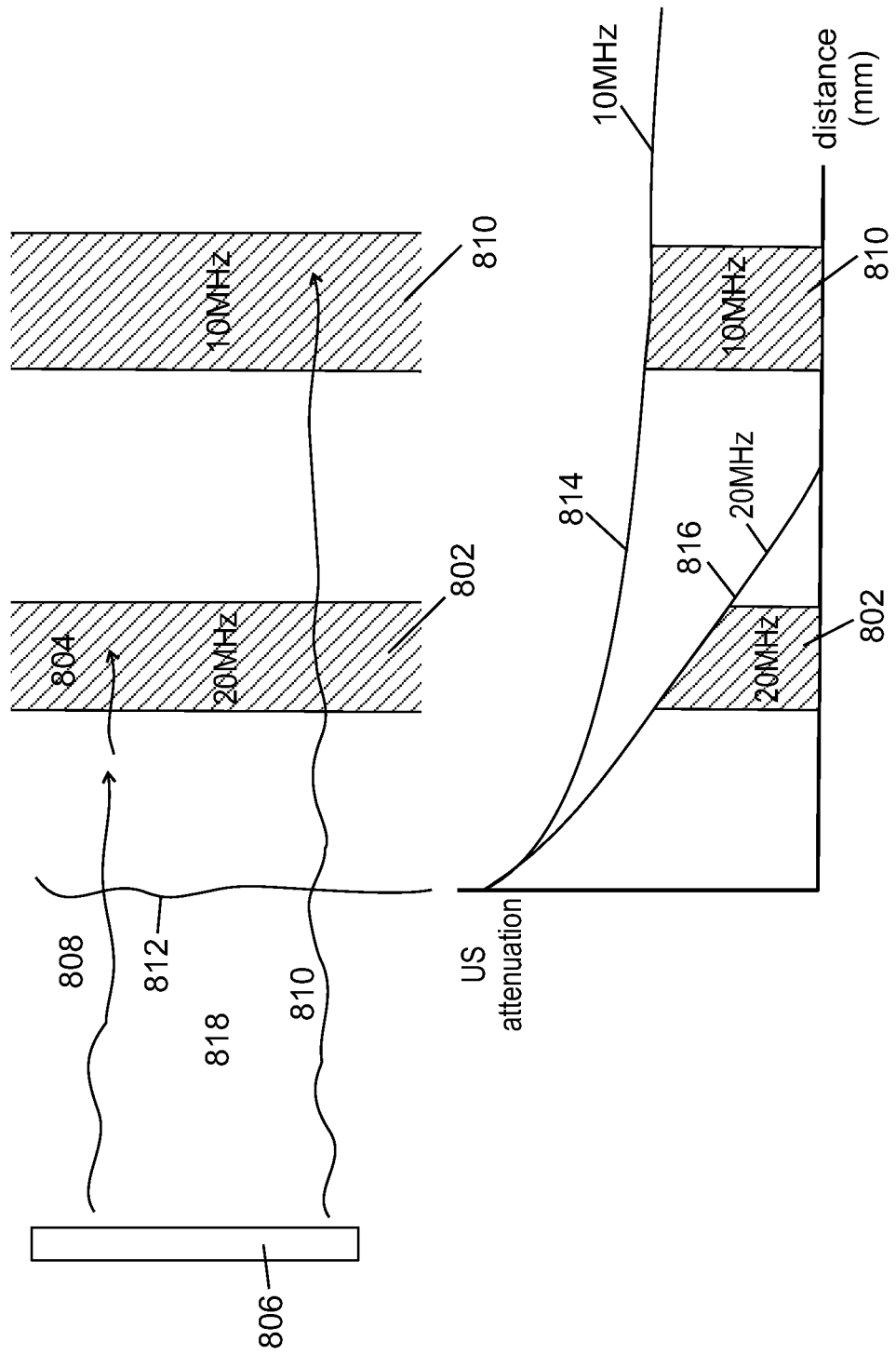
Figure 9:
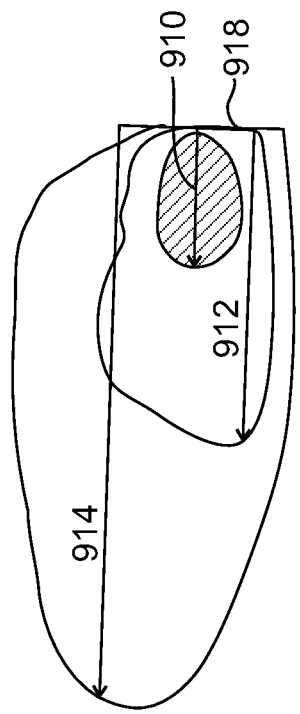
Figure 9:
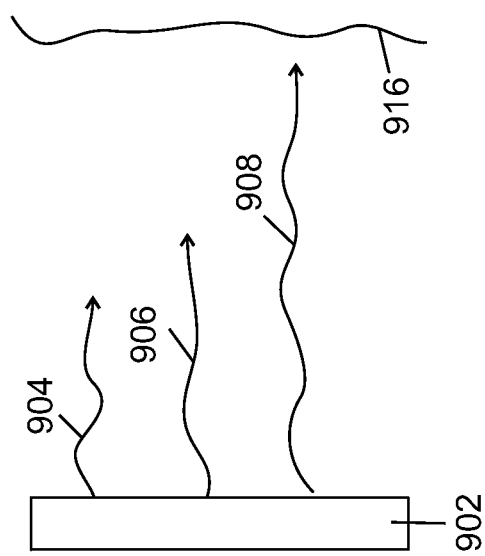
Figure 10:
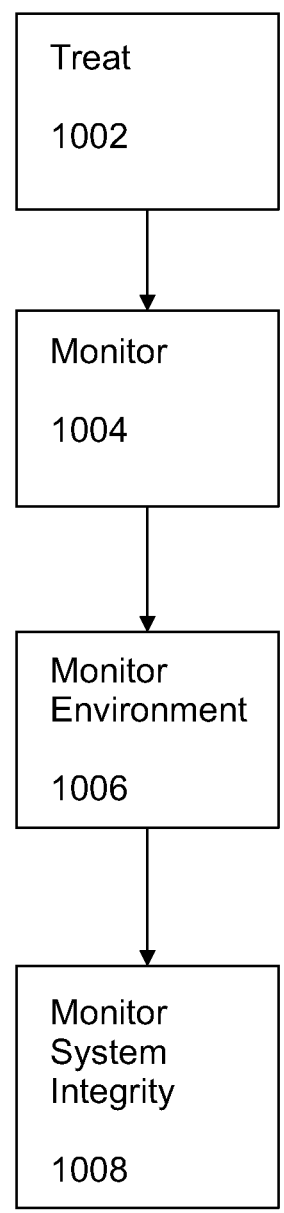
Figure 11:
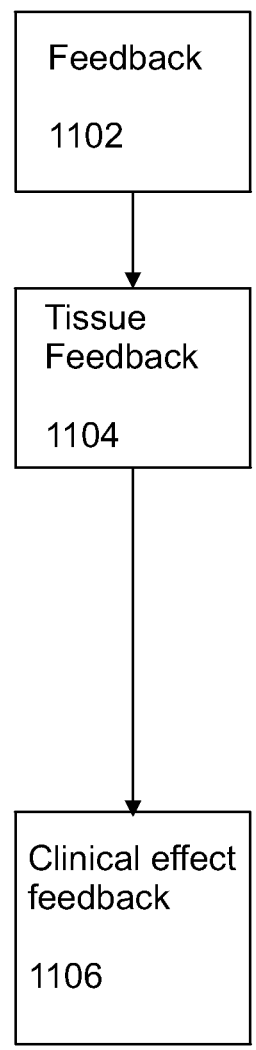
Figure 12D:
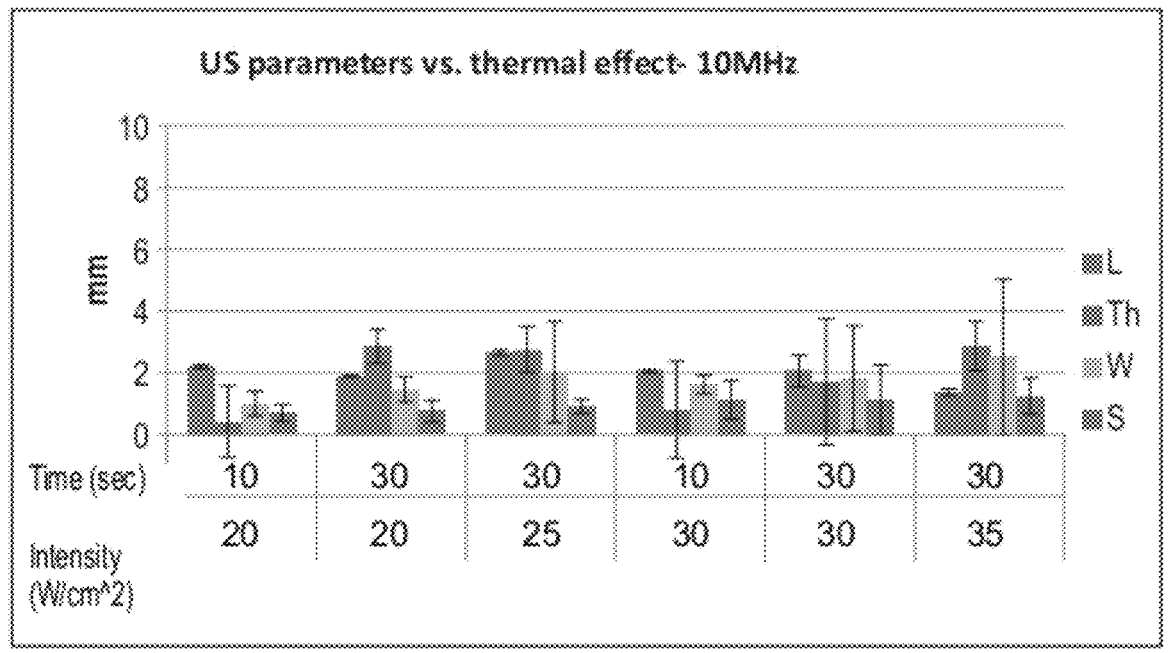
Figure 12D:
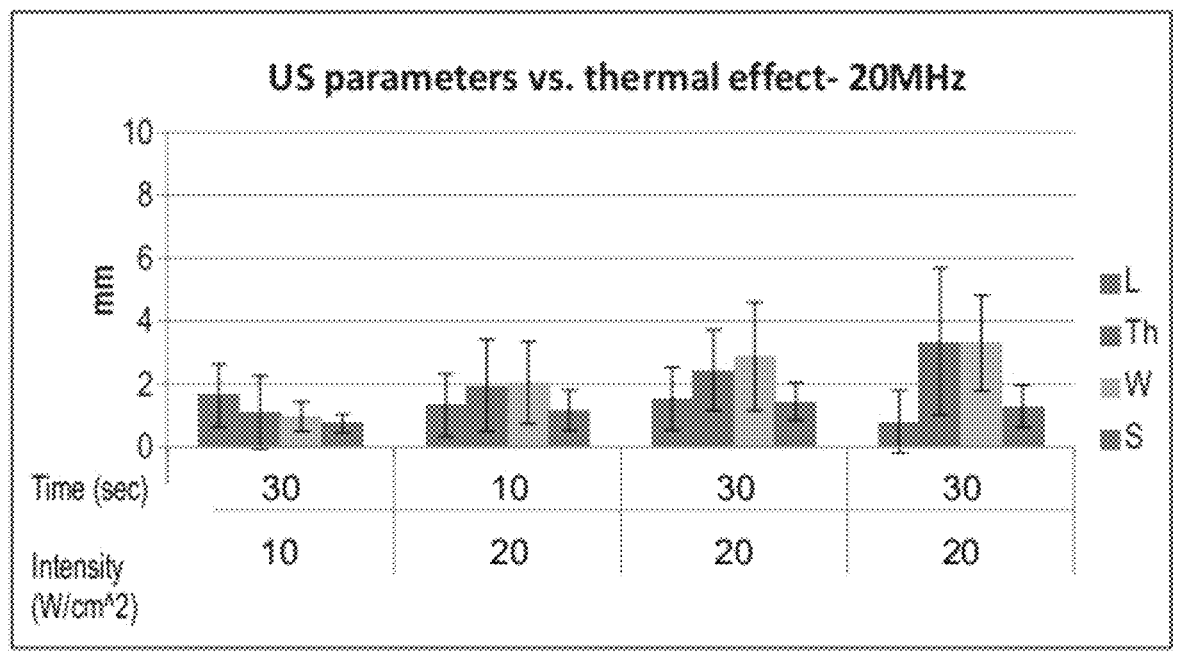
Figure 12E:
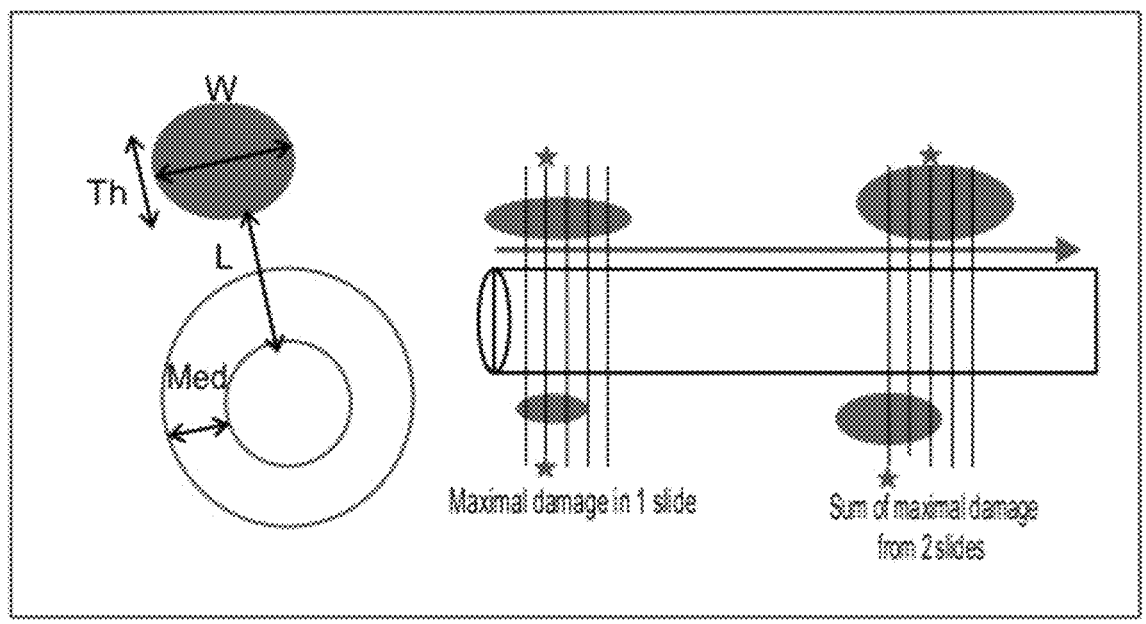
Figure 13A:
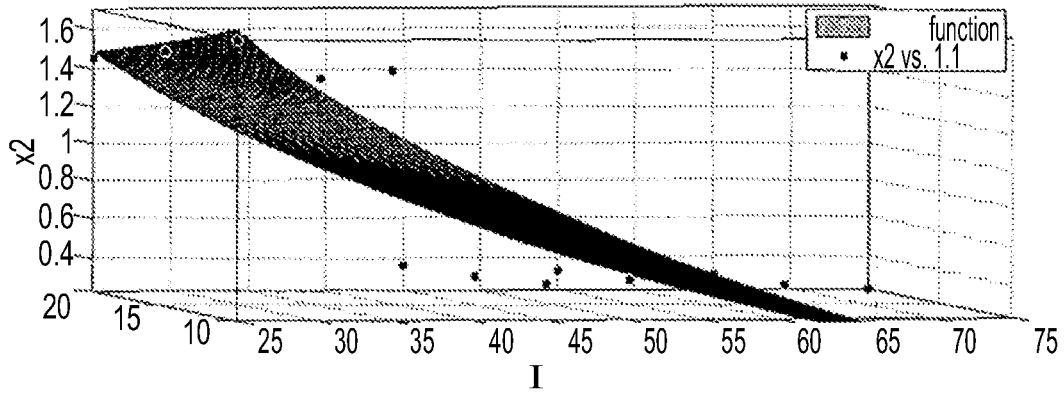
Figure 13B:
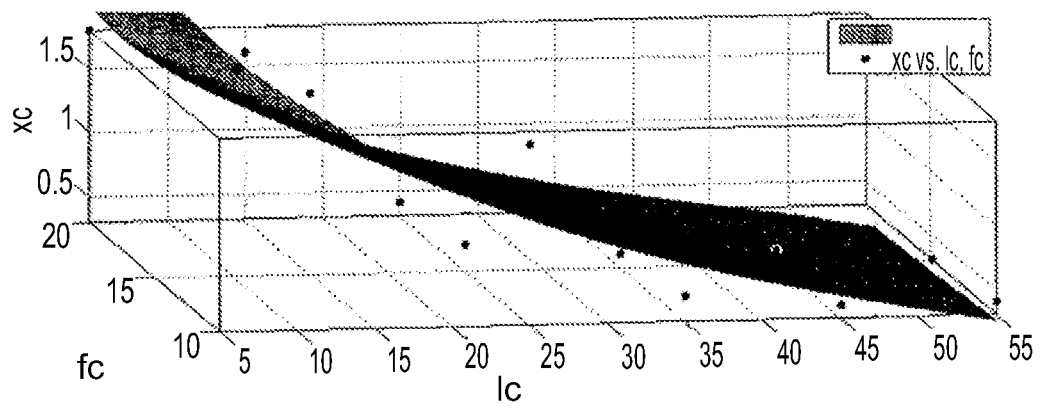
Figure 13C:
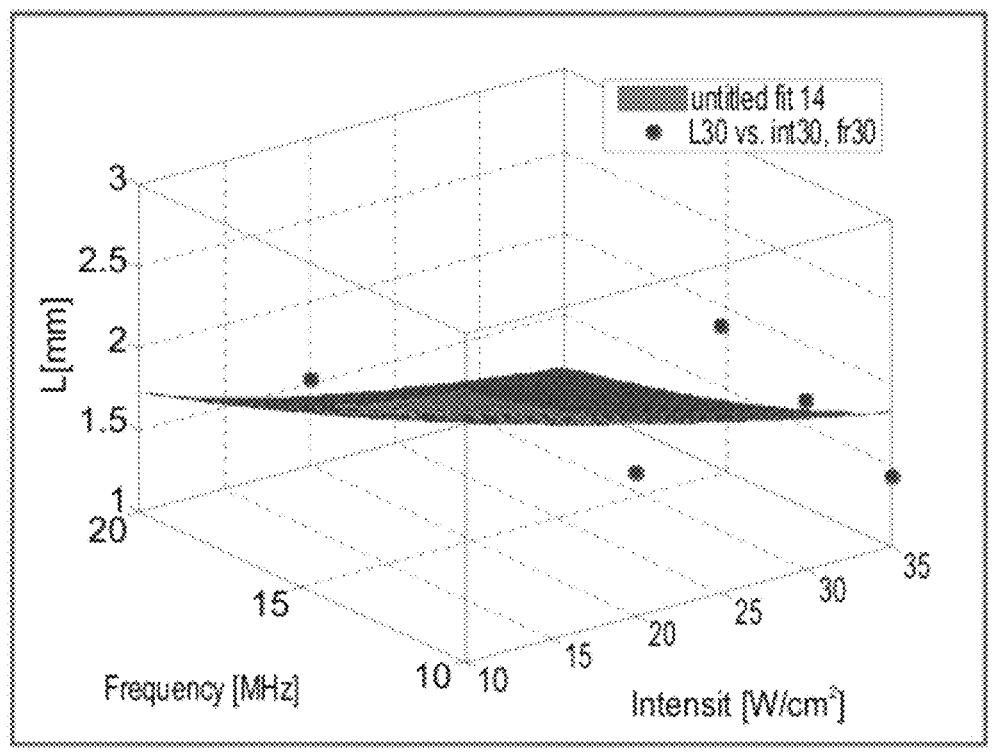
Figure 13D:
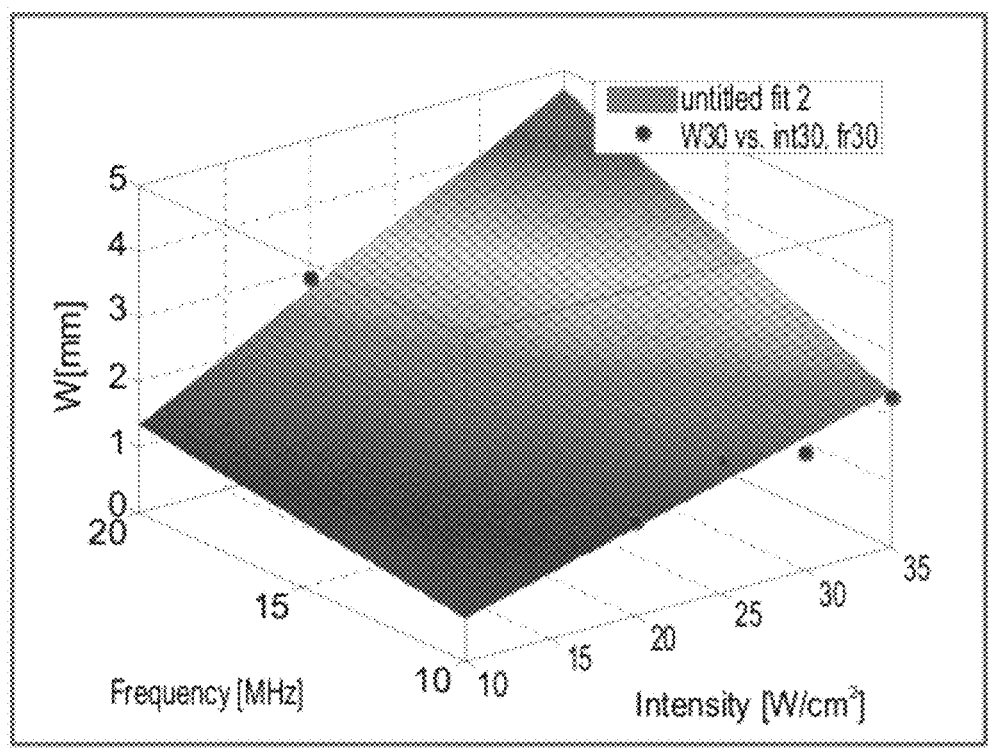
Figure 13E:
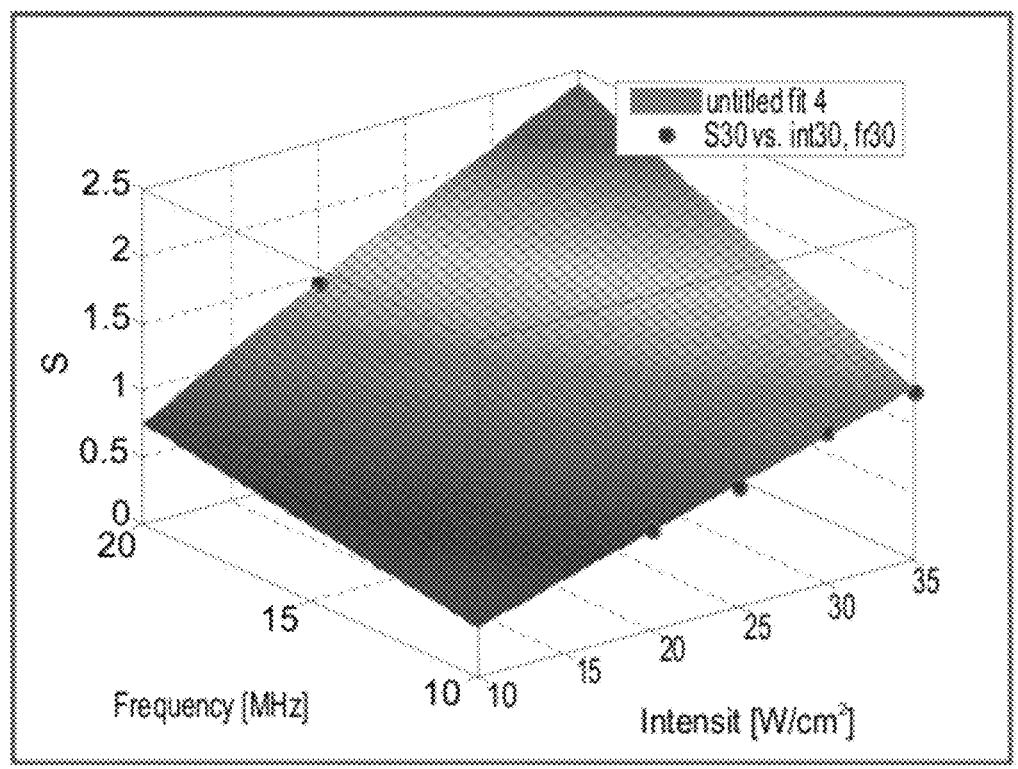
Figure 13F:
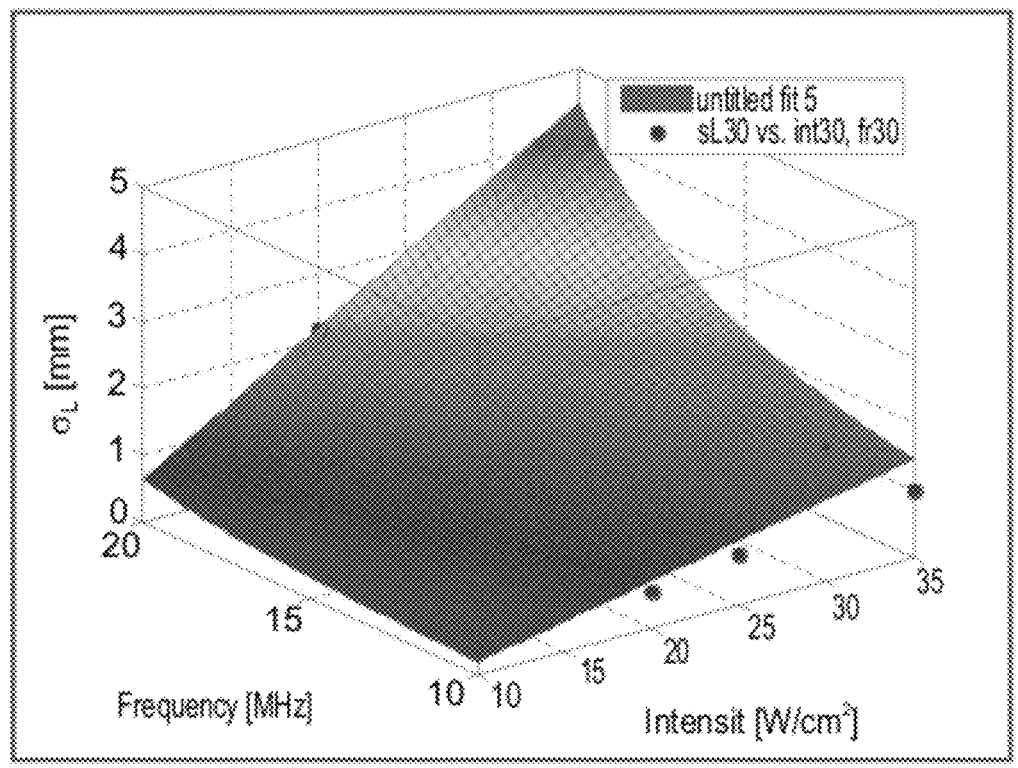
Figure 13G:
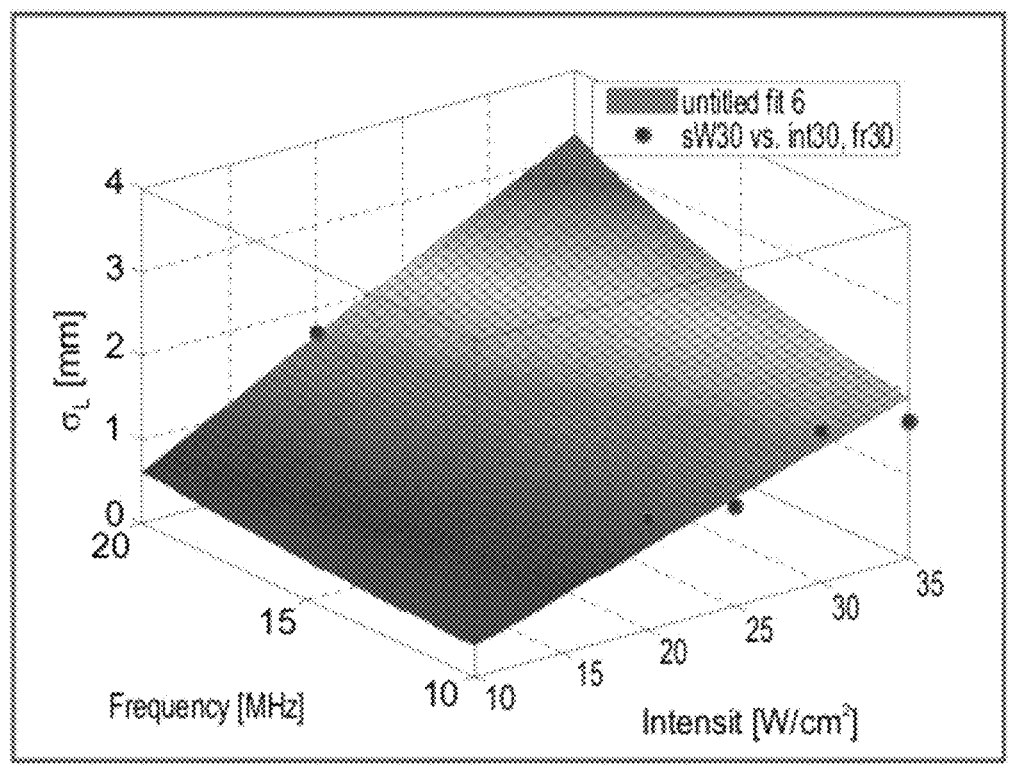
Figure 13H:
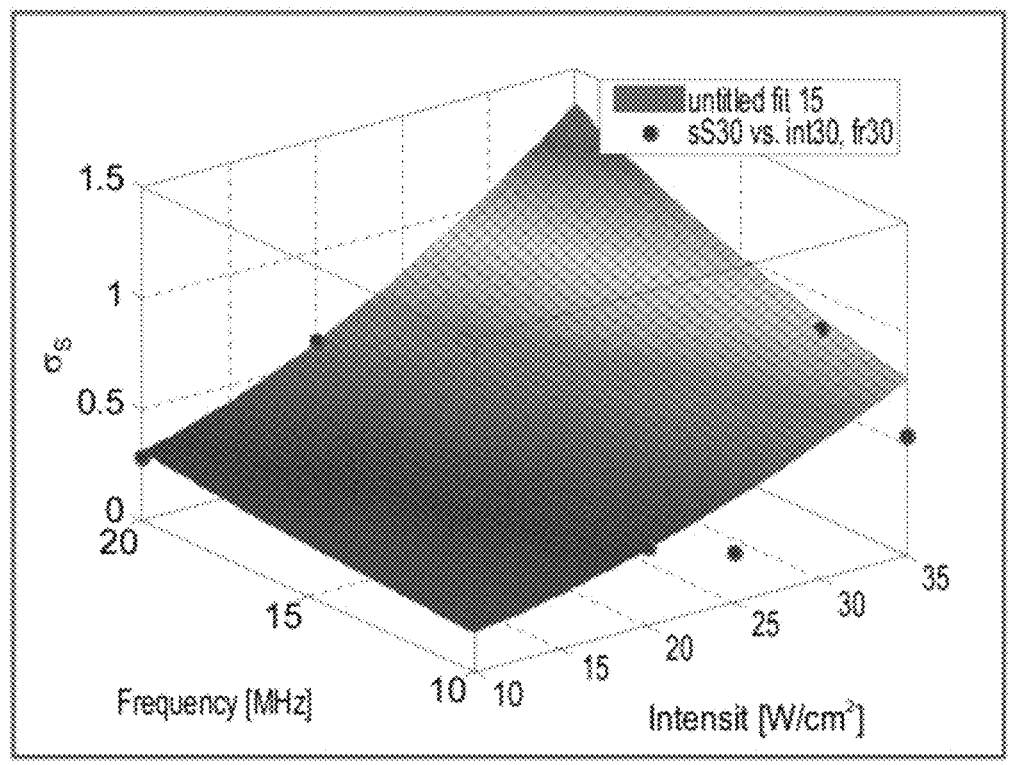
Figure 14A:
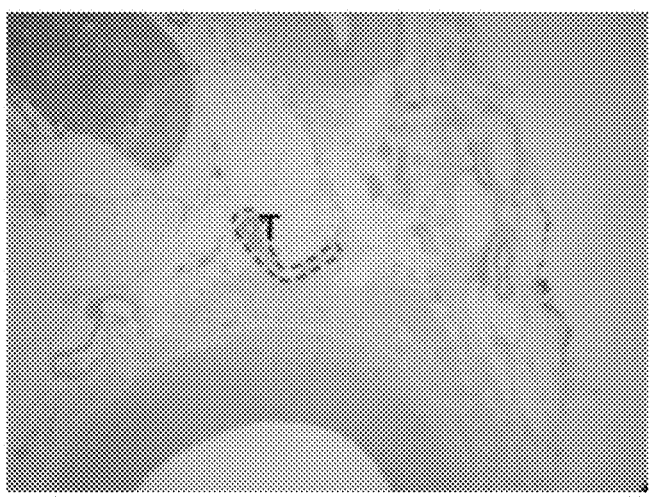
Figure 14B:
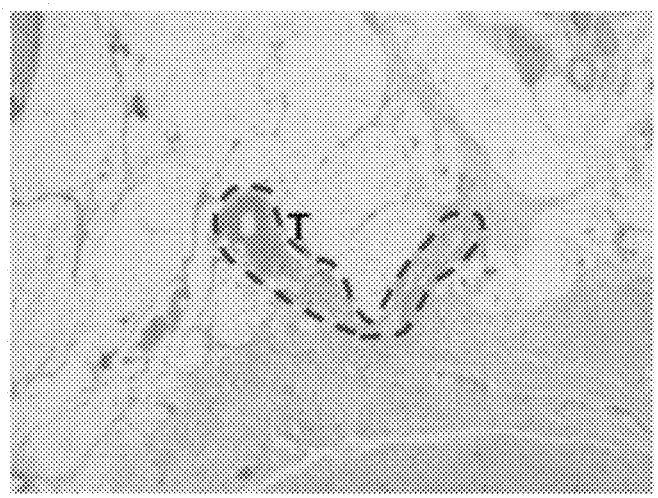
Figure 14C:
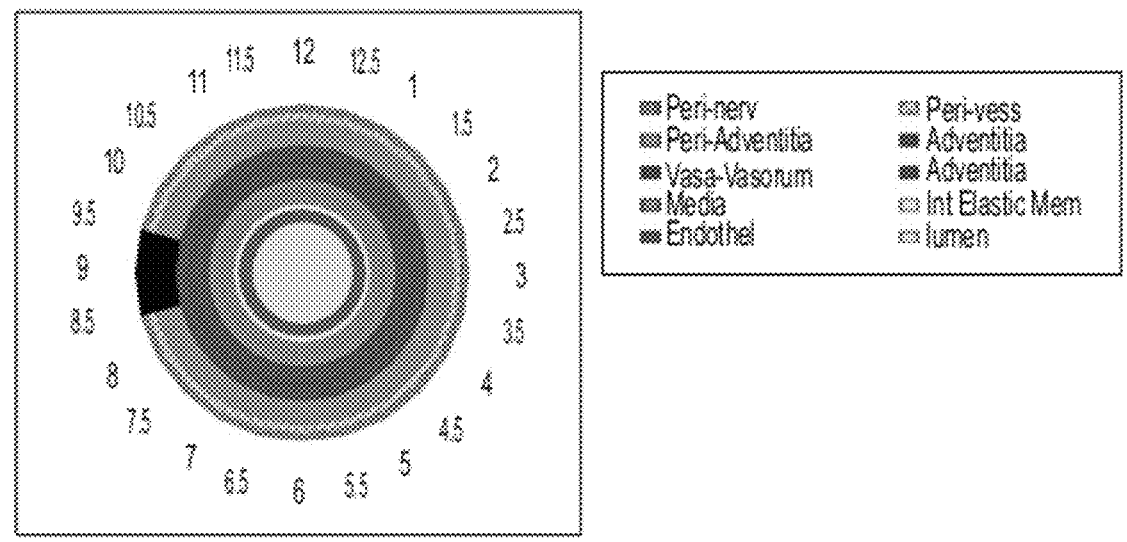
Figure 16A:
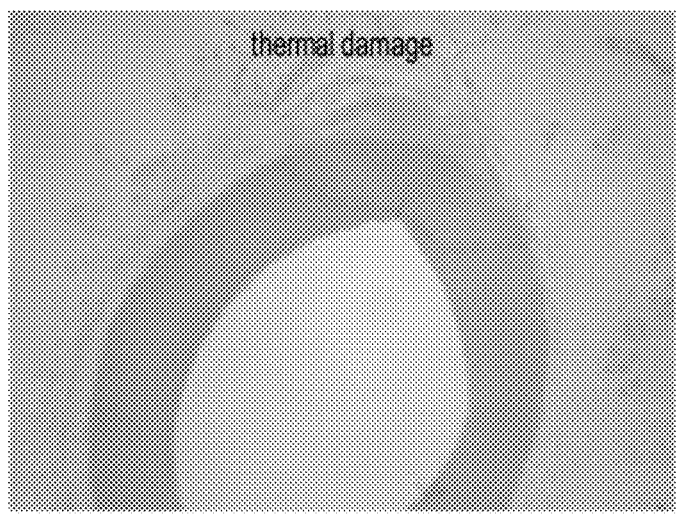
Figure 16B:
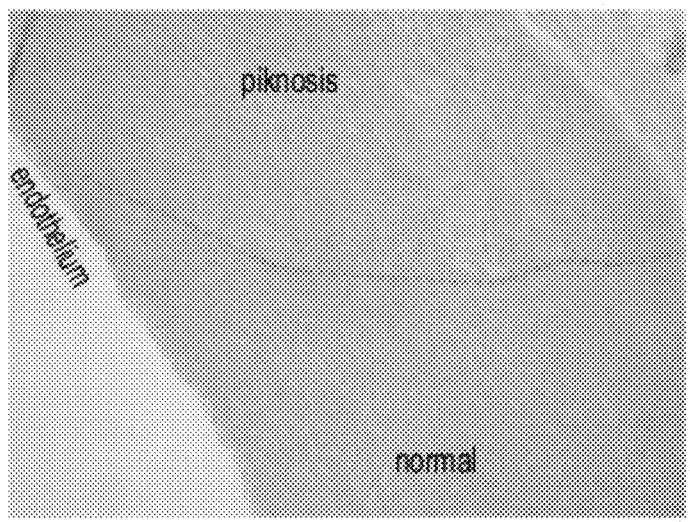
Figure 16C:
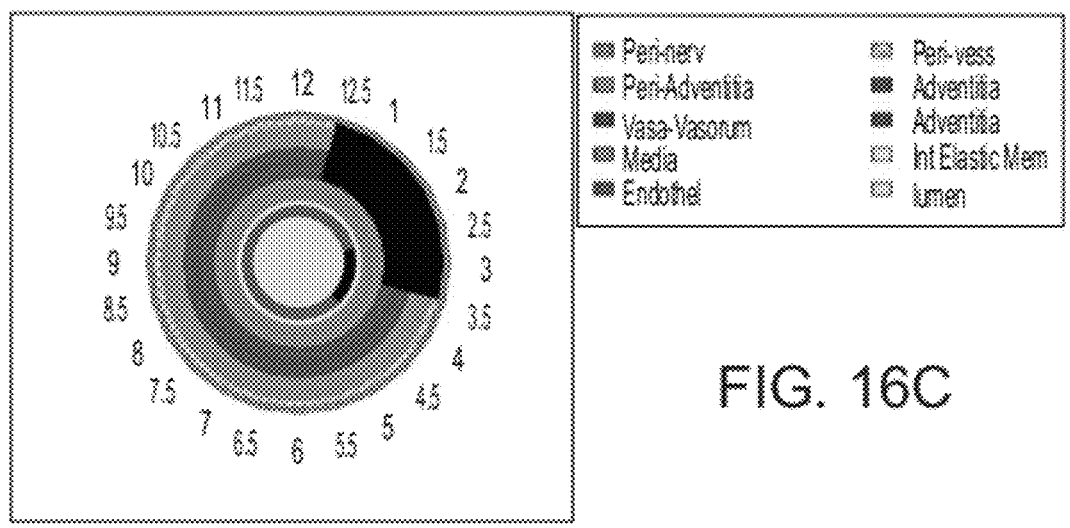
Figure 17A:
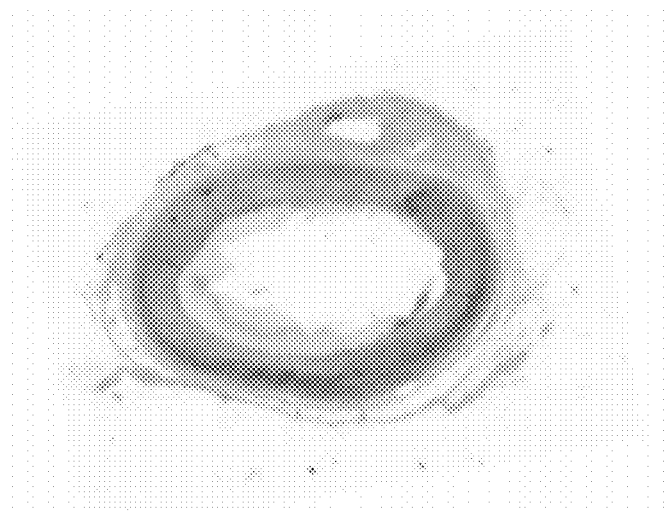
Figure 17B:
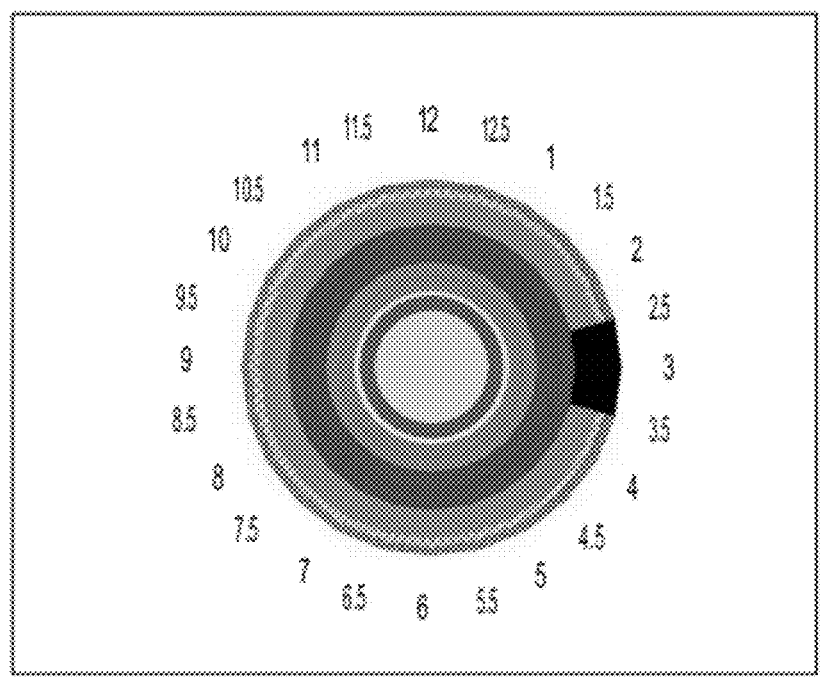
Figure 17B:
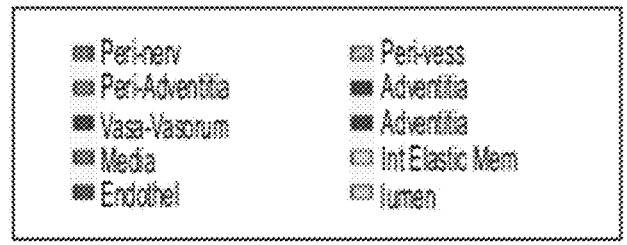
Figure 21:
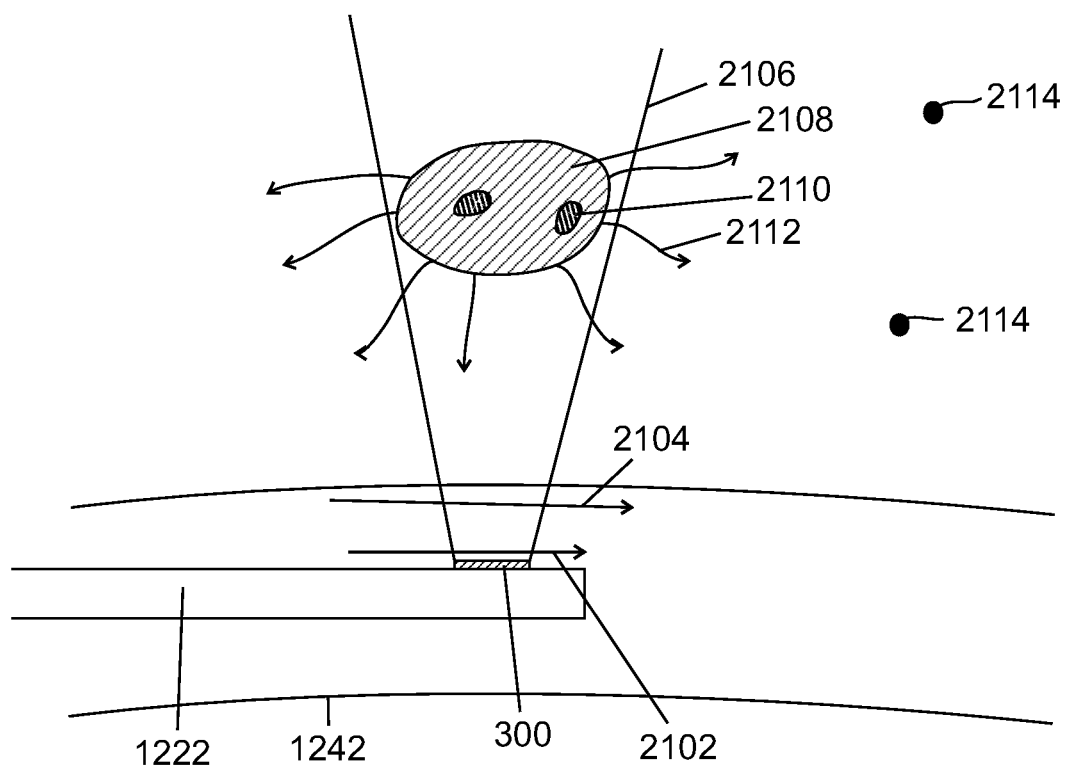
Figure 22:
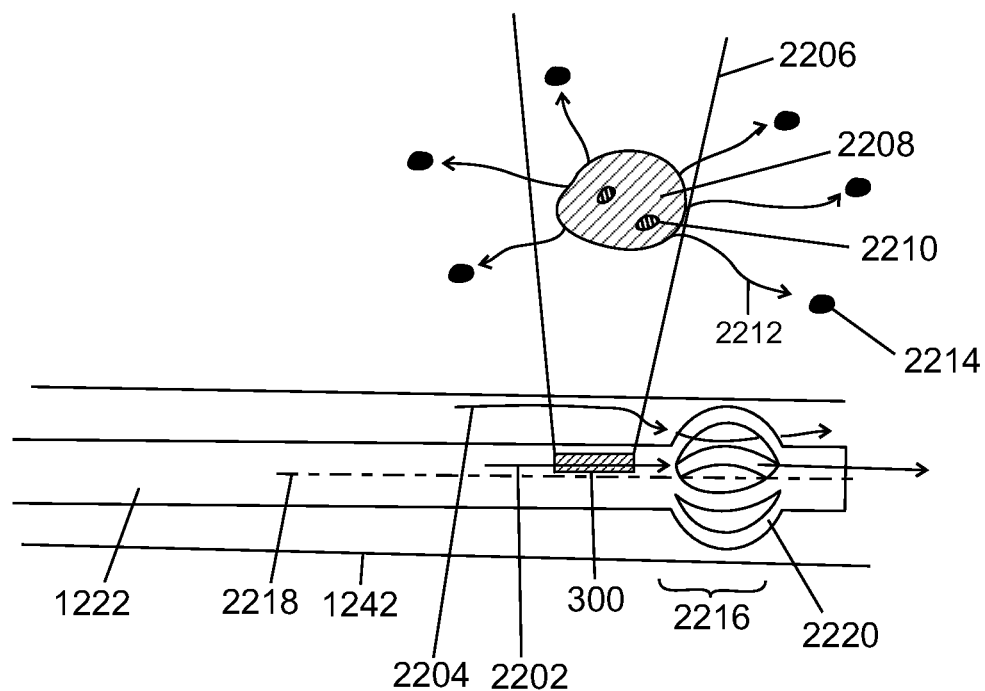
Figure 23:
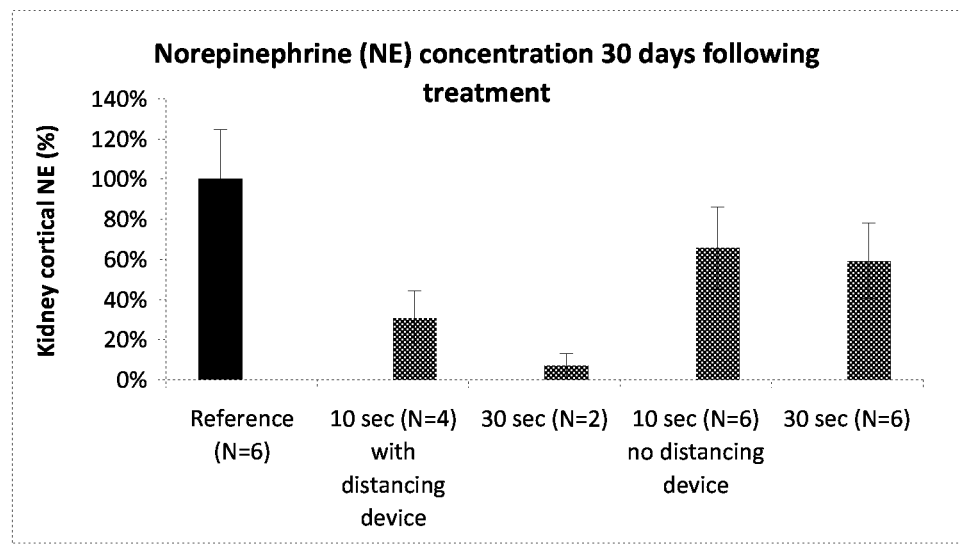
Figure 24A:
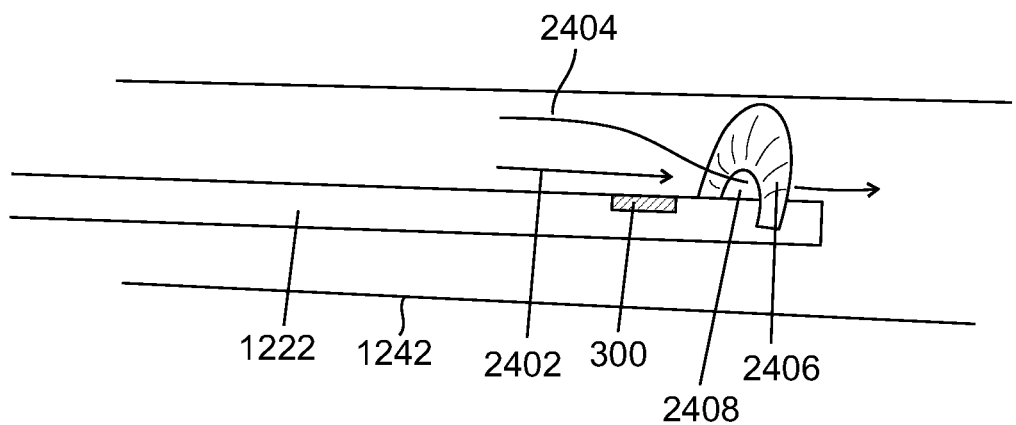
Figure 24B:
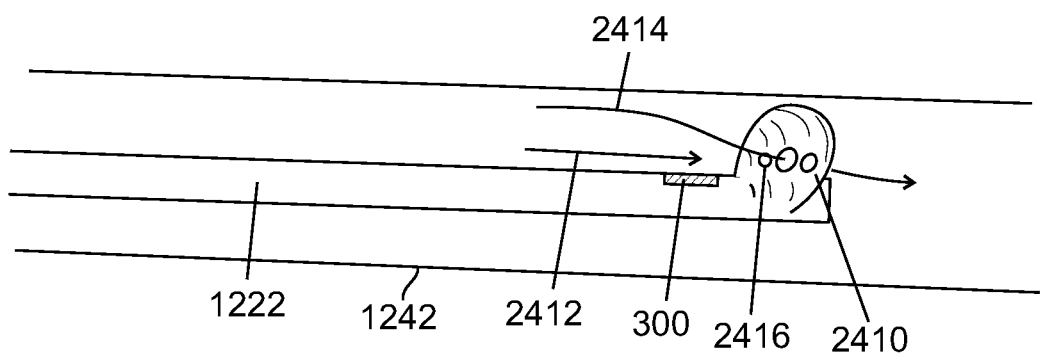
Figure 24C:
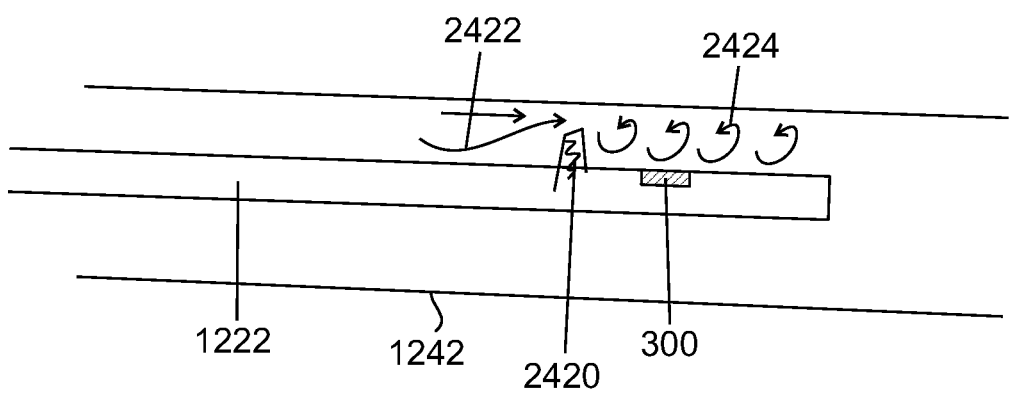

FIGS. 7D-7E illustrate the adjustment of one or more tissue properties, in accordance with some embodiments of the invention;

FIG. 8 is an exemplary graph illustrating some associations between frequency and treatment, useful in practicing some embodiments of the invention;

FIG. 9 is an exemplary graph illustrating some associations between ultrasound intensity profile and treatment, useful in practicing some embodiments of the invention;

FIG. 10 is a flow chart of monitoring during treatment, in accordance with an exemplary embodiment of the invention;

FIG. 11 is a flow chart of feedback during treatment, in accordance with an exemplary embodiment of the invention;

FIG. 12A is a table summarizing experimental results obtained using some embodiments of the invention;

FIG. 12B is a table summarizing experimental results at 10 Mhz, obtained using some embodiments of the invention;

FIG. 12C is a table summarizing experimental results at 20 Mhz, obtained using some embodiments of the invention;

FIG. 12D illustrates graphs summarizing the values in FIGS. 12B-12C, useful in practicing some embodiments of the invention;

FIG. 12E is an image illustrating the variables described in FIGS. 12B-12D, useful in practicing some embodiments of the invention;

FIGS. 13A-B are graphs of associations between tissue damage results and ultrasound parameters according to the results of FIG. 12A, useful in practicing using some embodiments of the invention;

FIGS. 13C-H are exemplary graphs of tissue damage results and ultrasound parameters according to the results as shown in FIGS. 12B-12D, useful in practicing some embodiments of the invention;

FIGS. 14A-C are images of experimental results in the aorta obtained using some embodiments of the invention;

FIGS. 15A-D are images of experimental results in the aorta obtained using some embodiments of the invention;

FIGS. 16A-C are images of experimental results in the carotid artery obtained using some embodiments of the invention;

FIGS. 17A-B are images of experimental results in the carotid artery obtained using some embodiments of the invention;

FIGS. 18A-G are images of experimental results in the renal artery obtained using some embodiments of the invention;

FIGS. 19A-C are images of experimental results in the renal artery obtained using some embodiments of the invention;

FIGS. 20A-J are images of experimental results in the renal artery obtained using some embodiments of the invention;

FIG. 21 is a schematic showing the formation of time insensitive treatment regions, in accordance with an exemplary embodiment of the invention;

FIG. 22 is a schematic showing selectively treating nerves outside the region of tissue damage and/or outside the US beam, in accordance with an exemplary embodiment of the invention;

FIG. 23 is a graph of experimental results obtained using some embodiments of the invention; and FIGS. 24A-C are schematics of some examples of a blood flow control element, in accordance with an exemplary embodiment of the invention.

DESCRIPTION OF SPECIFIC EMBODIMENTS
OF THE INVENTION

The present invention, in some embodiments thereof, relates to a method of treatment of tissue and, more particularly, but not exclusively, to a method of selectively targeting and treating tissue using unfocused ultrasound energy. In an exemplary embodiment of the invention, the tissue is in a mammal, for example, a pig or a human.

An aspect of some embodiments of the invention relates to a method of selectively treating tissue using ultrasound energy delivered intrabody. Optionally, the ultrasound energy is non-focused.

In an exemplary embodiment of the invention, tissues can be targeted spatially, for example, a volume of tissue located in a wall of a blood vessel. Optionally, the tissue to be targeted is defined spatially, for example, using x,y,z coordinates.

In an exemplary embodiment of the invention, target tissues are treated with ultrasound energy, for example, heated using ultrasound energy. Optionally, tissues are damaged, for example, thermally damage, not necessarily limiting examples of damage include; burning, coagulation, denaturation, ablation, necrosis, disruption (e.g., of signal propagation in nerves), degeneration, destruction. Optionally or additionally, tissues are heated sufficiently without causing immediate damage and/or shrinkage.

In an exemplary embodiment of the invention, target tissues are heated to a selected temperature. For example, about 43, 45, 50, 55, 60, 65, 70, 80, 85, 90, 95 degrees Celsius, or other smaller, intermediate or larger temperatures are used, or subranges thereof.

In an exemplary embodiment of the invention, the time to reach the peak temperature is selected. For example, about 0.1 seconds, about 1 second, about 3 seconds, about 5 seconds, about 10 seconds, about 15 seconds, about 30 seconds, or other smaller, intermediate or larger values are used.

In an exemplary embodiment of the invention, the acoustic intensity profile is high intensity, for example, about 11-20, or 21-30 or 31-40, or 41-50 or 51-60 or 61-70 or >=71 Watt/square centimeter, or other smaller, intermediate or larger values are used.

In an exemplary embodiment of the invention, the initial treatment region is selected to start away from the intima of the artery, for example, about 0.2 mm away from the intima, or 0.3 mm, 0.5 mm, 1 mm, 2 mm, 3 mm, 4 mm, 5 mm, 7 mm, away, or other smaller, intermediate or larger distances are selected.

In an exemplary embodiment of the invention, the location, the volume and/or the extent of the treatment region is selected.

In an exemplary embodiment of the invention, the treatment is selected to treat only a portion of the target tissue, for example, half of the target tissue. Alternatively, the treatment is selected to treat the entire target tissue.

In an exemplary embodiment of the invention, the treatment is selected according to safety considerations. Optionally, a safety consideration is treating with a margin of safety around the target tissue, for example, the treatment is selected to treat the target tissue without treating surrounding tissue. Alternatively, the treatment is selected to treat at least some tissue surrounding the target tissue. Alternatively or additionally, a safety consideration is side effects of treatment, for example, treatment is selected to reduce and/or prevent contraction (e.g., stenosis) of the artery, for example, due to scarring of tissue in the arterial wall.

In an exemplary embodiment of the invention, the treated is selected for a type of tissue. Optionally, the treatment is selected towards nerves in the adventia or peri-adventitia. Optionally or additionally, the treated is selected towards nerves are in the renal artery wall. Alternatively, the treatment is selected towards renal nerves in the aorta. Alternatively, the treatment is selected towards nerves in the carotid artery wall.

In an exemplary embodiment of the invention, the treatment is selected by taking into account the cooling capacity of the vessel wall, such as a blood flow in the artery.

In an exemplary embodiment of the invention, the frequency of vibration of the acoustic element of the transducer is selected according to the depth of the target tissue.

In an exemplary embodiment of the invention, the ultrasonic intensity profile is selected according to the size of the treatment region. Optionally, a relatively low ultrasonic intensity profile treats a relatively small area in the peri-adventitia. Optionally, a relatively higher ultrasonic intensity profile is selected to increase the treatment region from the peri-adventitia towards the intima, for example until the adventia, until the media, or to increase the size of the treatment region in the peri-adventia.

In an exemplary embodiment of the invention, one or more tissue properties are adjusted, for example, increased and/or decreased. Non-limiting examples of tissues include; target tissue, surrounding tissue, blood flowing in vessel. Optionally, tissue properties are adjusted in accordance with the selected effect (e.g., thermal effect), for example, to relatively increase the size of the treated area. Optionally or additionally, tissue properties are adjusted in accordance with the selected safety parameters, for example, to relatively increase the margin of safety. Non-limiting examples of tissues properties that are adjusted include; the temperature of the tissue, the heat removal rate from the tissue, the acoustic energy absorption of the tissue.

In an exemplary embodiment of the invention, feedback associated with the treatment is obtained. Optionally, the desired result is used as a target, such as in an open-loop manner. For example, initial parameters are set and the tissue is treated to achieve the result. Alternatively or additionally, the desired result is used as feedback of the treatment, such as in a close-loop manner. For example, treatment is applied, imaging of the treatment region is performed to check if the desired result has been met and treatment is reapplied, optionally with adjustments to the treatment.

In an exemplary embodiment of the invention, the treatment region is defined by a circumferential extent and by a distance extent and also by a starting distance (e.g., from an intima). In an exemplary embodiment of the invention, the distance extent and/or starting distance are controlled with an accuracy of, for example, better than 2 mm, 1 mm, 0.5 mm, or 0.2 mm. Optionally or alternatively, the circumferential extent of treatment is controlled with an accuracy of better than 30 degrees, 10 degrees, or 5 degrees, which can be, for example, 3 mm, 2 mm, 1 mm, 0.5 mm or better or intermediate accuracy.

In an exemplary embodiment of the invention, the amount, pattern and/or extent of the treated region is selected according to a desired effect and/or a probability of affecting sufficient tissue to be treated (e.g., nerves). Optionally, the amount of treatment is curtailed, for example, to reduce side effects, such as constriction of the lumen caused by too much damage in the lumen wall.

In an exemplary embodiment of the invention, the percent of tissue damaged within the treatment region is selected. Optionally, within the treatment region, some areas of tissues are damaged and some areas of tissues are not damaged. Optionally, the treatment region comprises the smallest area of tissue that can be enclosed (e.g., by drawing a circle on the histology image) in which damage regions created during one treatment are contained (e.g., damage visible on the histology image).

In an exemplary embodiment of the invention, the estimated percentage of damage is selected to be, for example, about 0-20%, about 20%-60%, about 60%-100%, or about 80%-100%, or about 60%-80%, or about 0-60%, or about 90%-100%, or about 80-90%, or about 70%-80%, or other smaller, intermediate or larger ranges are used. Optionally, the estimated percent does not include nerve tissue, but includes, for example, collagen. Optionally, the damage type is selected, for example, as described herein (e.g., denaturation of collage).

In an exemplary embodiment of the invention, for a section of treated lumen of, for example, 1-5 cm in length (e.g., axial distance between outermost treatment locations), the percentage of axial locations treated is, for example, 10%, 30%, 50%, 80% or smaller or intermediate or greater percentages.

In an exemplary embodiment of the invention, when considering the surface area of the intima of such a treated section, and mapping treated regions by "collapsing" them towards the intima, the percentage of area treated can be, for example, 5%, 15%, 30%, 60%, 80% or smaller or intermediate or larger percentages.

In an exemplary embodiment of the invention, when considering the circumference of the intima of such a treated section at an axial location where treatment is applied, and mapping treated regions by "collapsing" them towards the intima, the percentage of circumference treated can be, for example, 5%, 15%, 30%, 60%, 80% or smaller or intermediate or larger percentages, for example, for between 1 and 8 axial treatment locations.

A particular feature of some embodiments of the invention is that an extent of treatment in a dimension perpendicular to the lumen wall is affected both by cooling of the lumen wall, e.g., by natural blood flow and by dissipation of energy as the energy penetrates into the tissue. In an exemplary embodiment of the invention, the frequency and/or other properties of the energy affect the absorption per unit distance, which results in reduced energy deposition as distance increases. Optionally or alternatively, cooling effects of nearby tissue reduce energy deposition. Optionally or alternatively, divergence of the beam reduces energy deposition. Optionally or alternatively, tissue properties, for example, insulation of a sheath surrounding nerves, serves to increase the effect of energy deposition at some tissues. Optionally or alternatively, tissue characteristics affect energy deposition thereat.

A particular feature of some embodiments of the invention is the use of an unfocused energy field, which, in some embodiments, can preserve a uniform definition of its edges for a considerable distance, thereby providing definition of circumferential edges of a treated area.

A particular feature of some embodiments of the invention relates to the ability to reduce mechanical positioning requirements while maintaining and/or increasing accuracy of spatial selectivity of treatment.

With respect to a direction perpendicular to the vessel wall, in a focused system, position control is provided by accurate focusing and control of catheter position (e.g., to be in contact with a wall). In an exemplary embodiment of the invention, however, position control in that direction is provided by a tradeoff between cooling by blood flow and energy application. This is not dependent on the catheter position in a blood flow, as there is relatively little loss in the blood, in some embodiments. This means that variations of several millimeters in catheter distance form the wall need not have a significant effect on spatial treatment location. Moreover, not having contact with the vessel wall can ensure, in some embodiments, sufficient cooling to prevent damage at any part of the intima.

Use of non-focused beams can also help in the circumferential accuracy requirements. In one example, it allows the treated "spot" to be quite large, which means there need not be any scanning of a focal point of a focused beam, which scanning may be complex and/or inaccurate. Optionally, the circumferential profile of the beam is selected so that it provides a gradual cut-off in degree of damage, for example, along a border of, for example, 1-2 mm in width. Alternatively, a sharp cut-off is provided, for example, by suitable selection of emitter design to have a sharp cut-off in intensity profile.

In an exemplary embodiment of the invention, provision of high power allows the treatment time to be short enough so that, for example, treatment can be applied while blood velocity is constant (e.g., during cardiac diastole) and/or while the vessel wall is not moving (e.g., relative to catheter, which is optionally determined using a distance sensor and/or estimated using a pulse sensor and/or ECG sensor).

In an exemplary embodiment of the invention, cooling of an ultrasonic emitter by blood flow allows higher power to be used.

An aspect of some embodiments of the invention relates to a method of forming an area of tissue damage in the wall and/or tissue surrounding a lumen (e.g., artery) in a time insensitive manner. In an exemplary embodiment of the invention, energy (e.g., unfocused US) emitted at the arterial wall for any amount of time falling over a threshold value produces substantially the same tissue damage region (e.g., damage as seen on histological examination, and/or damage as measured by changes in kidney norepinephrine levels). Optionally, the time to produce the time insensitive effect is bounded by an upper time limit.

In an exemplary embodiment of the invention, blood flow in the artery is controlled to achieve the time insensitive effect, for example, by controlled cooling.

Overview of Treatment

Figure 1A:
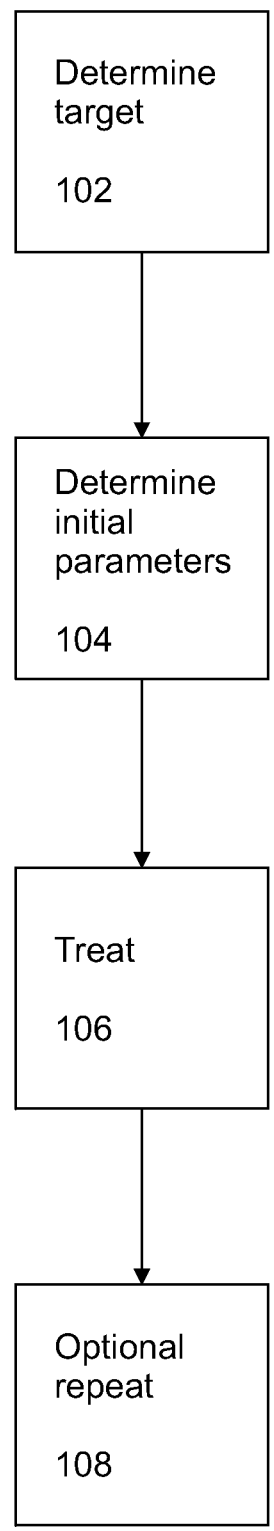

FIG. 1A is a flow chart of a method of selectively treating tissues using ultrasound energy, in accordance with an exemplary embodiment of the invention. Optionally, the ultrasound energy is applied at a selected frequency. Optionally or additionally, the ultrasound energy is applied at a selected intensity profile (e.g., watts per square centimeters, time of treatment). The method described in the flowchart is non-limiting. For example, some steps are optional. Furthermore, there can be other methods and/or other apparatus used to obtain the results.

At 102, a target tissue is optionally determined, for example, to treat a clinical disorder by damaging (e.g., ablating) the target tissue, in accordance with an exemplary embodiment of the invention.

In an exemplary embodiment of the invention, one or more factors related to the treatment (e.g., thermal effect) are optionally determined (e.g. manually by a physician, automatically by software), for example, the anatomical location (e.g., the blood vessel where the catheter will be inserted) of the lesion, the type of tissue to ablate (e.g. nerve), an extent of the treatment (e.g., thermal effect) (e.g., the entire tissue, part of the tissue), and/or safety considerations.

At 104, one or more parameters to result in the desired treatment (e.g., thermal effect) of the target tissue are optionally determined, in accordance with an exemplary embodiment of the invention.

Optionally, feedback is obtained about the treatment effect, for example, imaging of the target tissues. Alternatively, feedback is not required, as the initial settings are sufficient to achieve the desired treatment effect.

In an exemplary embodiment of the invention, localization of the treatment effect is optionally provided by one or more factors including, the blood cooling the vessel wall, the ultrasonic beam amplitude attenuation, the ultrasonic beam dispersion, and/or tissue types.

At 106, the target tissue as determined in 110 is treated using parameter settings as in 104, in accordance with an exemplary embodiment of the invention. Optionally, ultrasound energy is delivered by a transducer on a catheter inserted into the body. Optionally, the treatment is monitored.

Optionally, at 108, treatment is repeated, for example, immediately and/or at a later point in time. Optionally, treatment is adjusted in response to feedback.

In an exemplary embodiment of the invention, feedback optionally is related to the parameters used for transmission of ultrasonic energy, for example, associated with the treatment intensity profile. Optionally, feedback is related to the environment, for example, the rate of blood flow. Alternatively or additionally, feedback is related to the impedance of the acoustic element, such as to estimate changes in efficiency that can affect the transmitted acoustic intensity profile.

In an exemplary embodiment of the invention, feedback is optionally functionally related to the effects of the ultrasonic energy on tissues. Optionally, feedback in the form of imaging is used to detect the effect of treatment on tissues. Alternatively or additionally, feedback in the form of clinical measurements (e.g., blood pressure changes) are used to detect the effect.

In some embodiments, imaging is optionally used to evaluate the treatment (e.g., thermal damage to target tissue). Alternatively or additionally, the treatment is evaluated using other methods, such as clinical measurements, sometimes over the long term.

Control System

Figure 2:
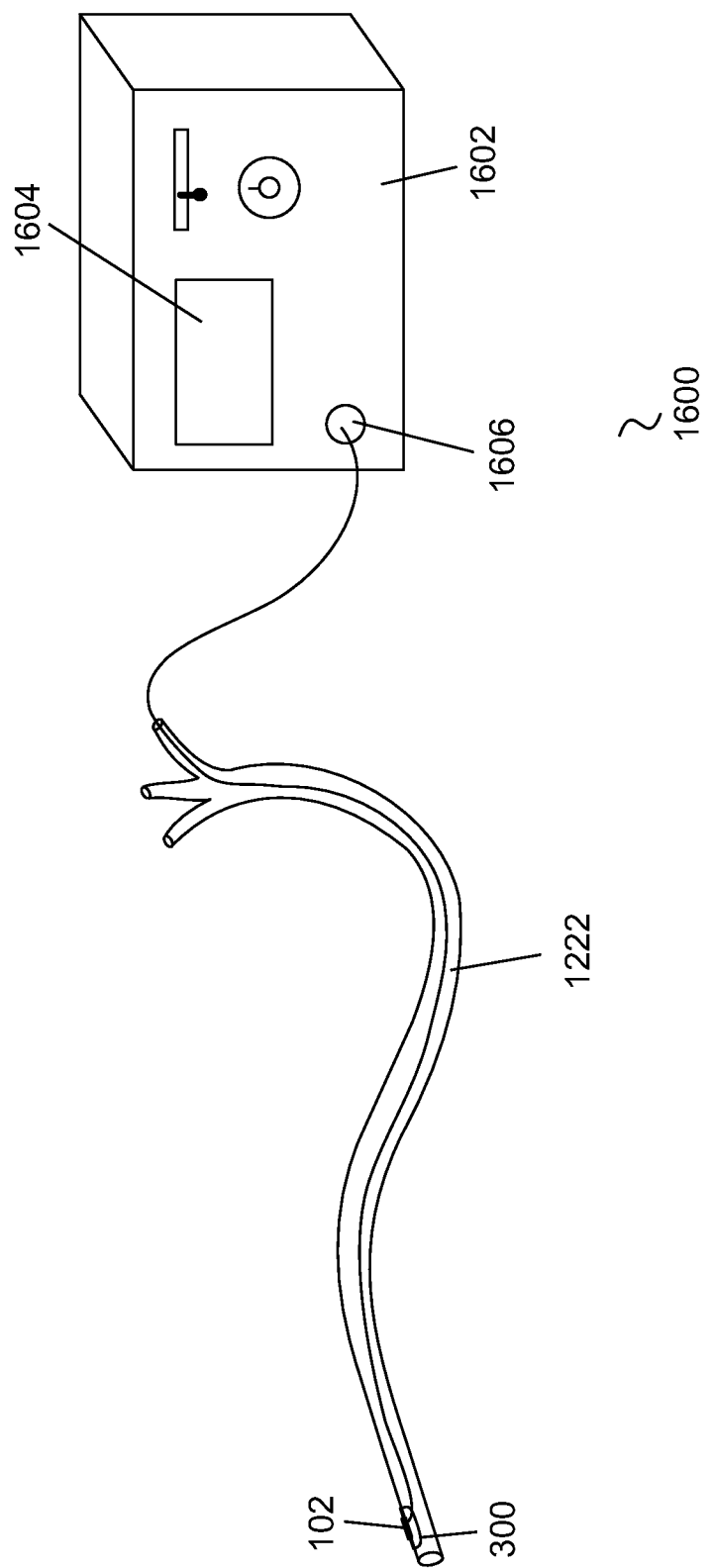

FIG. 2 illustrates an exemplary ultrasound treatment system 1600 for selectively treating tissues, in accordance with an exemplary embodiment of the invention. System 1600 provides for the control of the ultrasound treatment and/or monitoring of the treatment using catheter 1222. A transducer 300 comprising an acoustic element 102 to produce ultrasound energy is optionally located on a distal end of catheter 1222.

In an exemplary embodiment of the invention, an operator (e.g., physician performing the procedure) programs a controller 1602 (e.g., computer) for treatment using a user interface 1604 (e.g., keyboard, mouse, monitor). Optionally, treatment is monitored, for example, by viewing feedback parameters on interface 1604.

In an exemplary embodiment of the invention, a power port 1606 provides electrical power to electrodes across element 102, causing element 102 to vibrate at the set frequency, outputting a set ultrasound intensity profile.

In an exemplary embodiment of the invention, one or more functions and/or parameters and/or settings are programmed and/or set into controller 1602 (e.g., automatically determined by software such as according to a treatment plan). Optionally or additionally, one or more functions and/or parameters are selectable (e.g., manually set by a user, automatically selected by software).

One or more non-limiting examples of settable parameters include:

Impedance of element 102.

Acoustic feedback is feedback obtained by analyzing echoes of a diagnostic ultrasound signal returning from tissues, for example, as will be described in more detail with reference to FIG. 11.

Estimated or measured flow rate of blood across the surface of the acoustic element is important for controlling the temperature of the element to prevent overheating. In some embodiments, the flow rate of the blood is adjusted relatively higher or relatively lower, such as to control the temperature.

Estimated or measured flow rate of blood across the wall of the treatment target (e.g., blood vessel) is important for estimating the cooling capacity of the blood on the tissues of the wall being heated by ultrasound.

Efficiency is the estimated efficiency of converting electrical energy into ultrasound energy by the acoustic element.

Temperature control system cools and/or heats the element and/or tissues (e.g., blood vessel wall) to the desired temperature. Optionally, the temperature control system is used in combination with the blood flow. In some embodiments, the blood and/or tissue is pre-heated, for example, to obtain a relatively larger thermal effect.

Impulse excitation is the application of an impulse function (e.g., delta function) to the element, causing the element to vibrate with a decreasing amplitude. Impulse excitation is used to estimate a reduction in efficiency, useful as feedback, for example, to determine one or more of, thrombus formation on the element, the element coming in contact with the vessel wall, mechanical damage to the element.

Navigation system controls the movement and/or positioning and/or orientation of catheter 1222 and/or the transducer.

Pressure is the pressure caused by sound (e.g., acoustic intensity) during treatment and/or imaging.

Electric power is the applied power to the transducer.

Reflected electric power from the transducer back to the controller.

Voltage is the measured and/or applied voltage on the transducer.

Current is the measured and/or applied current in the transducer.

One or more non-limiting examples of selectable parameters include:

Frequency of the ultrasound energy produced by vibration of the acoustic element.

Waveform applied to the acoustic element, for example, a sinusoidal wave form.

Intensity is the produced ultrasound power divided by the surface area of the acoustic element.

Pulse duration is the length of a pulse of acoustic energy measured in time.

Duty cycle is the percentage of time in a single pulse that ultrasound energy is transmitted.

Temperature threshold is the approximate temperature of the element and/or the liquid (e.g., blood, saline) that should not be exceeded.

Treatment pattern is the spatial and/or temporal combination of one or more of the above variables, for example, a single pulse, a sequence of pulses, a train of pulses.

Focusing is the setting of non-focused vs. focused ultrasound energy.

The table below sets out some examples of the selectable parameters, and provides their theoretical limits, an exemplary treatment range, and an exemplary treatment sub range (e.g., most commonly used settings). It is important to note that some selectable parameters can only be selected from a pre-determined set, for example, in some embodiments, catheters are designed to operate at a specific frequency, in which case the user selects the frequency according to the catheter available.

| Exemplary Treatment sub range | Exemplary Treatment range | Theoretical range | Parameter |
| --- | --- | --- | --- |
| | | | Frequency (MHz): |
| 10-22 | 8-30 | 1-60 | Treatment |
| 10-25 | 10-60 | 1-60 | Imaging |
| 10-60 | 10-100 | 1-200 | Intensity (Watts/sq cm) |
| 50-100 | 10-100 | 0.1-100 | Duty cycle (%) |
| 0.1-2 | 0.1-4 | 0.01-1000 | Pulse duration (seconds) |
| 3-60 | 2-120 | 0.1-1000 | Duration of treatment (Seconds) per location |
| 35-70% | 20-70% | 1-70% | Efficiency (%) |
| 25-80 | 15-80 | 10-100 | Temperature (Celsius) |

Some Examples of Expected Effects Associated with Variables

The following are some non-limiting examples illustrating some parameters under control, and their association with some expected treatment effects, in accordance with an exemplary embodiment of the invention:

Impedance: a decrease of more than 10% suggests a decrease in efficiency of the acoustic element. The element will heat up more (e.g., requiring more cooling), and/or the acoustic intensity will decrease (e.g., requiring a higher intensity). In some embodiments, the impulse excitation is used to estimate the change in efficiency.

Acoustic feedback: imaging of the treatment region for the desired treatment (e.g., thermal effects) can be used to decide if to continue treatment, stop treatment or change treatment (e.g., increase or decrease acoustic intensity profile, change positions of catheter).

Estimated flow rate of blood across acoustic element: a change in blood flow can cause the element to overheat, potentially damaging the element.

Estimated flow rate of blood across wall of blood vessel: a decrease in flow rate reduces the cooling of tissues, potentially resulting in a larger treatment region for the given acoustic intensity. An increase in flow increases the cooling of the tissues, potentially resulting in a smaller treatment region. Alternatively, the location of the treatment region will be shifted. In some embodiments, the flow rate is controlled to within a predetermined range (e.g., as will be described below). Alternatively or additionally, the acoustic intensity profile is adjusted. Alternatively or additionally, the cooling system is used to maintain the temperature of the element and/or wall within the range.

Navigation system: imaging feedback can be used to detect if the treatment region is at the desired location (e.g., to the target tissue). Adjustments in position can be made accordingly.

Frequency: a relatively lower frequency of ultrasonic energy is able to penetrate relatively deeper into tissue. In some embodiments, relatively lower frequencies are used to achieve treatment regions relatively further away from the blood vessel wall.

Intensity: a relatively higher intensity of ultrasonic energy is able to penetrate relatively deeper into tissue and/or achieves a relatively higher heating of tissues quicker. In some embodiments, relatively higher intensities are used to achieve relatively larger treatment regions. Alternatively or additionally, treatment regions are further away from the vessel wall.

Pulse duration: a relatively longer pulse will deliver a relatively larger amount of ultrasonic energy to tissues, achieving a relatively larger treatment region.

Duty cycle: a relatively higher duty cycle will deliver a relatively higher amount of ultrasonic energy to tissues, achieving a relatively larger treatment region. In some embodiments, a relatively short duty cycle acts as a train of short pulses separated by delays, the effect of which is described below with reference to 'treatment pattern'.

Treatment Pattern: can be applied to achieve various treatment objectives, for example, a pulse of acoustic energy can be applied, followed by a delay period to allow cooling (e.g., by spreading of heat) before applying another pulse of energy. In another example, tissue can be targeted for treatment at one location, followed by a rotation (e.g., 10 degrees), followed by treatment at the second location, followed by a rotation to the first location.

Focusing: non-focused application of energy does not require precise anatomical positioning of the distance from the transducer to the target tissue throughout treatment, and achieves a relatively larger treatment volume using a relatively lower acoustic intensity. Focused application of energy requires precise positioning of the focal point to the target tissue throughout treatment, and achieves a relatively smaller treatment volume using a relatively higher intensity (e.g., total intensity at focal point).

Exemplary Method of Treatment

Figure 1B:
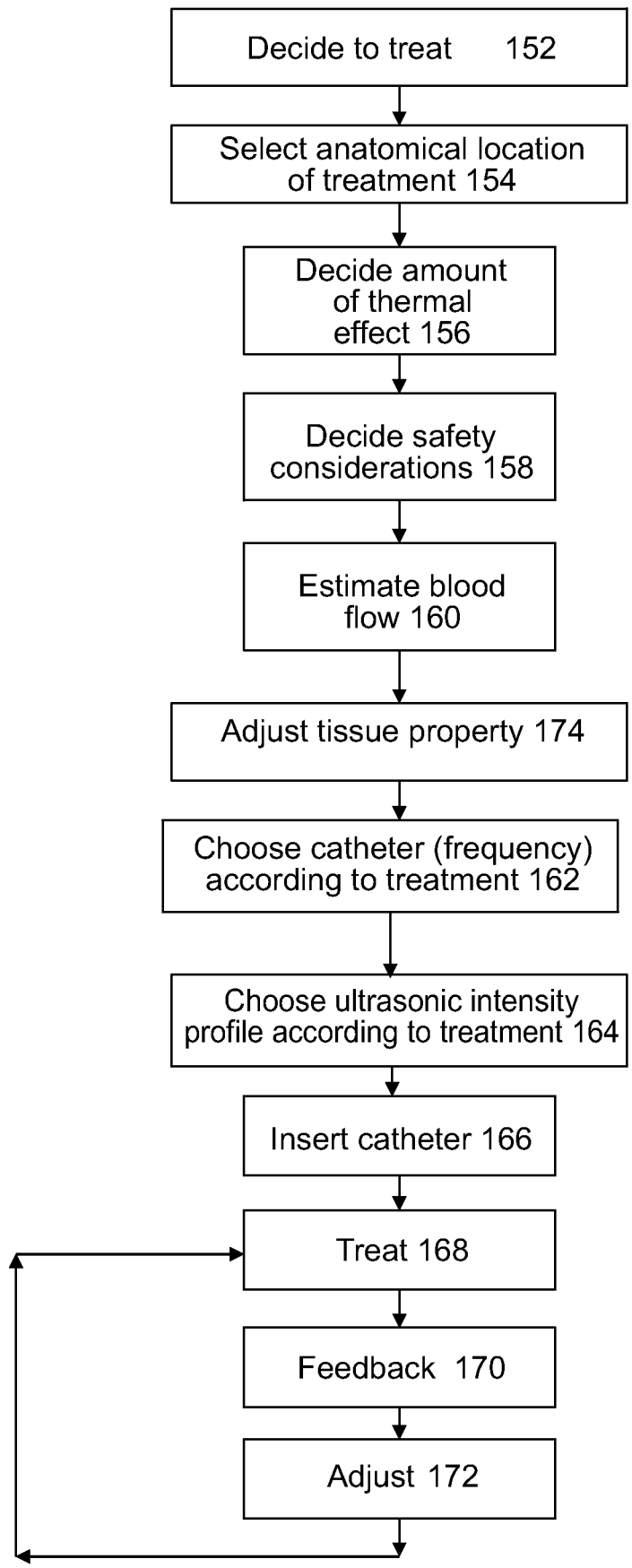

FIG. 1B is a detailed method of treatment of FIG. 1A, in accordance with an exemplary embodiment of the invention. It should be noted that the method described in the flowchart is non-limiting. For example, some steps are optional. Furthermore, there can be other methods and/or other apparatus used to obtain the results.

Optionally, at 152, a decision to treat is made, for example, as will be described in the section "DECIDING TO TREAT".

Optionally, at 154, the anatomical location to treat is selected, for example, as will be described in the section "SELECTING ANATOMICAL LOCATION OF TREATMENT".

Optionally, at 156, a decision is made with regards to the amount of damage to cause, for example, as will be described in the section, "DECIDE AMOUNT OF THERMAL EFFECT".

Optionally, at 158, a decision is made with regards to tradeoffs related to safety considerations, for example, increasing the margin of safety will result in less damage to surrounding tissue, but may not result in full treatment of the target tissue, for example, as will be described in the section "DECIDE SAFETY CONSIDERATIONS".

Optionally, at 160, the rate of blood flow in the artery is estimated, for example, as will be described in the section "ESTIMATE BLOOD FLOW".

Optionally, at 174, one or more tissue properties of the target tissue and/or surrounding tissue are adjusted, such as temperature and/or heat removal rate, for example, as will be described in the section "ADJUSTING TISSUE PROPERTIES". In some embodiments, the tissue properties are adjusted according to one or more parameters, such as the amount of thermal effect and/or safety considerations.

Optionally, at 162, the frequency of the ultrasound energy to apply is selected, such as by choosing a catheter designed to operate at that frequency, for example, as will be described in the section "CHOOSE CATHETER (FREQUENCY) ACCORDING TO TREATMENT". In some embodiments, the user is limited in the selection of the frequency according to the available frequency. At 164, the ultrasonic intensity profile is selected according to the treatment (e.g. watts per square centimeter, time of treatment, profile over time) for example, as will be described in the section "CHOOSE ULTRASONIC INTENSITY PROFILE ACCORDING TO TREATMENT".

Optionally, at 166, the catheter (e.g., as selected in 162) is inserted into the body of the patient and threaded to the treatment site (e.g., as selected in 154), for example, as will be described in the section "INSERT CATHETER".

At 168, the patient is treated, for example, as will be described in the section "TREAT".

Optionally, at 170, feedback is obtained, for example, as will be described in the section "FEEDBACK".

Optionally, at 172, adjustments are made, for example, to one or more parameters, and treatment continues as in 168, for example, as will be described in the section "ADJUST".

Deciding to Treat

In an exemplary embodiment of the invention, a decision to treat by damaging target tissue is made, for example, by a physician according to clinical indications.

Figure 3:
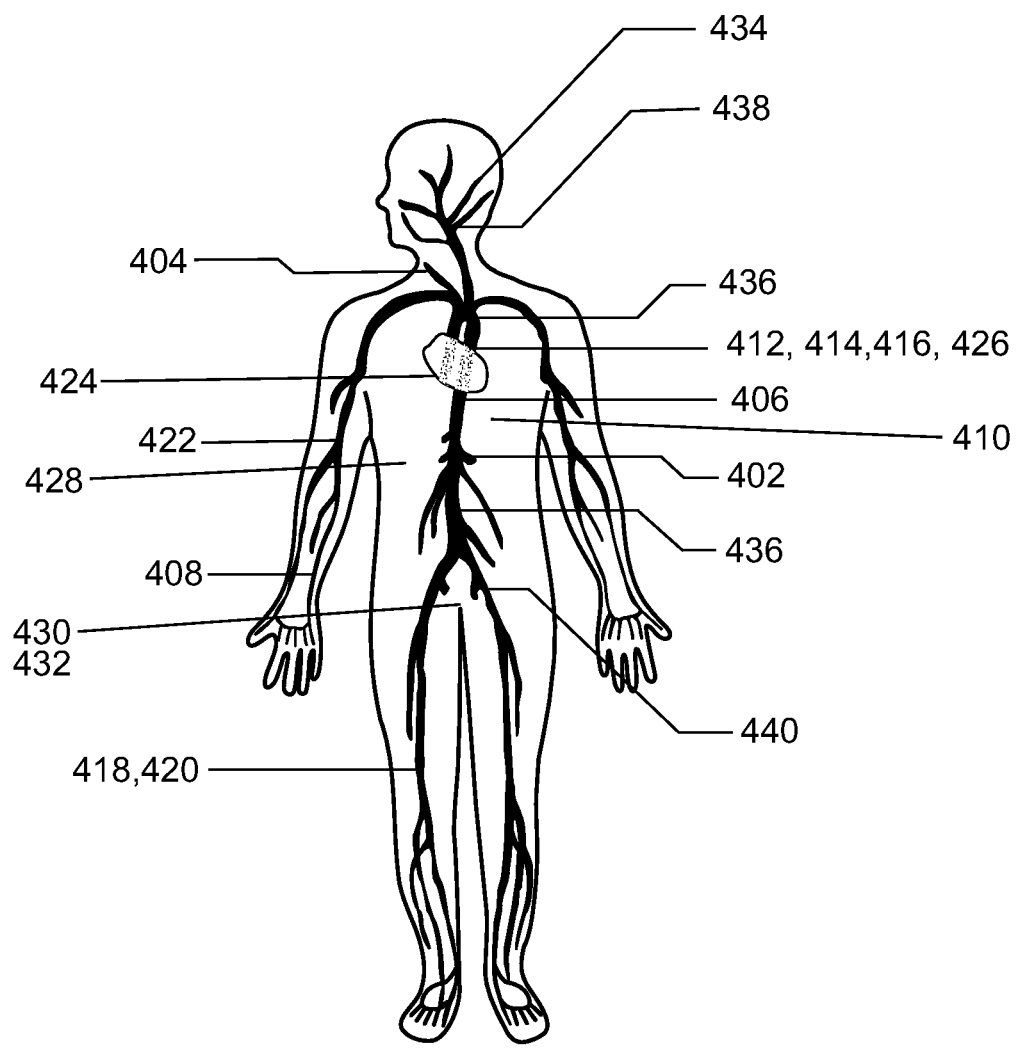

Non-limiting examples of clinical applications are listed in the table below. The applications listed in the table are referenced (e.g., according to numbers) to FIG. 3, which is an illustration of the human body showing the major arteries as reference points, useful in practicing some embodiments of the invention.

| Exemplary Clinical Applications | | | |
| --- | --- | --- | --- |
| Target | Anatomy | Application Name | # |
| Renal sympathetic nerves | Renal artery | Renal sympathetic nerve modulation | 402 |
| Carotid sympathetic nerves | Carotid artery | Carotid sympathetic nerve modulation | 404 |
| Vagus sympathetic nerve | Aorta | Vagus sympathetic nerve modulation | 406 |
| Peripheral sympathetic nerves | Peripheral blood vessels | Peripheral sympathetic nerve modulation | 408 |
| Pain nerves | Spinal cord cannel | Pain nerve modulation | 410 |
| Artery media and adventitia | All relevant arteries | Restenosis decrease | 412 |
| Artery media and adventitia | All relevant arteries | Vulnerable plaque stabilization | 414 |
| Artery media and adventitia | All relevant arteries | Atherosclerosis passivation | 416 |
| Artery media and adventitia | All relevant arteries | Plaque volume decrease | 418 |

-continued

Exemplary Clinical Applications

| Target | Anatomy | Application Name | # |
|---|---|---|---|
| Artery media and adventitia | All relevant arteries | Plaque thrombosis decrease | 420 |
| Peripheral motor nerves | Limb arteries or veins | Tetanic limb muscle tonus decrease | 422 |
| Pulmonary vain insertion | Right atria | Atrial fibrillation prevention | 424 |
| Cardiac tissue pathology | Coronary arteries | Cardiac arrhythmia prevention | 426 |
| Tumor | Inferior vena cava | Liver tumor necrosis | 428 |
| Sick prostate tissue | Urethra | None-malignant prostate treatment | 430 |
| Sick prostate tissue | Urethra | Malignant prostate treatment | 432 |
| Aneurysm wall | All relevant arteries | Artery aneurysms stabilization | 434 |
| Aneurysm wall | Aorta | Aortic aneurysms stabilization | 436 |
| Aneurysm wall | Brain arteries | Berry aneurysms sealing | 438 |
| Artery media and adventitia | Internal Iliac | Erectile dysfunction treatment | 440 |

A non-limiting method of stabilizing a plaque and/or aneurysm using ultrasound energy is described for example, in Sverdlik et al, in PCT/IL2008/000234, incorporated herein by reference in its entirety.

In an exemplary embodiment of the invention, nerve tissue is selectable for treatment by ultrasonic energy, for example, as will be described below with reference to FIG. 7B.

Some exemplary medical conditions and their proposed treatment by treating nerves (examples not limited to the nerves described, treating other nerves may achieve a similar clinical outcome) in accordance with an exemplary embodiment of the invention include:

Frozen shoulder—suprascapular nerve.
Zygapophysial joint pain—cervical medial branch nerves.
Chronic Pelvic Pain (in women)—uterosacral nerve.
Glabellar Frowning—facial nerve.
Phantom Pain—lumbar dorsal root ganglia.
Trigeminal Neuralgia—branches of the trigeminal nerve.
Cluster Headache—trigeminal and/or sphenopalatine ganglions.
Complex Regional Pain Syndrome—stellate ganglion.

In some embodiments, electrical signals through nerves are reduced by treatment, for example, by damaging some neurons in the nerve bundle. Alternatively or additionally, electrical signals through nerves are prevented from passing through, for example, by damaging the entire nerve bundle.

In some embodiments, malignant tissues (e.g., in the liver) and/or hypertrophic tissues (e.g., in the prostate) are damaged.

In some embodiments, the parameters to treat the tissues are obtained from a mathematical model, for example, as described in the section "EXEMPLARY DEVELOPMENT OF AN EQUATION" parts A and/or B.

Some non-limiting examples of how to achieve various desired effects using some embodiments of the invention are described. The description refers to obtaining the described effect. However, it should be noted that some effects overlap, and so some embodiments achieve one or more effects. In some embodiments, only the desired effect is achieved without other effects.

Coagulation—In some embodiments, heating tissue including blood to the range of 42-55 or 42-50 or other smaller, intermediate or larger values, results in blood coagulation without damage to surrounding tissues.

Denaturation—In some embodiments, heating tissue above 50, above 55, above 60 or other smaller, intermediate or larger values results in denaturation of collagen.

Apoptosis—In some embodiments, tissues are heated to over 85, over 95 degrees Celsius, or other smaller, intermediate or larger values to cause apoptosis, for example, as taught by Fung et al. Tissues affected are located about 0-0.5 mm away from the area of the applied energy.

Temporary/permanent disruption of nerve signals—In some embodiments, the length of nerve that is disrupted (e.g., burned) is selected to result in temporary or permanent disruption of nerve signals. For example, a relatively short disruption length can allow nerves to regenerate and reconnect, for example, about 0.1 mm, about 0.5 mm, about 1 mm, about 2 mm, about 5 mm, or other smaller, intermediate or larger values are used. Optionally, relatively long disruption lengths prevent nerves from regenerating and reconnecting, for example, about 10 mm, about 15 mm, about 20 mm, about 30 mm, or other smaller, intermediate or larger values are used.

Destruction—In some embodiments of the invention, tissues are heated to over 100 degrees Celsius to result in tissue destruction. A temperature of over 100 degrees Celsius results in vaporization of water, which can cause cells to burst.

Burning—In some embodiments, tissues are heated for relatively long periods of time to result in burning of the tissue, for example, over 10, 20, 30, 50, 100 seconds, or other smaller, intermediate or larger time periods. Alternatively or additionally, relatively high intensities are applied to result in the burn.

Degeneration—In some embodiments, tissues are heated to cause degeneration of the tissue, such as to about 47 degrees Celsius, for example, as taught by Xu & Pollock (see below).

Selecting Anatomical Location of Treatment

In an exemplary embodiment of the invention, the anatomical location for treatment (e.g., thermal effect) is selected. Optionally, a factor in the selection is the ability to apply ultrasound energy to the target tissue. One or more non-limiting examples of target tissues include, fat, nerves, vasa vasora, lymph, tumor, connective tissue, plaque (e.g., atherosclerotic).

In an exemplary embodiment of the invention, ultrasonic energy is applied invasively, for example, using a catheter and/or an endoscope. Alternatively, ultrasonic energy is applied non-invasively. Non-limiting examples from which treatment can be applied include one or more of, a fluid filled lumen (e.g., blood vessel), a non-fluid filled lumen (e.g., ureter), a fluid filled cavity (e.g., spinal canal), a non-fluid filled cavity (e.g., stomach), from outside the body (e.g., ultrasonic transducer is placed in a liquid such as water, and energy is delivered across the skin).

In an exemplary embodiment of the invention, a decision on the location of treatment is made from one or more different possible anatomical locations. Optionally, a factor in the selection is the location inside the lumen from which ultrasonic energy is applied, for example some locations are more easily accessed by using a catheter than others. Alternatively or additionally, a factor in the selection is the rate of blood flow in the blood vessel where the catheter will be positioned (e.g., some areas have more uniform flow), potentially important for cooling, for example, as will be described in the section "Estimate blood flow". In some cases, similar clinical effects will be achieved by thermal effects (e.g., damage) of at least one of the different locations.

Figure 4:
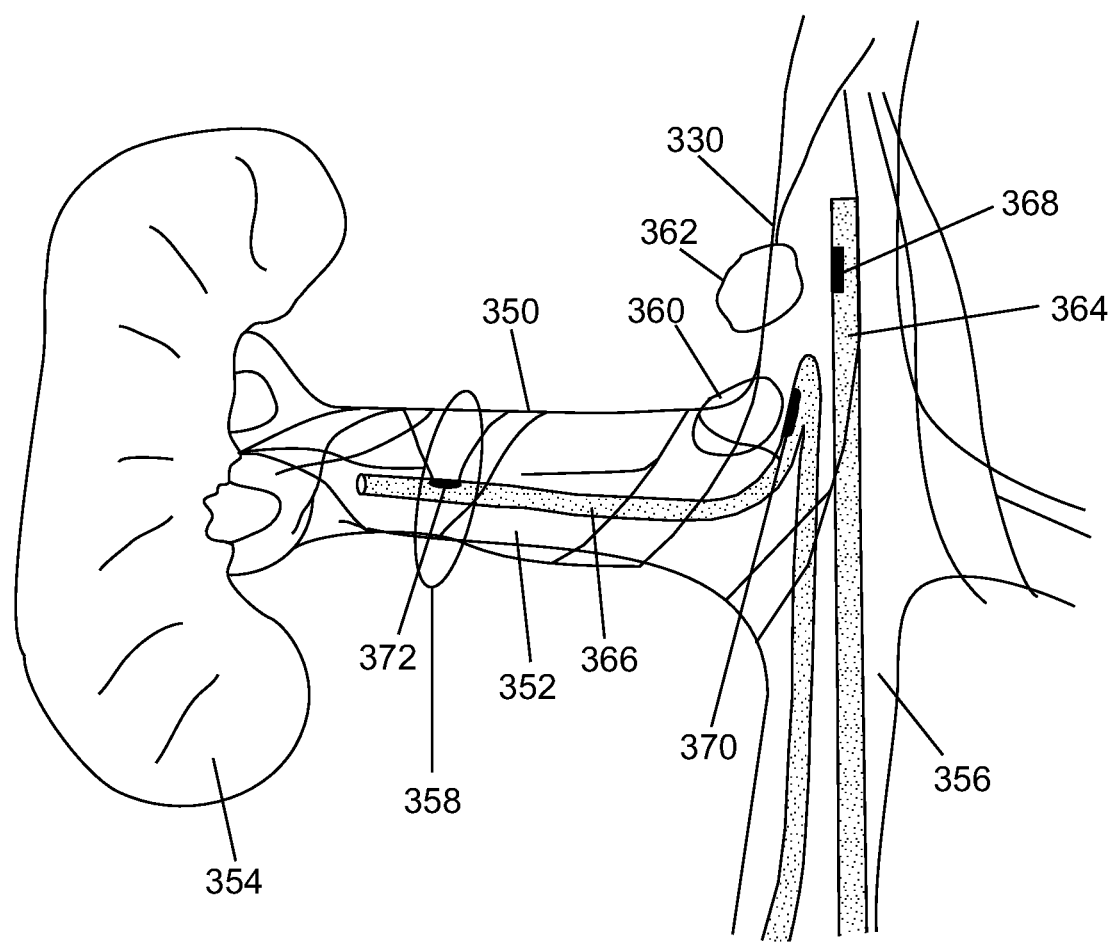

For example, a treatment of resistant essential hypertension is renal denervation. Reference is made to FIG. 4, which is an illustration of the anatomy of renal nerves 350 in relation to a right renal artery 352. Right renal artery 352 supplies blood to a right kidney 354 from an aorta 356. Commonly, renal nerves 350 arise from T10-L2 spinal roots, travel along aorta 356 and along renal artery 352 to innervate kidney 354. In some anatomies, renal nerves 350 primarily lie within the adventia of the renal artery 352 and/or aorta 356.

Non-limiting examples of conditions likely to respond to renal denervation:
  Resistant essential hypertension.
  Essential hypertension intolerant to medications.
  Nondipping essential hypertension.
  Resistant renovascular hypertension.
  Hypertension with chronic renal disease (unilateral or bilateral).
  Hypertension with obstructive sleep apnea intolerant to continuous positive airway pressure.
  Congestive heart failure (with reduced or preserved left ventricular systolic function) with cardiorenal syndrome.
  Hypertension in end-stage kidney disease on dialysis with native kidneys.
  Hypertension in renal transplant patients with remaining native kidneys.
Non-limiting examples of potential long-term benefits of renal denervation:
  Attenuation of arterial pressure.
  Stabilization of renal function with attenuation of the rate of decline of estimated glomerular filtration rate and reduction of proteinuria in hypertensive patients.
  Restoration of nocturnal dipping.
  Regression of left ventricular hypertrophy.
  Decreased insulin resistance.
  Slower progression of vascular disease.
  Decreased incidence of congestive heart failure with reduced ventricular hypertrophy, reduced salt and water retention, and improved exercise tolerance.
  Decreased risk of stroke.
  Decreased risk of atrial and ventricular arrhythmias.
  Decreased risk of sudden cardiac death.
  Further details about renal denervation can be found in an article by Katholi et al. "Renal nerves in the maintenance of hypertension: a potential therapeutic target" Curr Hypertens Rep. 2010 June; 12(3):196-204, incorporated herein by reference in its entirety.

There are one or more exemplary locations for performing the renal denervation procedure, useful in practicing some embodiments of the invention. For example, the procedure can be performed at a renal artery location 358 (e.g., from inside renal artery 352), at an ostium location 360 (e.g., the branch of renal artery 352 off aorta 356) and/or at an aorta location 362 (e.g., from inside aorta 356).

Non-limiting examples of factors affecting the location (e.g., 358, 360, 362) of treatment include simplicity of access, simplicity of the treatment procedure. For example, at location 358 multiple treatment areas may be required to ablate enough renal nerves 350 to achieve a desired clinical result of lowering blood pressure. For example, at location 360 and/or 362 two treatments can achieve the same effect, as the renal nerves 350 are concentrated together (e.g., afferent and efferent renal nerves travel together).

In some embodiments, catheters with ultrasound transducers for treatment at specific locations can be custom designed. For example, a straight catheter 364 with a transducer 368 can be designed for treatment at location 362. For example, a curved catheter 366 can be designed for treatment at location 360 (e.g., by placing a transducer 370 at the curve) and/or at location 358 (e.g., by placing a transducer 372 at the distal end of catheter 366).

In an exemplary embodiment of the invention, the ultrasound energy used to treat the target tissues does not need to be applied directly to the vessel wall. Optionally, the ultrasound energy is applied away from the vessel wall, for example, the transducer is not in contact with the wall.

In an exemplary embodiment of the invention, damage to the intima layer (e.g., endothelium) and/or internal elastic lamina of the vessel wall is prevented and/or reduced. A potential advantage is preventing and/or reducing the risk of adverse clinical outcomes, for example, one or more of, triggering a coagulation cascade, causing a vessel spasm, causing stenosis, blood loss due to injury to the vessel wall.

Exemplary Treatment Device

Figure 5:
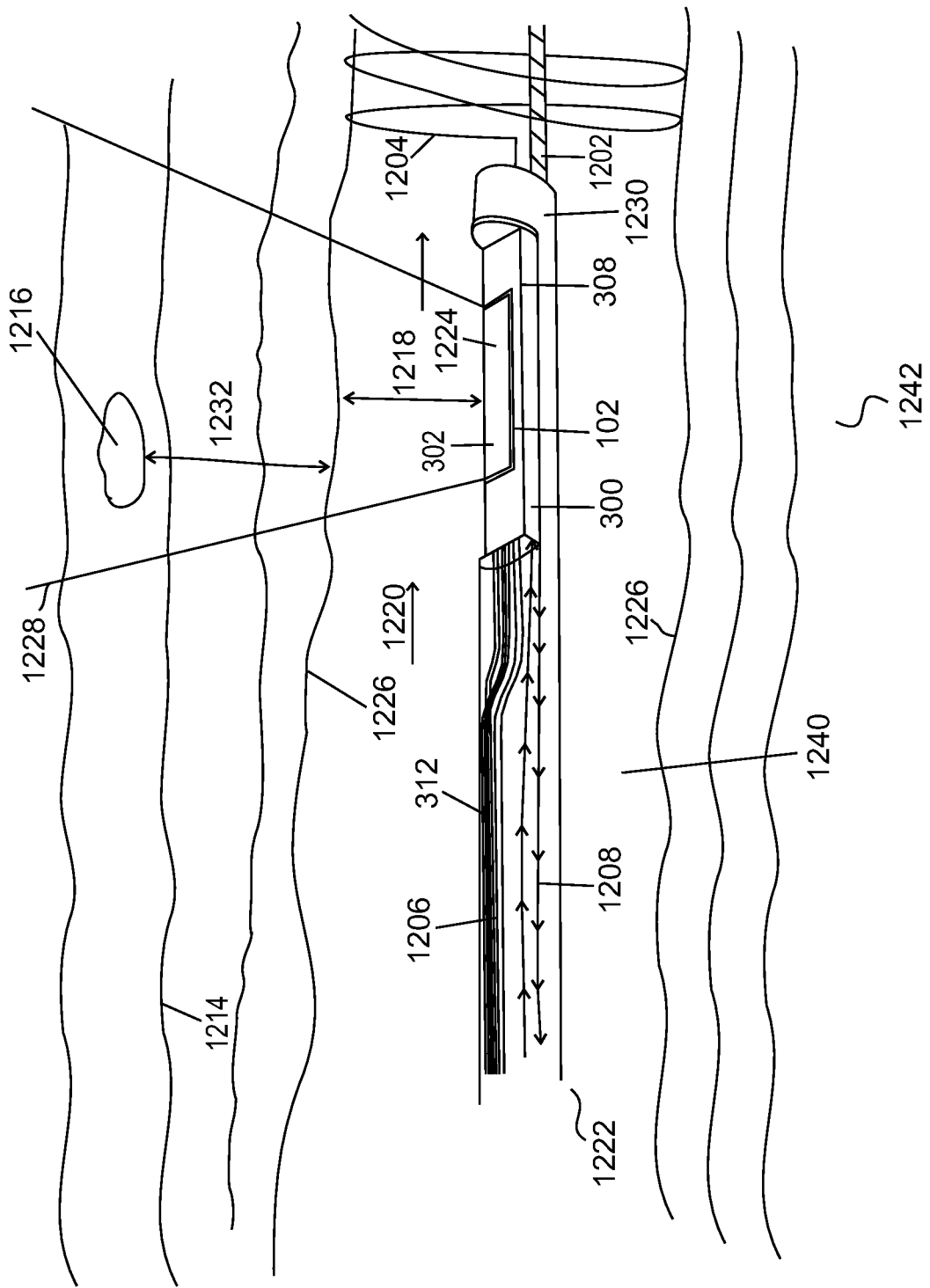

FIG. 5 illustrates a target tissue being irradiated with ultrasonic energy, in accordance with an exemplary embodiment of the invention. Shown is catheter 1222 inside a lumen 1240 of a blood vessel 1242 (e.g., artery). Optionally, an acoustic element 102 (e.g., part of transducer 300) emits a beam 1228 of ultrasound energy towards a target tissue 1216.

In an exemplary embodiment of the invention, the ultrasonic emission element and/or transducer 300 is capable of relatively high intensity ultrasound output. Optionally, transducer 300 is gas-backed, such as with a bubble of gas. Non-limiting examples of high intensity ultrasound include at least 20 watts/cm$^2$, at least 30 watts/cm$^2$, at least 50 watts/cm$^2$, at least 100 watts/cm$^2$ or other smaller, intermediate or larger intensities.

In an exemplary embodiment of the invention, beam 1228 is unfocused, for example, beam does not converged at a point, for example, beam diverges relatively little.

In an exemplary embodiment of the invention, the shape of element 102 is rectangular. Optionally, element 102 is planar. Optionally, a length of element 102 is, for example, about 1 mm, about 2 mm, about 4 mm, about 6 mm, about 8 mm, about 10 mm, or other smaller, intermediate or larger lengths are used. Optionally, a width of element 102 is, for example, about 0.2 mm, about 0.6 mm, about 1.0 mm, about 1.4 mm, about 2.0 mm, or other smaller, intermediate or larger widths are used.

In an exemplary embodiment of the invention, beam 1228 produced by a rectangular acoustic element is relatively straight, spreading an angle of about fifteen degrees relative to the exposed surface of element 102, when measured along the length.

In an exemplary embodiment of the invention, target tissue 1216 is located a distance 1232 away from wall 1226. Non-limiting examples of the maximum distance 1232 of target tissue 1216 that can be treated include 0.5 mm, 1 mm, 2 mm, 5 mm, 10 mm, or other smaller, intermediate or larger distances.

In an exemplary embodiment of the invention, target tissue 1216 is treated by an ultrasound beam 1228 from transducer 300. In an exemplary embodiment of the invention, treating comprises a thermal effect (e.g., heating to above 55 degrees Celsius) and/or a cavitation effect.

The table below illustrates some non-limiting examples of the effect of temperature on nerves over time. The rise in temperature is due to heat sources in general and is not limited to ultrasonic heating.

| Histological findings - summary | Follow up | Temp (° C.) | Article |
|---|---|---|---|
| Schwann cells - disrupted cytoplasmic organelles | Immediately after treatment | 47 | Xu & Pollock, 1994 |
| Blood vessels - collapsed; endothelia separated from overlying pericytes; swollen endothelia and perivascular oedema in endoneurial capillaries; Axoplasm - 'watery' | | | |
| Myelinated axons - degenerating | 2 hours after thermal injury | 47 | Xu & Pollock, 1994 |
| Myelin - decrease in diameter Myelinated axons - degenerated Myelinated fibers - distended | 6 hours after thermal injury | 47 | Xu & Pollock, 1994 |
| Axons - degenerated Schwann cells - hypertrophied | 1 day after thermal injury | 47 | Xu & Pollock, 1994 |
| Myelin - widened Schmidt-Lanterman incisures; disruption of myelin lamellae Blood vessels - endothelia separated from overlying pericytes; thrombosed; perivascular oedema Unmyelinated fiber - degenerated Unmyelinated axons - swollen and devoid of organelles | immediately after treatment | 58 | Xu & Pollock, 1994 |
| Nerve fibers - destructed | 3 days after thermal injury | 58 | Xu & Pollock, 1994 |
| Axons - fragmented; nodular appearance; continuity interrupted; decreased in length Myelin - vacuolated | | 24-48 | Lele, 1963 |

In an exemplary embodiment of the invention, damage and/or treatment to tissues (e.g., normal, healthy) surrounding target tissue 1216 is reduced and/or prevented. Optionally, treatment and/or damage to a volume of tissue between target tissue 1216 and wall 1226 is reduced and/or prevented.

In some embodiments, contact between an acoustic element 102 of transducer 300 and wall 1226 of vessel 1240, is reduced and/or prevented, for example, by a separation device 1204. Optionally, device 1204 maintains a distance 1218 between element 102 and wall 1226 of at least 1 mm. Optionally, a relatively cool liquid (e.g., blood, injected saline) flows in distance 1218. In an exemplary embodiment of the invention, the liquid cools element 102 and/or wall 1226.

In some embodiments, catheter 1222 comprises at least one transducer 300, positioned for example, on the side, such as inside a window cut into the catheter shaft 1230.

In an exemplary embodiment of the invention, element 102 is cooled. Optionally, cooling occurs by transfer of heat from element 102 to a surrounding fluid such as blood 1220, saline, urine, water, angiography contrast fluids, cerebrospinal fluid, lymph, mucous, stomach acid. Alternatively or additionally, cooling occurs by injection of a volume of a liquid (e.g., saline, radio-opaque dye) through tube 1206, and/or circulation of a liquid through tube 1208. Alternatively or additionally, cooling is increased using an active heat flux, such as a thermoelectric cooler. It should be noted, that herein cooling by blood flow also refers to cooling using other fluids (e.g., saline) in addition to blood, or cooling using other fluids as a substitution for blood cooling.

In an exemplary embodiment of the invention, a temperature sensing element, such as sensor 308, measures and/or estimates the temperature of element 102. In an exemplary embodiment of the invention, sensor 308 measures the temperature of blood that has flowed 1220 over a surface 1224 of element 102. In an exemplary embodiment of the invention, the temperature of the blood that has flowed 1220 over surface 1224 is used as an estimate of the temperature of element 102.

In an exemplary embodiment of the invention, a 6 mm long×1 mm wide transducer emitting ultrasound energy at an intensity of 100 Watts/square centimeter, is calculated to generate about 11-24 Watts of excess heat (variation according to efficiency of operation) for removal. The amount of heat generated varies linearly with the size of the element and/or the intensity of emitted ultrasound energy.

Decide Amount of Damage

Figure 6A:
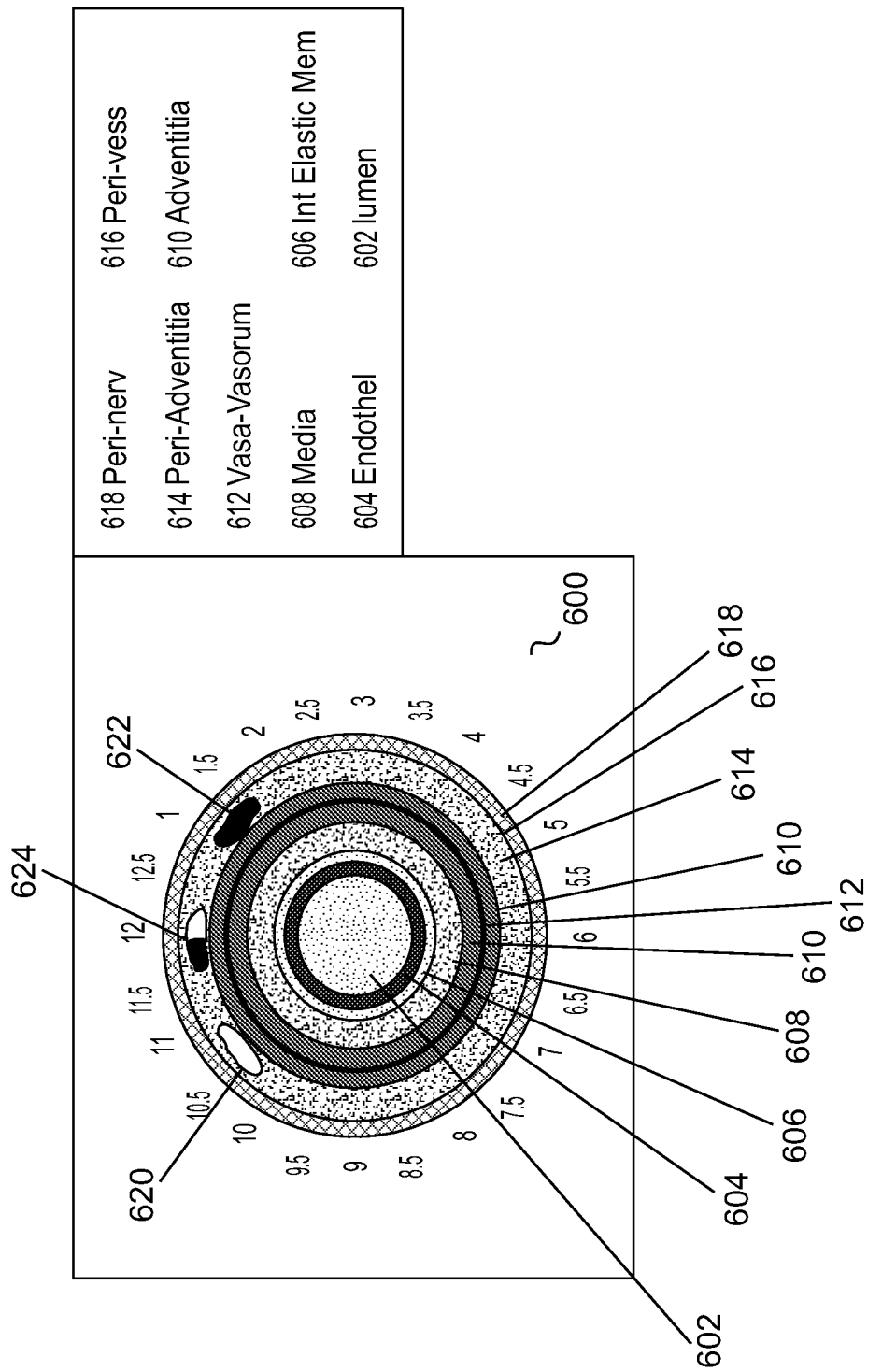

FIG. 6A is a schematic diagram of a cross section of an artery 600, useful in practicing some embodiments of the invention. The layers of the wall of artery 600, from a lumen 602 outwards are: endothelium 604, internal elastic media 606, media 608, adventia 610 having vasa vosorum 612 embedded therein, peri-adventitia 614, peri-vess (peri-adventitia blood vessels (capillaries)) 616, peri-nery (peri-adventitia nerve fibers) 618.

In an exemplary embodiment of the invention, one type of target tissue is nerve tissue 620. In some anatomies, nerves 620 surrounded by fat are especially well suited for targeted treatment, for example, as will be discussed with reference to FIG. 7B. Nerve tissue 620 is commonly located in peri-adventitia 614.

In an exemplary embodiment of the invention, the extent of damage is selectable and/or controllable. Optionally, damage is selected to include only the target tissue, for example, thermal damaged nerves 622. Alternatively or additionally, damage is selected to include tissue surrounding the target tissue.

In an exemplary embodiment of the invention, the portion of the target tissue to treat by thermal effect is selected. Optionally, a portion of the target tissue experiences thermal damage and a portion of the same target tissue does not experience damage, for example, as shown with reference to nerve 624. The left side of nerve 624 experienced thermal damage and the right side of nerve 624 did not experience thermal damage. In an exemplary embodiment of the invention, the effect of thermal damage to portion of the target tissue is associated with an unfocused ultrasound beam that is relatively high in acoustic intensity, and diverges a relatively small amount. In some embodiments, a portion of the nerve is treated by directing the ultrasound beam to the desired targeted portion of the nerve. Alternatively or additionally, parameters are selected to treat the portion of the nerve, for example, a thermal effect that starts a first distance away from the intima and ends a relatively closer second distance away from the intima, where the target portion of the nerve falls between the first and second distances, and the portion not to be treated falls between the second distance and the intima.

In an exemplary embodiment of the invention, the extent of the damage to the target tissue is selected, for example, tissues can be partially damaged to the extent that the damage is reversible (e.g., tissue can self regenerate and/or heal).

In an exemplary embodiment of the invention, the functional result of the treatment is selected, for example, to achieve a temporary effect (e.g., reversible effect).

In an exemplary embodiment of the invention, the spatial profile of the thermal effect is selectable, for example, the volume of the thermal effect.

Figure 6B:
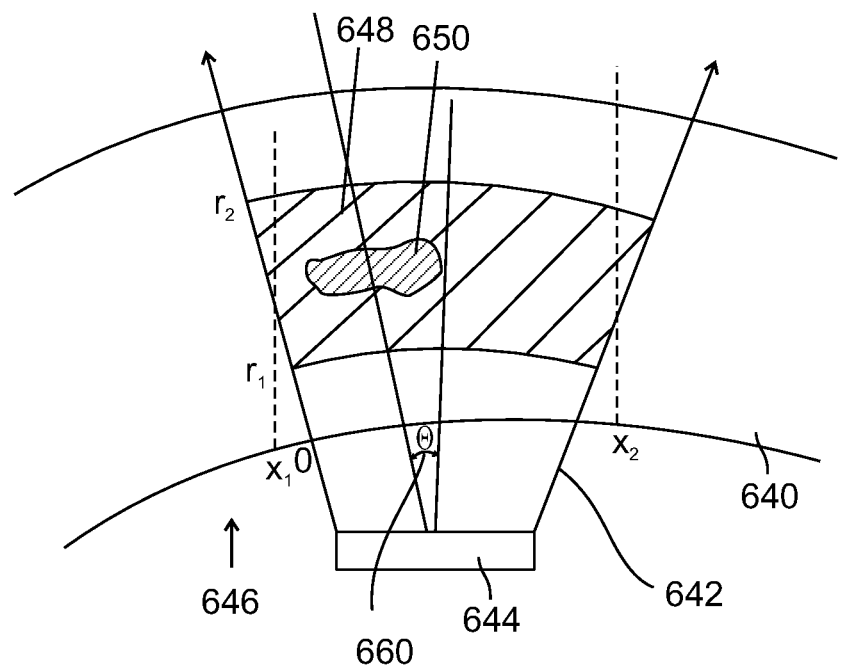
Figure 6C:
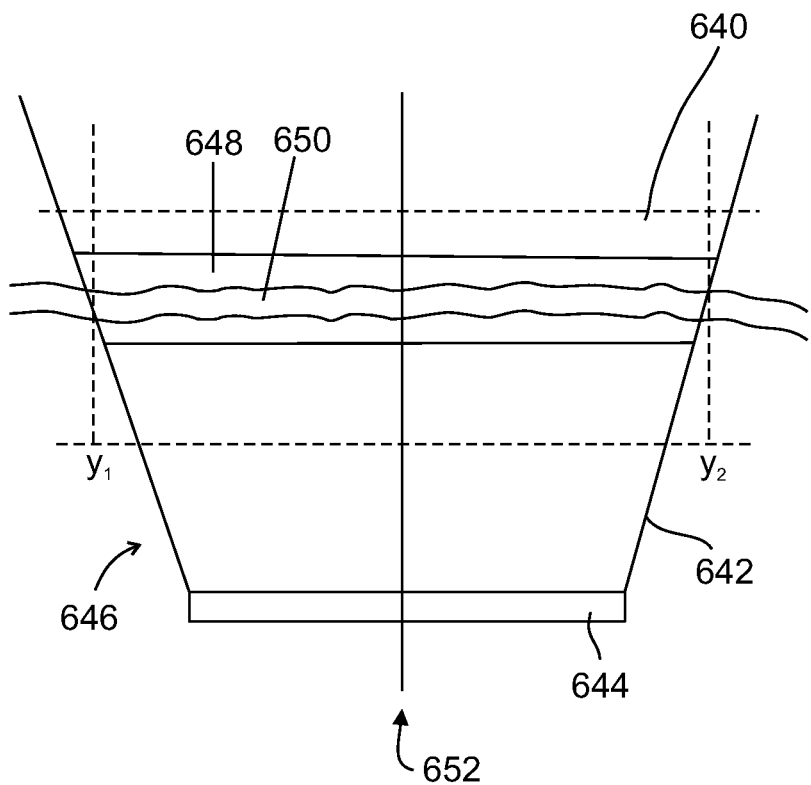
Figure 6D:
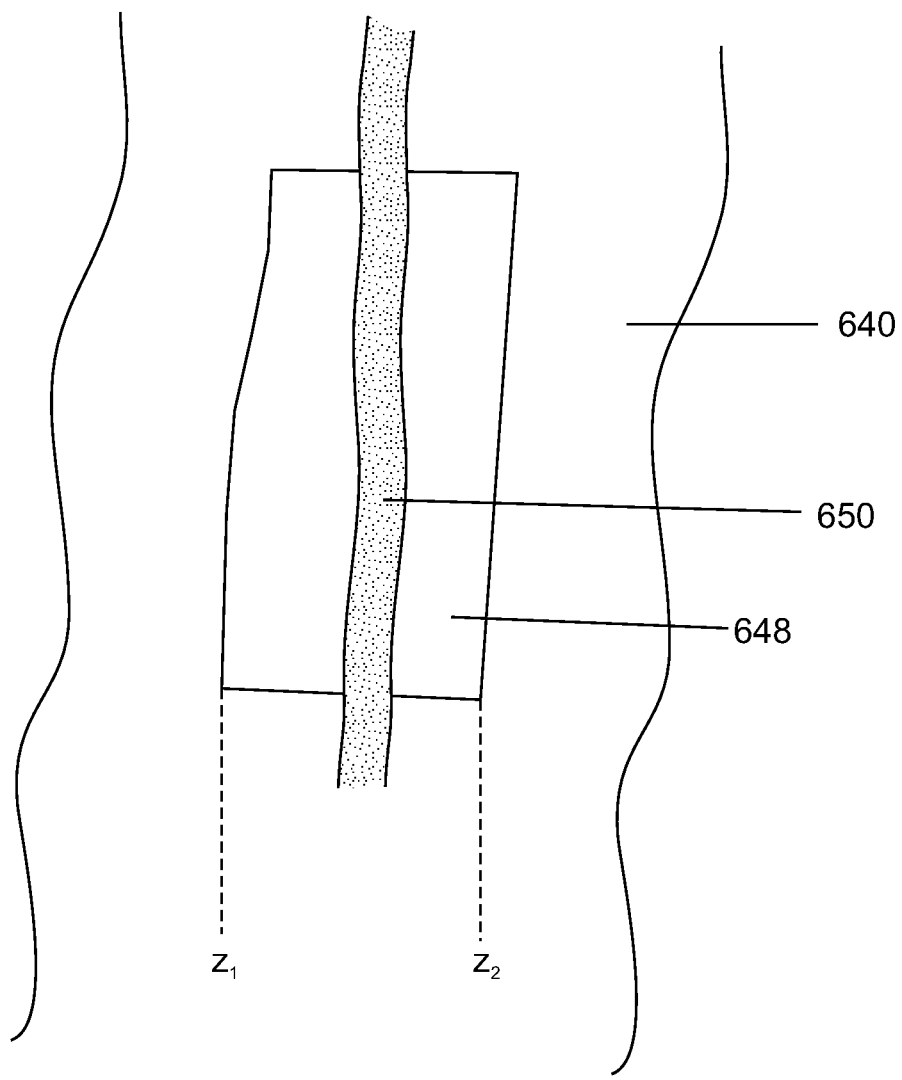

FIG. 6B is a cross sectional view, FIG. 6C is a side view and FIG. 6D is a top view illustrating a controllable volume of damage 648 to tissue, for example to a blood vessel wall 640, in accordance with an exemplary embodiment of the invention. Optionally, damage is caused by an ultrasound beam 642 from a transducer 644.

In an exemplary embodiment of the invention, damage is selectable a distance into wall 640 as measured from a lumen 646, for example, zero is set at the boundary of wall 640 and lumen 646. Optionally, damage starts at about a distance "r1" and ends at about a distance "r2", wherein r1 is greater than or equal to zero and r2>r1. In some embodiments, r2 is greater than the thickness of wall 640, for example, tissues outside of the blood vessel can be damaged.

In an exemplary embodiment of the invention, the volume of damage 648 is selectable, for example, the volume of damage is an area of about "x2−x1" (e.g., measured along the cross section of the blood vessel) multiplied by about "y2−y1" (e.g., measured along the long axis of the blood vessel) multiplied by about "z2−z1" (e.g., measured parallel to the diameter of the blood vessel). Optionally, the volume of the damage is associated with one or more factors, such as the size and/or area of an acoustic element of transducer 644, the tissues in the wall (e.g., the tissues from the intima to the target tissue, as well as the target tissue), and/or the interaction between the tissues and the ultrasonic energy (e.g., attenuation).

In an exemplary embodiment of the invention, the location of damage 648 is selectable. Optionally, an angular location 660 of damage is selectable, for example, in the range of 0-360 degrees, as determined by an arbitrary reference such as on a fluoroscopic image. Alternatively or additionally, a longitudinal location 652 in the artery is selectable, for example, measured in centimeters, as determined by an arbitrary reference such as distance from an arterial branch. Optionally, angle 660 and/or longitudinal location 652 are selected according to the position of transducer 644, for example, rotating transducer and/or longitudinal positioning of transducer 644. Optionally or additionally, the extent of the thermal effect and/or thermal damage is selectable.

In an exemplary embodiment of the invention, a damage axis (e.g., the volume of thermal damage) is aligned with the tissue axis. For example, to cause a clinical effect in elongated nerves such as by thermally damaging them, it is sufficient to treat a section of the nerve as opposed to the entire nerve.

Partial Denervation

In some embodiments of the invention, only partial denervation is desired, for example, it may be desired to reduce the function of the nerves by, for example, 20%, 30%, 50%, 80%, 90% or intermediate or larger amounts. In an exemplary embodiment of the invention, the function of the nerves is measured by the effect on the target tissue controlled by the nerves and/or providing signals to the nerves, rather than by the nerves ability to transmit signals.

In an exemplary embodiment of the invention, it is desirable to maintain some of the natural feedback controls over blood pressure and/or other biological functions, provided by the nerve (e.g., as part of a biological system), albeit, at an attenuated level, for example, to compensate in part or in full and/or overcompensate for a diseased state caused by such feedback. It has, in fact, been found that even partial denervation which only causes a drop of Renal Norepinephrine spillover to about 50% from baseline (e.g., in a diseased patient), still provides a significant drop in blood pressure.

In greater detail. In the kidney, Norepinephrine (NE) is stored only in the renal sympathetic nerve terminals from where it is released in relation to increases in renal sympathetic nerve activity (renal Norepinephrine spillover (NESO)). Thus, it is reasonable to assume that if renal tissue NE content is decreased, then there is less NE in the renal sympathetic nerve terminals available for release and that renal NESO will be decreased somewhat in proportion to the decrease in renal tissue NE content. Thus, in this way, a rough correlation is to be expected between the renal tissue NE content and renal NESO. It is noted that this relationship is not a precise and/or necessarily a linear relationship.

In organ physiology, the assumption is made that if a control mechanism exists, then it is meant to fulfill a vital function, even if it is redundant to other control systems. Thus, the efferent renal nerves are involved in controlling certain renal functions (GFR, RBF, sodium handling, renin release, etc.). Activation of these mechanisms in times of volume depletion (hemorrhage, etc.) can be of value in preserving integrity of body fluid volumes and cardiovascular integrity. The afferent renal nerves sense pain (e.g., due to kidney stone) as well as provide other reflex inputs to the central nervous system that influence systemic sympathetic outflow to the periphery. While it believed that efferent renal nerves grow back and that afferent renal nerves do not grow back, the consequences of total (afferent and efferent) renal denervation over a long time future is not clear and it may be desirable to avoid.

In an exemplary embodiment of the invention, selecting the treatment parameters includes deciding on a desired degree of denervation and/or desired change in NE, for example, a change over time, for example, a change at one day (from denervation), 10 days, 30 days, 90 days and/or intermediate and/or longer times and/or at a plurality of times. Optionally, after a period of time, for example, 1 month or several months, a partial denervation may be repeated (e.g., at one or both kidneys), for example, to achieve a desired results shown by the NE levels (or a marker thereof) not to have been achieved.

Decide Safety Considerations

In an exemplary embodiment of the invention, a margin of safety is selectable.

In an exemplary embodiment of the invention, the extent of damage to tissues (e.g., normal and/or healthy) surrounding a target tissue 650 (e.g., nerve) is selectable. Optionally, volume of damage 648 is approximately a volume of target tissue 650. Alternatively, volume of damage 648 is relatively larger than the volume of target tissue 650.

In an exemplary embodiment of the invention, the volume of normal tissue treated (e.g., in volume of thermal damage 648) surrounding target tissue 650 is selectable, for example, as a margin of safety. A potential advantage is a trade-off between certainty of damaging target tissue 650 and damaging nearby tissue (e.g., healthy and/or normal).

In an exemplary embodiment of the invention, side effects as a result of treatment are selectively reduced and/or prevented by proper selection of treatment parameters. For example, one or more scarring, shrinking and/or spasm of the blood vessel may be reduced such as by a treatment profile that maintains a temperature sufficiently low to achieve a thermal effect while avoiding side effects (e.g., 55 degrees Celsius) and/or for a time period sufficiently long to achieve the thermal effect while avoiding side effects.

Estimate Blood Flow

In an exemplary embodiment of the invention, the rate of blood flow is measured and/or estimated, for example, using one or more methods including, a look-up table of estimated blood flow rates in blood vessels, Doppler, flow sensor, temperature measurement downstream of the transducer (e.g., measuring temperature to estimate if blood flow is sufficient). Optionally, the rate of blood flow as a function of time is controlled, for example, by inflating and/or deflating a balloon upstream from the transducer. Alternatively or additionally, a liquid (e.g., saline, radio-opaque dye) is injected to create flow.

In some embodiments of the invention, the diameter of the catheter is selected according to the desired rate of blood flow. For example, a relatively smaller catheter is selected to provide for relatively greater blood flow, such as a relatively faster rate of blood flow. For example, a relatively larger catheter is selected to provide for relatively slower blood flow. Non-limiting examples of diameters include; 1 mm, 2 mm, 3 mm, 4 mm, 5 mm, or other smaller, intermediate or larger values are used. Optionally, the diameter of the catheter is selected relative to the diameter of the blood vessel, for example, about 20%, 30%, 40%, 50%, 75% of the vessel diameter, or other smaller, intermediate or larger values are used.

FIG. 7A illustrates an exemplary of a simplified estimate of the association between a flow of blood and the location of an area of damage.

The upper part of FIG. 7A shows an ultrasound transducer 706 emitting ultrasound energy 708 at a target tissue 712. Energy 708 travels across a lumen 730 (e.g., of a blood vessel) into a blood vessel wall 710. Energy 708 causes an area of damage 704. Blood flows 702 inside lumen 730.

Without being bound to theory, the lower part of FIG. 7A illustrates an exemplary association between blood flow 702 and the resulting area of damage 704. Damage 704 is hypothesized to occur when the temperature of a tissue reaches 55 degrees Celsius or higher. The temperature in tissues of blood vessel wall 710 is a tradeoff between the tissues being heated by ultrasonic energy 708 (e.g., mechanical friction) and the tissues being cooled by flow of blood 702 (e.g., convection).

Curve 714 is an exemplary illustration of a simplified estimate of the effect of heating of wall 710 due to ultrasonic energy 708 absorption (e.g., attenuation) as a function of distance away from lumen 730. As energy 708 travels through wall 710, it is absorbed, resulting in tissue of wall 710 heating up. Without blood flow 702, the tissues closest to lumen 730 heat up the most and the tissues furthest away heat up the least.

Curve 716 is an exemplary illustration of the cooling effect on wall 710 due to blood flow 702 as a function of distance away from lumen 730. Tissues closest to lumen 730 are cooled relatively more by blood flow 702, and tissues furthest away are cooled relatively less.

Without being bound to theory, if heat generated by ultrasonic energy 708 is removed sufficiently quickly by blood flow 702, the tissues in wall 710 will not heat up enough to achieve a thermal effect. At the point where the heat due to energy 708 is not removed fast enough, the tissue can heat up to 55 degrees, potentially resulting in area of thermal damage 704.

In an exemplary embodiment of the invention, blood flow 702 is taken into account to adjust parameters to treat target tissue 712 and/or to set area of thermal damage 704, for example, by using a look-up table of correlated values and/or using a mathematical formula modeling (e.g., manually by a user, automatically by a software module). Optionally, the intensity profile of energy 708 (e.g., time of treatment, intensity of energy emitted) is selected according to target tissue 712 and/or area of thermal damage 704. Alternatively or additionally, the frequency of ultrasonic energy 708 is selected.

FIG. 7B is an exemplary graph illustrating a simplified estimate of the effects of various tissues absorbing ultrasound energy in obtaining a desired thermal effect, useful in practicing some embodiments of the invention. In an exemplary embodiment of the invention, selecting target tissue for treatment is associated with the ability of the target tissue and/or tissues between the transducer and the target tissues in attenuating ultrasonic energy.

The table below illustrates the ability of different types of tissues to absorb (e.g., attenuate) ultrasound energy. Tissues having relatively higher coefficients of attenuation, heat relatively more.

In an exemplary embodiment of the invention, the relatively values as shown in the table are used to prepare a treatment plan to selectively target tissues. For example, to selectively target connective tissue ($\alpha=1.57$) surrounding muscle ($\alpha=1.09$), the treatment plan can consist of bursts of ultrasonic energy separated by gaps without energy transmission. During the bursts, the ultrasonic energy will be attenuated relatively more by the connective tissue resulting in a relatively higher temperature. During the gaps, the ultrasonic energy will be dispersed relatively more quickly by the muscle. The net result of the treatment pattern is that connective tissues will be heated to a thermal effect, while the muscle will not achieve a temperature high enough to be thermally affected.

| $\alpha(dB/(MHz \cdot cm))$ | Material |
|---|---|
| 0.2 | Blood |
| 0.48 | Fat |
| 0.5 | Liver |
| 0.52 | Cardiac |
| 0.6 | Brain |
| 0.75 | Breast |
| 1.09 | Muscle |
| 1.57 | Connective tissue |
| 4.7 | Tendon |
| 6.9 | Bone, cortical |

The top part of FIG. 7B illustrates transducer 706 emitting ultrasonic energy 708 into arterial wall 710. The bottom part of FIG. 7B illustrates relative energy 708 absorption by different tissues.

Starting from lumen 730, the layers of wall 710 can be categorized as intima 718, media 720 and adventitia 722. As intima 718 is a single layer of endothelial cells, energy 708 absorption can be assumed to be negligible. Media 720 is primarily muscle, having a relatively low level of absorption. Adventitia is primarily connective tissue, having a relatively higher level of absorption. The attenuation of acoustic energy is inversely related to frequency, for example, a relatively higher frequency results in relatively higher attenuation. In an exemplary embodiment of the invention, an area of damage is associated with relatively higher levels of energy 708 absorption by adventitia 722.

In an exemplary embodiment of the invention, the relative attenuation of energy 708 by tissues is taken into account when deciding on treatment parameters for the target tissue. In some embodiments, the target tissue is nerve 724. Nerve 724 is primarily connective tissue, having a relatively higher US attenuation coefficient. In some embodiments, nerve 724 is selectively targeted for damage.

In some cases, nerve 724 is surrounded by a layer of fat 726. Fat 726 has a relatively lower level of absorption (e.g., attenuation of the acoustic energy) and relatively low level of thermal conductivity (e.g., doesn't transfer the thermal energy). Inventors hypothesize that fat 726 acts as a thermal insulator for nerve 724, trapping the US energy absorbed by nerve 724 (e.g., heat), as the heat dissipation outside fat ring 726 is relatively higher (e.g., relatively lower attenuation coefficient), the outside tissues do not heat up as much. In an exemplary embodiment of the invention, nerve 724 surrounded by fat 726 is selectively targeted for thermal damage. In an exemplary embodiment of the invention, energy 708 causes temperature in nerve 724 surrounded by fat 726 to exceed a threshold, resulting in thermal damage 728 to nerve 724, while tissues surrounding fat 726 are not thermally affected (e.g., damaged).

FIG. 7C is an exemplary graph illustrating a simplified estimate of the effect of the ability of heat removal in obtaining a desired thermal effect, useful in practicing some embodiments of the invention. In an exemplary embodiment of the invention, selecting target tissue for thermal damage is associated with the capacity of heat removal from the target tissues and/or surrounding tissues.

In an exemplary embodiment of the invention, heat removal from tissues in wall 710 occurs from lumen 730. Optionally, the rate of heat removal is variable. Alternatively or additionally, the rate of heat removal is controllable.

In an exemplary embodiment of the invention, heat removal is accomplished by a flow of blood in the lumen. Without being bound to theory, a higher flow of blood results in a higher rate of heat removal. Optionally, the flow of blood in the lumen is selectable and/or controllable, for example, by one or more methods such as, cardiac pacing (e.g., artificially controlling the heart rate), inflating a balloon inside the artery, and/or operating an obstructing structure on the catheter, to at least partially block the flow of blood and/or to direct the flow to the target artery wall.

In an exemplary embodiment of the invention, heat removal is associated with the temperature of the blood in the lumen. Without being bound to theory, a lower blood temperature results in a higher rate of heat removal. Optionally, the temperature of blood is selectable and/or controllable, for example, by injection of a relatively cold liquid upstream from the treatment area (e.g. saline, radio-opaque dye, patient's own blood that has been cooled).

For illustrative purposes, FIG. 7C shows a relatively slow heat removal 740 and a relatively fast heat removal 742 in lumen 730. In some embodiments, slow heat removal 740 results in a thermal damage area 744 that is relatively closer to lumen 730. In some embodiments, fast heat removal 742 results in a thermal damage area 746 that is relatively further away from lumen 730.

Without being bound to theory, the bottom part of FIG. 7C shows that for the same ultrasound attenuation curve 714 (e.g. ultrasound energy 708 produced by transducer 706), a slow removal curve 748 causes thermal damage area 744 relatively closer to lumen 730 as compared with a fast removal curve 750 that causes thermal damage area 746 relatively further from lumen 730.

Adjusting Tissue Properties

In some embodiments of the invention, one or more tissue parameters are adjusted. Optionally, the tissue is adjusted (which affects the tissue parameters) in accordance with one or more treatment parameters, for example, the selected safety profile and/or selected amount of thermal effect. Optionally, parameters are adjusted relatively higher or relatively lower.

In an exemplary embodiment of the invention, adjustment is provided by the controller, optionally using the catheter, for example, to deliver an electrical current or a drug to the artery and/or to the heart and/or other tissue, such as tissue near the artery. Alternatively a separate application device is provided. In an exemplary embodiment of the invention, the adjustment is automatic. Alternatively, the adjustment is in response to a manual control. Optionally, the adjustment is semi automatic, with the controller, for example, modifying the adjustment means to maintain a user-indicated result, such as vessel diameter. In an exemplary embodiment of the invention, the treatment is modified (e.g., automatically, by the controller) in realtime to match the modification and/or so it is applied when the blood vessel properties are within a given window (e.g., timed to thickness changes associated with the pulse wave), even if no intentional adjustments is applied.

FIGS. 7D and 7E illustrate non-limiting examples of adjustments of tissue parameters, in accordance with some embodiments of the invention. FIG. 7D illustrates a relative decrease in tissue parameters; temperature, thickness of vessel wall, diameter of blood vessel, rate of blood flow. FIG. 7E illustrates a relative increase in tissue parameters; temperature, thickness of vessel wall, diameter of blood vessel, rate of blood flow. Catheter 1222 having ultrasonic emission element 300 is located inside blood vessel 1242. Ultrasound is used to treat target tissue 1216 surrounded by tissue 1304. Blood 1302 is flowing through vessel 1342.

In some embodiments of the invention, the temperatures of one or more of blood 1302, surrounding tissue 1304 and/or target tissue 1216 are adjusted, for example, to one or more different temperatures. Optionally, the temperature of one or more tissues is relatively increased (shown as T1), for example, by 0.2 degrees Celsius, or 0.5 or 1 or 2 or 5 or 10 degrees Celsius above body temperature, or other smaller, intermediate or larger values are used. Alternatively or additionally the temperature of one or more tissues is relatively reduced (shown as T2), for example, by 0.2 degrees, Celsius, or 0.5 or 1 or 2 or 5 or 10 or 20 or 30 or 35 degrees Celsius below body temperature or other smaller, intermediate or larger values are used. Non-limiting options of adjusting the temperature include: inserting the patient and/or region of the body into a solution of relatively cooler or relatively hotter liquid, blowing cold or hot gas (e.g., room air) on the patient, infusing relatively cold or relatively hot liquid (e.g., saline) into the patient. Exemplary reasons for changing the temperature of tissues will be described below.

In some embodiments of the invention, the thickness of the arterial wall is adjusted. Optionally, the arterial wall is maintained and/or expanded (if in a contracted state). Optionally or alternatively, the arterial wall is contracted, for example, by about 10%, about 20%, about 30%, or other smaller, intermediate or larger values. The rate of evacuation of heat from surrounding tissues 1304 and/or target tissue 1216 can be related to contraction and/or expansion of the arterial wall. For example, expanding and/or relaxing the arterial wall can cause a dilation of the vasa vasorum, thereby increasing blood flow and the evacuation of heat. For example, contraction of the arterial wall can cause contraction of the vasa vasorum, thereby decreasing blood flow and the evacuation of heat.

In some embodiments, the entire circumference of the vessel is adjusted. Alternatively, an arc of the circumference of the vessel is adjusted, for example, about 10, 15, 30, 45, 60, 90 degrees, or other smaller, intermediate or larger values are adjusted. One part (e.g., arc) of the vessel around the circumference is adjusted, for example, 2, 3, 4 or other smaller, intermediate or larger numbers of areas around the circumference. Optionally, the adjusted areas correspond to the treatment areas.

In some embodiments, a portion of the blood vessel length is adjusted. For example, about 5 mm, about 10 mm, about 20 mm, about 30 mm, about 50 mm, about 100 mm, or other smaller, intermediate or larger values are used. Alternatively, areas substantially larger than the blood vessel itself are affected, for example, an organ, a limb, the entire body, the entire vasculature.

In some embodiments, the volume of the adjusted tissue corresponds to the selected volume of the desired effect. Optionally, the target tissue is within the adjusted tissue. For example, the volume of adjusted tissue is about 100%, 150%, 200%, 500%, 1000%, 10000% of the volume of the desired effect, or other smaller, intermediate or larger values are used.

In some embodiments of the invention, the rate of evacuation of heat from one or more of blood 1302, surrounding tissues 1304 and/or target tissue 1216 are adjusted, for example, by varying amounts. Optionally, the rate of evacuation of heat is relatively increased. Alternatively or additionally, the rate of evacuation of heat is relatively decreased.

In some embodiments of the invention, flow of blood 1302 through vessel 1242 is adjusted. Optionally, a relatively higher rate of blood flow 1302 (shown as long arrows) relatively increases the rate of heat removal. Optionally or additionally, a relatively lower rate of blood flow 1302 (shown as short arrows) relatively reduces the rate of heat removal. The effect of heat removal, such as on the area of damage, has been described with reference to FIGS. 7A-7C.

Non-limiting examples of methods to adjust the rate of blood flow 1302 include:

Increasing or decreasing the cardiac output, for example, by artificially pacing the heart (e.g., external pacemaker) to a relatively higher or relatively lower rate, for example, to 120, 150, 180, 200 beats per minute or other smaller, intermediate or larger values.

Dilating blood vessel 1242 (shown as d1), such as by administration (e.g., into the vasculature) of vasodilatory agents such as nitrates (e.g., nitroglycerin) and/or agents to relax the muscles of arterial wall 1242, such as muscle paralyzing agents such as botulinum (blocks release of acetylcholine). Agents can be delivered locally and/or systemically. Electricity can also be applied in a pattern and/or settings (e.g., long DC signal) that relaxes the arterial wall.

Constricting blood vessel 1242 (shown as d2), such as by administration of vasoconstricting agents such as alpha-1 agonists (e.g., phenylephrine), by applying an electrical current to cause muscle contraction in arterial wall 1242, and/or by mechanically agitating tissues (e.g., traumatizing) to cause constriction.

In some embodiments of the invention, the absorption to applied ultrasound energy of one or more of blood 1302, surrounding tissues 1304 and/or target tissue 1216 are adjusted, for example, by varying amounts. Optionally, the absorption is relatively increased (shown as TR). A non-limiting example of relatively increasing the absorption to ultrasound is by injecting a material that absorbs ultrasound energy to a relatively higher degree, such as microbubbles.

In some embodiments of the invention, tissue properties are adjusted in accordance with the selected safety parameters, for example, to relatively increase the margin of safety. Optionally, the rate of heat removal from surrounding tissues 1304 is relatively increased, for example, as described herein. Alternatively or additionally, the temperature of tissues 1304 is relatively reduced, for example, as described herein. A potential advantage of increasing the rate of heat removal and/or reducing the temperature is reducing damage to surrounding tissues 1304, for example, as described with reference to FIGS. 7A-7C.

In some embodiments of the invention, tissue properties are adjusted in accordance with the selected damage profile, for example, to relatively increase the area of damage. Optionally, the ability of surrounding tissues 1304 to absorb ultrasound energy is relatively increased, for example, as described herein. Alternatively or additionally, the temperature of tissues 1304 is relatively increased. A potential advantage of increasing the temperature and/or acoustic absorption is increasing the thermal effect of the applied ultrasonic energy, for example, as described with reference to FIGS. 7A-7C and/or FIG. 9. For example, if the tissue temperature is increased and/or the rate of heat removal is decreased, the thermal effects resulting from an amount of acoustic energy can be relatively increased.

Time Insensitive Damage

FIG. 21 illustrates forming time insensitive damage regions, in accordance with an exemplary embodiment of the invention. In an exemplary embodiment of the invention, the formation of the region of tissue damage is insensitive of the time of application of US energy within a range of times. Alternatively or additionally, the damage caused to nerves is independent of the time of application of US energy within the time range.

In an exemplary embodiment of the invention, US energy is applied for a time period falling within a predefined range creates similar damage areas. For example, the range is a period of time between about 10 seconds and about 30 seconds, or between about 10 seconds and about 20 seconds, or between about 20 seconds and about 30 seconds, or between about 5 seconds and 60 seconds, or between about 1 second and 60 seconds, or between about 10 seconds and 120 seconds, or other smaller, intermediate or larger periods of time. In some cases, US energy applied in less time than the range is insufficient to cause the selected area of thermal damage.

In an exemplary embodiment of the invention, the time insensitive region is formed by application of time of at least a factor of 1:1.5, or at least 1:2, or at least 1:3, or other smaller, intermediate factors. For example, a factor of 1:2, the time ranges from about 5 seconds to about 10 seconds, or about 10 seconds to about 20 seconds, or about 20 seconds to about 40 seconds, or other smaller, intermediate or larger times.

In a schematic representation, US emission element 300 (on catheter 1222) applies US beam 2106 to arterial wall 1242 (e.g., renal artery). Optionally, a selected region of damage is formed 2108 by transfer of sufficient US energy. In some cases, region 2108 contains one or more nerves 2110 (e.g., renal artery nerves).

In an exemplary embodiment of the invention, transfer of heat (shown by arrows 2112) from region 2108 and/or tissue in the path of US beam 2106 to tissues outside US beam 2106 is selective controlled. Optionally, the transfer of heat is balanced so that the heat transfer does not result in raising temperatures sufficiently high to cause thermal damage to nerves. For example, no more than about 47 degrees Celsius.

In an exemplary embodiment of the invention, control of the transfer of heat 2112 is achieved by controlling the blood flow in the blood vessel, for example, blood flow 2104 close to the surface of the arterial wall. Optionally, the transfer of heat is controlled without raising the temperature of blood flow 2102 across the surface of emission element 300 beyond the safe level. Some examples of additional methods of controlling blood flow and/or other methods of controlling heat transfer are described for example, in the section "ADJUSTING TISSUE PROPERTIES".

In an exemplary embodiment of the invention, increasing the time of application of US energy within the time range does not significantly increase the size of damage region 2108. For example, once thermal region 2108 has been formed, applying US energy for an additional time within the range does not significantly increase the size of 2108. For example, region 2108 increases in size (e.g., one dimension) by no more than about 5%, about 10%, about 20%, about 33%, or other smaller, intermediate or larger sizes. Optionally, the additional time independent US energy is delivered with the same parameters (e.g., frequency, intensity). Alternatively or additionally, increasing the time of application of US energy within the time range does not significantly increase the temperature of damage region 2108. For example, the temperature does not increase more with higher times to damage more tissue.

In an exemplary embodiment of the invention, increasing the time of application of US energy does not significantly increase damage to nerves 2110 within region 2108. Optionally or additionally, increasing the time of application of US energy does not significantly increase damage to nerves 2114 outside region 2108. In some embodiments, region 2108 refers to, for example, an area of connective tissue having been denatured by the US energy. In another example, nerves 2114 lie outside US beam 2106.

In an exemplary embodiment of the invention, increasing the time of application of US energy does not significantly reduce NE levels at 30 days following treatment. For example, NE levels within the range of time treatment differ by no more than about 5%, about 10%, about 20%, about 30%, or other smaller, intermediate or larger percentages.

In an exemplary embodiment of the invention, treating tissues using the time insensitive method allows for the formation of the selected thermal damage regions even if the US emission element needs to be turned off, for example, to cool. In one example of a practical situation, the US emission element emits US at the arterial wall to form the selected area of damage. The controller automatically monitors the blood temperature (e.g., blood passing over the surface of the US element). If the blood temperature rises past the safety threshold and/or faster than a safe rate, the controller automatically turns off the US element (e.g., a fast rising temperature can indicate that the US emission element is touching the vessel wall). Temperature is monitored before the US emission elements starts and/or during use. For example, if the temperature rises above, for example, 42 degrees Celsius, or 45 degrees, or 47 degrees, or 51 degrees, or 53 degrees, or other smaller, intermediate or larger temperatures. For example, if the temperature is rising faster than about 2 degrees Celsius/second, or about 5 degrees Celsius/second, or about 10 deg/sec, or about 20 deg/sec, or other smaller, intermediate or larger rates. Optionally, the user is warned if the blood temperature does not rise by at least 1-5 degrees within the first 1-10 seconds, for example, possibly indicating insufficient transmission of US energy.

In an exemplary embodiment of the invention, the US element is cooled faster by the blood than the tissue. Optionally, the US element is turned back on after the temperature has dropped past the set threshold. In some cases, the US element is turned off multiple times during treatment of a single area. Optionally, the operator is not alerted to the turning off of the US element, unless, for example, the time off is sufficiently long to affect the formation of the thermal region, for example, over 2 seconds, or over 10 seconds, or over 20 seconds, or other smaller, intermediate or larger values.

Selective Nerve Damage Outside Damage Region and Exemplary Blood Flow Control Device FIG. 22 illustrates selectively treating nerves outside the region of damage and/or outside the US beam, in accordance with an exemplary embodiment of the invention. Optionally, the nerves are damaged without damaging surrounding tissue, for example, without damaging collagen.

In a schematic representation, US emission element 300 (on catheter 1222) applies US beam 2206 to arterial wall 1242 (e.g., renal artery) to form a region of thermal damage 2208. In some cases, region 2208 contains one or more nerves 2210 (e.g., renal nerves).

In an exemplary embodiment of the invention, transfer of heat (shown by arrows 2212) from region 2208 and/or tissue in the path of US beam 2206 to tissues outside US beam 2206 is selective controlled. Optionally, the transfer of heat is balanced so that the heat transfer raises the tissue to a temperature sufficient to cause damage to nerves (e.g. over about 47 degrees Celsius), but not to a temperature sufficient to cause damage to surrounding tissues, for example, denaturation of surrounding collagen (e.g., below about 50 degrees Celsius, or about 55, or about 60, or other smaller, intermediate or larger temperatures). Optionally, the nerve damage occurring at 47 degrees Celsius is not visible when viewed on a histologically prepared slide stained to show other types of damage, for example, collagen denaturation (e.g., H&E stain).

In an exemplary embodiment of the invention, the selective nerve damage is obtained by control of blood flow through the vessel. Optionally, blood flow 2204 across and/or close to the surface of the artery is slowed down. Optionally or additionally, blood flow 2202 across and/or close to the surface of emission element 300 is not slowed down significantly so as to affect the temperature of blood flow 2202. For example, the temperate of blood flow 2202 is maintained below the safe level. Without being bound to theory, slowing blood flow 2204 reduces the cooling of the tissues of the arterial wall and/or surrounding tissues so that relatively more heat 2212 is transferred.

A not necessarily limiting example of a treatment protocol for selectively treating nerves comprises:

Selecting a safe target, for example, nerves in the renal artery wall and avoiding the intima. In an exemplary embodiment of the invention, the safe target is selected in the body to be away from vulnerable structures, so that damage to the target does not spread to adjacent structures. For example, the safe target is selected away from blood vessel walls to prevent thrombus, emboli, dissections, aneurysms.

Heat the safe target for a period of time to selectively damage the target. For example, heat for a period of time of about 10 seconds, about 20 seconds, about 30 seconds, about 60 seconds, or other smaller, intermediate or larger times. In some cases nerves are damaged to preventing signal conduction or reduce signal conduction. In some cases nerves are damaged on a temporary or permanent basis.

In some embodiments, the temperature of the target and/or surrounding tissue is monitored, for example, by a temperature sensor. In such a case, the target is heated for a time period until the nerve damaging temperature is reached (e.g., above about 47 degrees Celsius).

Optionally, in some embodiments, the tissues are preheated a bit, for example, by 1 degree Celsius, by 3 degrees Celsius, by 5 degrees Celsius, or other smaller, intermediate or larger values are used. Optionally, the tissue around the safe target is heated. Alternatively, the patient's body is heated. Some not necessarily limiting methods of heating tissues include; applying an active heating blanket over the patient, injecting heated saline into the blood, applying US or other energy to the vessel wall at settings only strong enough to slightly heat the tissue and not cause damage, or other methods of heating as described herein.

In practice, the preheating can be performed in areas with high blood flow that would otherwise excessively cool the target tissue.

Stop or slow down blood flow near the treatment area. In an exemplary embodiment of the invention, the blood is stopped or slowed down for no more than about 1 second, or about 3 seconds, or about 5 seconds, or about 10 seconds, or about 20 seconds, or about 30 seconds, or for the time it takes to apply a plurality of treatments or other smaller, intermediate or larger time periods. In an exemplary embodiment of the invention, slowing down blood flow occurs for the same time period as application of US energy. Alternatively, blood flow is slowed down before the application of US, for example, to achieve a selected flow rate. Alternatively or additionally, blood flow is slowed down after US energy has been applied for a period of time.

In some embodiments, the temperature of the blood flow and/or target tissue and/or surrounding tissue is monitored, and the blood flow is stopped until the selected nerve damaging temperature is obtained.

Reposition catheter and repeat the process of heating the target and slowing down blood flow. Alternatively, blood flow is slowed down for the time it takes to apply a plurality of treatments.

In an exemplary embodiment of the invention, blood flow is controlled by one or more extensions of catheter 1222, for example, one or more protrusions 2220 over the surface of catheter 1222. Alternatively, one or more different devices can be used to control blood flow, for example, attached to the catheter and/or separately insertable (e.g., through the catheter lumen). Optionally, the blood flow control element is located downstream (e.g., blood flow direction) of US element 300. Alternatively or additionally, the blood flow control element is located upstream of US element 300.

In an exemplary embodiment of the invention, the blood flow control element is sized, positioned and/or shaped to slow down and/or stop blood flow close the vessel wall near the target tissue, but the element still allows enough blood flow over US emission element 300 to maintain a safe temperature. For example, blood flow is slowed down or stopped within about 0.5 mm from the inner vessel wall, or within about 0.7 mm, or within about 1 mm, or within about 1.3 mm, or within about 1.5 mm, or other smaller, intermediate or larger distances. For example, blood flow close to the vessel wall is slowed down by 100% (e.g., stopped), or slowed down by about 80%, about 70%, about 50%, or other smaller or intermediate percentages. For example, blood flow over the US element 300 is not slowed down by more than about 20%, or about 30%, or about 50%, or other smaller, intermediate or larger percentages.

In some embodiments, a distal end 2216 of catheter 1222 contains one or more protrusions 2220 above the planar surface of catheter 1222. Protrusions 2220 can be placed upstream and/or downstream of US element 300. In an exemplary embodiment, there are 4 protrusions 2220 around the circumference of catheter 1222, but other numbers are possible, for example, 1, 2, 6, 8 or other smaller, intermediate or larger numbers of protrusions 2220. Protrusions can be equally spaced apart, for example, 90 degrees apart, or the spacing can be unequal.

In some embodiments, protrusions 2220 are made from a suitable material that is biocompatible and/or optionally smooth, for example PTFE.

In some embodiments, at least two protrusions 2220 are positioned.

In some embodiments protrusions 2220 are curved, but other shapes of arcs 2220 can be used, for example, triangular (e.g., flat as opposed to curved).

In some embodiments, one or more protrusions 2220 are positioned on opposite sides of US element 300 (and/or upstream and/or downstream along the parallel line) so that blood 2202 is able to flow between protrusions 2220 (e.g., to cool element 300) and blood flow 2204 is at least partially disrupted by protrusions 2220 (e.g., to control the cooling of the vessel wall). Optionally, one or more protrusions 2220 are located approximately opposite element 300, for example, to assist in anchoring catheter 1222 within the vessel.

In some embodiment, a gap between the two protrusions 2220 paralleling US element 300 is selected according to the desired blood flow 2202 rate. Optionally, increasing the gap size increases blood flow 2202 rate and decreasing the size decreases the rate. In some embodiments, the gap is dynamically adjustable and/or controllable, for example, by a wire, for example, manually by the user or automatically by a controller. The size of gap, is for example, about 1 mm, or about 2 mm, or about 4 mm, or about 5 mm, or about 7 mm, or about 10 mm, or about 12 mm, or about 15 mm, or other smaller, intermediate or larger sizes. Alternatively or additionally, the size of gap is, for example, about 50% the width of US element 300, or about 75%, or about 100%, or about 125%, or about 150%, or about 200% of the width.

In some embodiments, the height of protrusions 2220 (e.g., perpendicular to catheter 1222) is selected so that the largest dimension of protrusions 2220 (e.g., from opposite sides) is less than the diameter of the vessel, for example, if the renal artery is about 5 mm in diameter, the largest dimension is about 4 mm. For example, the largest dimension is about 3 mm, or about 4 mm, or about 5 mm, or about 6 mm, or other smaller, intermediate or larger dimensions. For example, the largest dimension is about 100% or about 90% or about 80% or about 70% or about 50% of the diameter of the vessel. In practice, the diameter of protrusions 2220 less than the diameter of the vessel allows for rotation within the vessel. In practice, the diameter of protrusions 2220 about equal to the diameter of the vessels helps in stabilizing the catheter within the vessel.

In some embodiments the curvature and/or height of protrusions 2220 is adjustable, for example, by adjusting the length of a perpendicular radius, such as by pulling an adjustment member (e.g., wire 2218). Potentially adjusting protrusions 2220 controls blood flow 2204. In some embodiments, increasing height of protrusions 2220 further blocks the cross sectional area of the blood vessel to slow down blood flow 2204, and decreasing height increases blood flow

2204. In some embodiments, expanding protrusions 2220 to the diameter of the vessel allows for anchoring of catheter 1222 inside the vessel against the walls. Optionally, the force exerted to anchor against the vessel wall is insufficient to damage the walls.

FIGS. 24A-C illustrate some other examples of blood flow control elements, in accordance with an exemplary embodiment of the invention.

FIG. 24A illustrates the use of one or more inflatable balloons 2406 as the blood flow control element. In some embodiments, balloon 2406 inflates to block or slow down blood flow 2404 next to vessel wall 1242. Optionally, balloon comprises one or more holes 2408 positioned next to catheter 1222 surface, to not significantly slow down blood flow 2402 over US element 300. In some embodiments, the degree of inflation of balloon 2406 is used to select the degree of slowing down of blood flow 2404.

FIG. 24B illustrates the use of one or more sails 2410 as the blood flow control element. In some embodiments sail 2410 comprises one or more holes 2416 positioned to selectively slow down blood flow 2414 next to vessel wall 1242 but allow sufficient blood flow 2412 over US element 300 to cool element 300. In some embodiments, sail 2410 is made of, for example, PTFE and/or braided nitinol. In some embodiments retraction of sail (e.g., by a wire) selectively controls the degree of slowing down of blood.

FIG. 24C illustrates the use of one or more walls 2420 as the blood flow control element. In some embodiments, wall 2420 is positioned to disrupt blood flow 2422 through the vessel, creating blood turbulence 2424 (e.g., vortices) that transfers heat from the surface of US element 300 to next to vessel wall 1242. Transfer of the hot blood is used to control the cooling of the target tissue in stead of, or in addition to slowing down the blood flow next to the vessel wall. In some embodiments, wall 2420 is positioned upstream of US element 300. Alternatively or additionally, wall 2420 is positioned downstream of element 300. Walls 2420 can be made of, for example, an inflatable balloon, nitinol, PTFE, or other materials.

Some other examples of blood flow control elements are described with reference to PCT/IB2011/054638 titled "SEPARATION DEVICE FOR ULTRASOUND ELEMENT", incorporated herein by reference in its entirety. Alternatively or additionally, other methods of controlling blood flow and other methods of controlling heat transfer are described for example, in the section "ADJUSTING TISSUE PROPERTIES".

In an exemplary embodiment of the invention, blood flow is adjusted to selectively reduce kidney NE levels. For example, as described in "SELECTIVE REDUCTION OF NERVE ACTIVITY" (U.S. provisional application 61/590,423), incorporated herein by reference in its entirety.

Potentially, some nerves are damages without causing damage to surrounding tissues.

Selecting Parameters—Example of Choosing Catheter (Frequency) According to Treatment FIG. 8 is an exemplary illustration of a simplified estimate of the effect of frequency of ultrasound energy on an area of damage, in accordance with an exemplary embodiment of the invention.

The top part of FIG. 8 illustrates an ultrasound transducer 806 emitting ultrasound energy towards an arterial wall 812. Non-limiting examples of the ultrasound energy include 20 Mhz ultrasound energy 808 and/or 10 Mhz ultrasound energy 810.

The bottom part of FIG. 8 illustrates the attenuation of energy 808 and/or 810 by the tissues of wall 812. As illustrated by the table in the section "ESTIMATE BLOOD FLOW", attenuation of ultrasound energy by tissue is inversely proportional to frequency. An exemplary attenuation graph for 20 Mhz 816 shows relatively higher attenuation relatively closer to a lumen 818. In some embodiments, an area of damage 802 is relatively closer to lumen 818. An exemplary attenuation graph for 10 Mhz 814 shows relatively lower attenuation as a function of distance from lumen 818. In some embodiments, an area of damage 810 is relatively further from lumen 810.

In an exemplary embodiment of the invention, the frequency of ultrasound energy used for selectively targeting tissue is selected according to the treatment plan. For example, target tissue relatively further from the lumen and/or from the intima layer is selectively treated by using a relatively lower frequency of ultrasound energy.

In an exemplary embodiment of the invention, the frequency of the ultrasound energy used for treatment is selected, for example to be about 5 Mhz, about 8 Mhz, about 10 Mhz, about 15 Mhz, about 8 Mhz-15 Mhz, about 20 Mhz, about 10 Mhz-20 Mhz, about 30 Mhz, or other smaller, intermediate or larger frequencies. IN some cases, et frequency will be substantially narrow band, for example, less than 30%, 20%, 10%, 5% of the application frequency. Optionally or alternatively, a wide band or multi frequency signal is used, for example, with 2, 3, 4, 5 or more discrete frequencies and/or with a range of, for example, 1 Mhz, 3 Mhz, 5 Mhz or smaller or intermediate widths.

In an exemplary embodiment of the invention, for example for renal denervation, a lower frequency may be used to achieve a higher reduction in norepinephrine levels.

In an exemplary embodiment of the invention, the signal parameters are selected according to a desired functional effect, in addition to or instead of according to a desired structural effect (e.g., tissue ablation).

In an exemplary embodiment of the invention, a catheter is selected according to the frequency of the selected ultrasound energy. Optionally, the acoustic element on the transducer is designed to vibrate at the treatment frequency. For example, the thickness of the acoustic element is related to the expected frequency of vibration of element, optionally linearly related, for example, a thickness of 100 micrometers for a frequency of 20 Mhz, a thickness of 200 micrometers for a frequency of 10 Mhz.

Selecting Parameters—Choosing an Ultrasonic Intensity Profile According to Treatment FIG. 9 is an exemplary illustration of a simplified estimate of the association between an ultrasonic intensity profile and damaged areas, useful in practicing some embodiments of the invention.

In an exemplary embodiment of the invention, the ultrasonic intensity profile for treatment is selected. Optionally, the ultrasonic intensity profile is related to the ultrasonic intensity emitted by the acoustic element (e.g., in watts per square centimeter) over time (e.g., in seconds), for example, relatively longer times relatively increase the ultrasonic intensity profile, for example, relatively higher acoustic intensities relatively increase the ultrasound intensity profile. Optionally or additionally, the ultrasonic profile is selected to vary over time. In some embodiments, the ultrasonic profile is associated with the total amount of ultrasonic energy delivered to the tissues. In some embodiments, the profile is substantially a temporal square wave. Optionally or alternatively, the profile is substantially a spatial square wave (e.g., sharp cut-offs at the edges of the beam), in one or two dimensions.

FIG. 9 shows an ultrasound transducer 902, emitting ultrasonic energy at various intensity profiles, for example, a relatively low intensity profile 904, a relatively medium intensity profile 906 and/or a relatively high intensity profile 908.

In some embodiments, the area of damage begins relatively far from an intima 916, for example, at a periadventitia 918. In some embodiments, the area of damage increases towards the intima with relatively increased ultrasonic intensity profiles.

In an exemplary embodiment of the invention, tissues relatively closer to the blood cool relatively faster. In an exemplary embodiment of the invention, a treatment plan comprising of a series of pulses with a delay between the pulses will have a greater cumulative effect away from the wall. In an exemplary embodiment of the intervention, a treatment plan of pulses with delays causes an effect to tissues relatively further away from the wall, without causing a thermal effect to tissues relatively closer to the wall.

In an exemplary embodiment of the invention, the extent of damage is settable according to the ultrasound intensity profile, such as 904, 906 and/or 908. For example, damage is localized to target tissue 910 (e.g., no damage to surrounding tissue). For example, an area of damage 912 extends somewhat beyond target tissue 910. For example, a relatively large area of damage 914 extends a relatively larger area beyond target tissue 910.

In an exemplary embodiment of the invention, the extent of damage is selected to not reach intima 916.

Insert Catheter

In an exemplary embodiment of the invention, catheter 1222 (e.g., as shown in FIG. 5) in inserted into the body of a patient. Standard vascular access methods can be used, for example, from the femoral artery. Optionally, catheter 1222 is threaded using a guidewire 1202 (e.g., over the wire, rapid exchange, "buddy" wire) to the target treatment site (e.g., an artery such as the iliac, renal, carotid, aorta) under image guidance, such as fluoroscopy. Alternatively or additionally, catheter 1222 is directed inside a guiding sheath, for example to protect the ultrasound transducer from mechanical damage during delivery to the target site. Alternatively or additionally, catheter 1222 is directed inside a guiding catheter.

In an exemplary embodiment of the invention, catheter 1222 is guided during delivery using imaging, for example fluoroscopic image.

Referring back to FIG. 5, in an exemplary embodiment of the invention, element 102 on catheter 1222 is prevented from contacting vessel wall 1226, for example, by using separation device 1204. Details about separation device are provided with reference to U.S. Provisional Application No. 61/453,234, incorporated herein by reference in its entirety. Optionally, element 102 contacts wall 1226 if treatment parameters are set and/or adjusted accordingly, for example, if element 102 is sufficiently cooled and/or if the intensity profile is reduced.

In an exemplary embodiment of the invention, distance 1218 (between element 102 and wall 1226) does not have to be taken into account for setting treatment parameters. Optionally distance 1218 varies during treatment. In some embodiments, the attenuation of ultrasonic beam 1228 by blood flow 1220 is relatively insignificant.

A potential advantage of preventing contact between element 102 and wall 1226 is reducing or preventing damage to the endothelium, basal membrane and/or internal elastic lamina.

In some embodiments of the invention, catheter 1222 includes one or more elements to move transducer 300. Optionally, the element is a piezoelectric element that can be vibrated by applying electrical power. Alternatively or additionally, the element moves transducer 300 for relatively fine positioning, for example, an electrically controlled motor. In some embodiments, the element vibrates and/or moves transducer 300 to position the strongest part of the ultrasound beam at the target tissue.

In some embodiments the controller can be calibrated according to the expected intensity profile of the produced ultrasound beam, for example, the controller vibrates and/or moves transducer 300 in order to obtain a desired position for thermally affecting the tissues.

Treat

FIG. 10 is a flow chart of monitoring during treatment, in accordance with an exemplary embodiment of the invention. In some embodiments, monitoring is a type of feedback associated with the parameters affecting treatment.

At 1002, the target tissue is treated. The ultrasound transducer emits ultrasound energy towards the target tissue at the selected acoustic intensity profile and/or at the selected frequency.

In an exemplary embodiment of the invention, the target tissue can be treated according to the selected treatment plan (e.g., acoustic intensity profile, frequency) without requiring monitoring and/or feedback.

Optionally, at 1004, monitoring of the treatment is performed.

In some embodiments of the invention, monitoring occurs at the same time as treatment is occurring (e.g., in parallel with the treatment). Alternatively or additionally, treatment (e.g., transmission of ultrasonic energy) occurs in pulses separated by a delay, with the monitoring occurring during the delay. Optionally, monitoring is carried out continuously during the entire treatment.

Optionally, at 1006, the environment surrounding the treatment procedure is monitored. In some embodiments, changes in environmental conditions affect the treatment if the treatment parameters remain unchanged. For example, if blood flow is increased without changing the treatment parameters, the treatment may not be effective due to the increased rate of cooling. In some embodiments, changes in environmental conditions are taken into account when adjusting treatment parameters, for example, if an increase in blood flow is detected, the intensity profile is increased accordingly to achieve the desired effect in the selected tissues.

In some embodiments, the temperature of the blood flow is monitored, for example, by a sensor placed downstream from the transducer.

Optionally, at 1008, the integrity of the transducer is monitored. In some embodiments, changes in the integrity suggest one or more causes such as blood clots on the transducer, overheating of the transducer, mechanical damage. In some embodiments, changes in the integrity of the transducer are monitored to prevent adverse events. Optionally, the treatment parameters are adjusted according to the integrity. For example, if the transducer comes closer to the wall or contacts the wall, potentially the intima can overheat, resulting in thermal damage to the intima if the treatment parameters are not adjusted accordingly (e.g., increased cooling, reducing the intensity profile).

In some embodiments, the integrity of the transducer is monitored by measuring changes in the impedance, for example, a change greater than 3%, 5%, 10%, 20%, or other smaller, intermediate or larger percent changes.

In some embodiments, the integrity of the transducer is monitored by measuring the distance from the transducer to the arterial wall (e.g. to the intima). Optionally, the distance is measured by a returning echo. Alternatively or additionally, the distance is measured on x-ray images.

Feedback

In some embodiments of the invention, acoustic energy is applied to the target tissue in an open loop manner. For example, the target is set and the target is met, without using feedback. Alternatively, acoustic energy is applied to the target tissue in a closed loop manner, such as with feedback.

In some embodiments, feedback is a measure of the physical effect of the treatment on the tissue. Optionally or alternatively, feedback is a functional measurement. In some embodiments, feedback is provided on the transmission of the energy and/or parameters of the emitter and/or catheter (e.g., distance), in addition to or instead of on the target tissue. While, in an exemplary embodiment of the invention, feedback is during the procedure, possibly during a single application of energy (e.g., within less than 30 seconds), in some embodiments, feedback is on longer time scales, such as 1-3 minutes (e.g., between applications and/or after a set of applications is provided) or days or more.

FIG. 11 is a flow chart showing optional functional feedback associated with treatment, in accordance with an exemplary embodiment of the invention.

Optionally, at 1102 feedback is obtained about the results of the treatment.

Optionally, at 1104, functional feedback is obtained about the effect of treatment on tissues. Optionally, imaging is performed of the target tissue to detect and/or estimate the extent of therapy. Alternatively or additionally, imaging is performed of the surrounding tissue to detect and/or estimate the extent of damage (e.g., margin of safety). In some embodiments, some changes (e.g., due to denaturation of collagen) are detected as they happen. In some embodiments, some changes are detected after a period of time (e.g., several days), for example, anatomical changes secondary to the inflammatory response, such as fibrosis.

In some embodiments, imaging is performed by the using the same ultrasound transducer used for treatment, for example, by treating at a first treatment frequency for a period of time, then imaging at a second diagnostic frequency for another period of time (e.g., analyzing the ultrasonic echoes returning from the tissues). Alternatively or additionally, the same ultrasound transducer is used, but with different electrodes which separate the transducer into an imaging region and a treatment region. Alternatively or additionally, one or more acoustic elements are used, for example, one element for imaging and one element for treatment.

In some embodiments, one or more other imaging modalities are used instead or in addition to the element, such as CT, MRI, x-ray.

One or more non-limiting examples of ultrasound imaging methods for feedback include, Measuring the ultrasonic attenuation of the target tissues, for example, as described by Damianou et al, J Acoust Soc Am. 1997 July; 102(1):628-34, incorporated herein by reference in its entirety. Damianou found that the rate at which the thermal dose was applied was associated with the total attenuation absorption, for example, relatively lower thermal dose rates resulted in relatively larger attenuation coefficients. In some embodiments, the intensity profile that is applied to the target tissues is estimated by measuring the attenuation coefficient and/or the absorption. Optionally, the measurements are compared to expected values according to the set intensity profile. Optionally or additionally, the intensity profile is adjusted relatively higher or relatively lower according to the comparison, for example, to achieve the resulting thermal damage to the target tissue.

Measuring the ultrasound attenuation coefficient and/or backscatter power for example, as described by Worthington, A. E., et al, Ultrasound in Med. & Biol., Vol. 28, No. 10, pp. 1311-1318, 2002, incorporated herein by reference in its entirety. Worthington found that the attenuation coefficient and/or backscatter power increased with relatively higher temperatures. In some embodiments, the temperature of the target tissues is estimated according to the attenuation coefficient and/or backscatter power. Optionally, the temperature of the tissue is compared to the temperature range and/or threshold required to achieve a desirable effect in the tissues (e.g., collagen denaturation above 55 degrees Celsius). Optionally or additionally, the intensity profile is adjusted relatively higher or relatively lower according to the comparison, for example, to achieve the target temperature in the target tissue.

Optionally, at 1106, feedback consists of clinical effects, for example, desired clinical effects, adverse clinical effects, lack of clinical effects.

In some embodiments, clinical measurements are used as feedback. For example, the results of renal denervation to treat persistent hypertension can be measured by one or more of, blood pressure, norepinephrine spillover, norepinephrine levels, renal artery blood flow.

In some embodiments of the invention, the distance from the acoustic element to the arterial wall is measured, optionally continuously measured. Optionally, the distance is measured using the acoustic element itself, for example, as described in co-filed PCT applications PCT/IB2011/054636 and/or PCT/IB2011/054639, incorporated herein entirely by reference. In some embodiments, the distance is used as feedback to prevent high power operation of the acoustic element while touching the arterial wall, for example, if the distance is measured to be zero (e.g., contact) or relatively close to contact (e.g., 0.1 mm, 0.3 mm or other smaller, intermediate or larger distances), the power to the transducer can be reduced and/or shut off. A potential advantage of measuring the distance using the element is a relatively more accurate measurement of the distance as compared with measuring the distance from angiographic images.

Adjust

In some embodiments of the invention, monitoring of the treatment and/or feedback of the treatment can increase the level of control of the treatment (e.g., in real time, overall effect over several treatment sessions). Optionally, desired clinical results are achieved by the treatment.

In some embodiments, data from feedback and/or monitoring is used to adjust treatment parameters (e.g., frequency, ultrasonic intensity profile), for example, by a look-up table (e.g., stored in a memory), calculations, trial and error (e.g., slowly changing a parameter and/or monitoring changes). Optionally, parameters are adjusted manually (e.g., by a user) using an interface coupled to a controller. Alternatively or additionally, parameters are automatically adjusted, such as by a software module of controller.

One or more non-limiting examples of adjustments include, increasing the treatment, reducing the treatment, stopping the treatment.

A non-limiting example to illustrate the concept of adjusting variables according to measurements is provided:

A patient with resistant essential hypertension was proposed treatment by a renal denervation procedure. A renal nerve surrounded by fat located about 4 mm away from the renal vessel wall in the peri-adventitia was targeted for treatment. A catheter designed for a frequency of 10 Mhz was selected (e.g., due to the relative distance away from the wall) and an initial intensity of 30 watt/cm^2 was selected based on standard blood flow rates expected (e.g., according to a look-up table of patient profiles). The catheter was inserted into the renal artery. A pulse of duration 1 second was used to initially treat the vessel wall for calibration purposes. Imaging results indicated that the area of damage was located 15 degrees clockwise, and 5 mm away from the wall. Based on the results, the catheter was manually rotated 15 degrees towards the target. Treatment started again, using a pulse of 30 seconds duration. About 5 seconds into treatment, the cardiac output of the patient suddenly increased, causing a 50% increase in the rate of blood flow through the renal artery. The controller automatically increased the intensity profile to 40 watt/cm^2 to offset the increased cooling rate of the tissue wall by the blood. Another calibration pulse of 1 second was applied. Imaging indicated that the nerve was being thermally damaged. Treatment was stopped after 22 seconds, once imaging results indicated that the nerve was fully damaged, along with a tissue margin around the nerve of at least 0.5 mm. The patient was followed in clinic for several weeks to verify the expected treatment effect of a reduction in blood pressure.

In some embodiments of the invention, treatment is synchronized (e.g., at a same time or otherwise timed thereto, such as at a delay after or before) to the adjustments, for example, as will be described at the end of the section "EXEMPLARY DEVELOPMENT OF AN EQUATION—Part B"

Exemplary Treatment Protocols

The table below describes some possible treatment protocols, in accordance with some embodiments of the invention. Optionally, the 'Effect Location' and/or related "Information" is determined by imaging, for example, as described in the section "FEEDBACK". Optionally, action is taken, such as based on the "Information", for example, by the 'Cardiologist' and/or by the 'System' (for example, the controller, such as using software stored thereon containing the 'algorithm'). Details related to 'Action' can be found for example in the section "ADJUST".

Table of Some Possible Treatment Protocols

| Effect location | Criteria | Subject | Information | Action: Cardiologist | Action: System/algorithm |
|---|---|---|---|---|---|
| Minimal distance of effect from artery lumen | Minimal 1 mm | effect location during treatment | effect area/volume | Reduce energy-change treatment parameters or duration | If distance <1-system stops excitation<br>If distance >10-system alerts-thermal effect is too far |
| Maximal distance of thermal effect from artery lumen | Maximal 15 mm | effect location during treatment | effect area/volume | | If distance >15-system stops excitation |
| Rate of effect formation | | effect location during treatment | Rate of effect formation | Reduce energy-change treatment parameters or duration | If (maximal − minimal distance) difference is higher than 2 mm/sec-system stops excitation |
| | | | | Enable treatment | If (maximal − minimal distance) difference is lower than 2 mm/sec-system enables excitation |
| Location along the artery | | effect location post treatment | effect width in artery length | Decision-Continue Adjust Sufficient | Up to 50% of artery length-system alert for cardiologist decision |
| Location in the artery circumference | | effect location post treatment | effect width in artery circumference | Decision-Continue Adjust Sufficient | Up to 50% of artery circumference-system alert for cardiologist decision |
| Minimal distance of thermal effect from artery lumen | Minimal 1 mm | effect location post treatment | effect area/volume | Decision-Repeat Adjust Sufficient | If thermal effect is too close to lumen (<1 mm)-system suggests cardiologist to add extra anti-coagulation treatment |
| Maximal distance of effect from artery lumen | Maximal 15 mm | effect location post treatment | effect area/volume | | |

The following table shows exemplary activities by the controller and/or operator in various conditions, in accordance with some embodiments of the invention, base on the distance between the ultrasound emitter and the wall. Such distance can be measured, for example, using an external system (e.g., angiography or ultrasound), by processing signals received by the emitter or by a separate ultrasonic element.

| Distance (calculated/measured) | Value (mm) | Subject | Criterion | Cardiologist | System/algorithm |
|---|---|---|---|---|---|
| Distance measurement before treatment | <1.4 | Catheter position before treatment | >1 | Change GC (guide catheter) position Change US transducer angle Change US transducer position along the artery | System alert- short distance System disables excitation until distance is changed according to criterion |
| | >1 | Catheter position before treatment | >1 | Enable excitation | Enable excitation |
| | >5 | Catheter position before treatment | 1 < x < 5 | Too large distance: Confirm possible bifurcation or dislocation with contrast injection and angiography and move US transducer | System alert- bifurcation, change US transducer position |
| | 1 > x > 1.3 Angle between US transducer and artery wall is larger than 10° | Catheter position before treatment | >1 | Unreliable distance- Confirm US transducer angle with contrast injection and angiography: Change GC position | |
| | >1.3 Angle between US transducer and artery wall is larger than 10° (diagonal) | Catheter position before treatment | >1 | Enable excitation | Enable excitation |
| Distance measurement during treatment | <1 | Catheter position during treatment | >1 | Change GC position and complete treatment | System alerts-short distance System stops excitation until distance is changed according to criterion |
| | 0.7 < x < 1 | Catheter position during treatment | >1 | Consider to stop excitation and improve position before completing treatment | System alert- shortening distance |
| | 1 < x < 5 | Catheter position during treatment | >1 | Enable excitation to end | Enable excitation to end |
| | Decreasing distance | Catheter position during treatment | >1 | Possible blood vessel constriction due to treatment- consider stop and nitroglycerin infusion | System alert-decreased distance |
| | >5 Sudden movement | Catheter position during treatment | >1 | | System disabled |
| Vessel blood pulsation analysis | Repetitive changes- Maximal position to minimal position | Pulsation detection before treatment | | | Calculated blood pulsation: If normal, enable excitation |
| | No differences between Maximal position to | Pulsation detection before treatment | | Possible no circulation: Validate flow by contrast injection and angiography | System alert- no pulsation, possible constriction |

-continued

| Distance (calculated/measured) | Value (mm) | Subject | Criterion | Cardiologist | System/algorithm |
|---|---|---|---|---|---|
| | minimal position | | | If needed-infuse with nitroglycerin or cold saline | |
| | distance>1 But no pulsation detection | Pulsation detection before treatment | >1 | Validate flow by contrast injection and angiography If needed- infuse with nitroglycerin or cold saline | System alert- no pulsation, possible constriction |
| Distance measurement, rotate 180°, distance measurement | $1^{st}$-<1 $2^{nd}$-<1 | Artery diameter evaluation | | Possible constriction: Confirm by contrast injection and angiography If needed- inject nitroglycerin and treat | System alert- possible constriction: Disable excitation |
| Distance measurement in 4 angles (90°)- artery diameter calculation | <3 | Artery diameter evaluation | | Check if US transducer is located in the correct artery- using contrast injection and angiography Check for local constriction Possible- Nitroglycerin injection | System alert- possible constriction: Disable excitation |
| | 3 < x < 8 | Artery diameter evaluation | | Enable excitation | Enable excitation |

In an exemplary embodiment of the invention, both kidneys (e.g., renal arteries, renal nerves) are treated. However, this need not be the case. For example, in a follow-up treatment, possibly only a single kidney is treated. Optionally or alternatively, if one kidney is known to be more diseased, that is treated more (e.g., this is a reason for providing a treatment which is asymmetrical between kidneys, this may be done for other reasons as well). Optionally or alternatively, different kidneys are treated a different amount. Optionally, one kidney is intentionally undertreated so as to allow increasing treatment thereof, at a later time.

Potential Advantages of Some Embodiments

Further details of the system described herein can be found in the related applications. For example. "ULTRASOUND EMISSION ELEMENT" (PCT/IB2011/054635) describes an ultrasound emission element. For example, "AN ULTRASOUND TRANSCEIVER AND USES THEREOF" (PCT/IB2011/054636) describes a method for feedback and control. For example, "AN ULTRASOUND TRANSCEIVER AND COOLING THEREOF" (PCT/IB2011/054641) describes cooling of the ultrasonic element. For example, "SEPARATION DEVICE FOR ULTRASOUND ELEMENT" (PCT/IB2011/054638) describes preventing contract between the ultrasonic element and the blood vessel wall. For example, "ULTRASOUND TRANSCEIVER AND USES IN DETECTION" (PCT/IB2011/054639) describes ultrasonic imaging.

Some embodiments have one or more of the following exemplary advantages:
Relatively faster treatment, for example, a treatment duration of 5-30 seconds per treatment region, or other smaller, larger or intermediate ranges can be used.
Relatively small number of treatment regions per artery for renal denervation, for example, 1 treatment region, 3 treatment regions, 4 treatment regions, 6 treatment regions, 8 treatment regions or other smaller, intermediate or larger number of regions are used.
Remote and/or localized effect, for example,
Accurate control of the damage region (e.g., thermal effect) and/or location, such as good control on the location and/or size of the artery tissue damage by therapeutic parameters.
Ability to treat relatively large continuous areas in the arterial wall.
A treatment option for short artery stumps and/or for short total treatment durations (e.g., 5-10 minutes vs 20 minutes for RF treatments).
The effect volume in the tissue is relatively far from the transducer face (e.g., media, adventitia, vasa-vasorum, peri-adventitia, adventitia nerves, peri-adventitia nerves, peri-adventitia capillaries).
Targeting tissues in varying distances from the transducer face according to treatment parameters. For example, applying the effect in tissues located about 5 mm or more from the lumen wall (e.g., intima layer). A relatively far effect is relevant for example, for achieving peripheral nerves blocks from inside the peripheral arteries.
Non-targeted tissues on the beam path to the target tissue are not damaged and/or are selectively damaged (e.g. according to a margin of safety), for example, the endothelium, basal membrane and/or internal elastic lamina
Possibility for varying levels of thermal modulation of the target tissue. For example, partial damage to nerves and/or other target tissues, in a controlled manner and different effect levels. Potentially, partial nerve injury can be controlled, that might lead to nerve recovery, either partially or entirely.
Tissue selectivity, for example, highly selective remote effect in nerve bundles, such as nerves that are covered with thick fat tissue. For example as used in a Renal Denervation procedure in the Renal Artery ostium.

Treatment features suitable for Renal Denervation include:
- The ability to work very close to the renal artery ostium, for example, <10 [mm], or other smaller, intermediate or larger values.
- The ability to work in short arteries, for example, <20 [mm], or other smaller, intermediate or larger values
- The ability to work in small arteries, for example, 4-3 [mm], or other smaller, intermediate or larger values Safety issues
- Relatively safer treatment.
- The temperature of the blood that flows over the ultrasonic transducer can be controlled to not exceed a temperature threshold of 50 degrees Celsius (or other smaller, intermediate or larger numbers) while working in the maximal allowed operation intensity level, for example, 50 [W/cm^2], or other smaller, intermediate or larger intensity levels.
- The temperature of the blood that flows over the ultrasonic transducer can be controlled to not exceed a temperature threshold of over 43 degrees Celsius (or other smaller, intermediate or larger numbers), for example, while working in the therapeutic operation intensity level 30 [W/cm^2], or other smaller, intermediate or larger intensity levels. In some embodiments, there is no need to add external cooling such as by saline injection.
- The therapeutic treatment on the blood vessel wall is done with no mechanical contact with the vessel wall, thereby reducing or eliminating the danger of damaging the vessel wall or disrupting any pathologies on the wall (e.g., atherosclerotic plaques). For example, reducing the risk of arterial perforation and/or mechanical damage that might cause a narrowing in the vessel, plaque tear and/or emboli.
- Localized and/or controlled effects specifically in the targeted treatment volume, preventing and/or reducing non-controlled energy effects in other tissues.
- Blocking of the blood flow during the treatment is optional, and in some embodiments, is not required.
- Treatment of a single artery location (e.g., longitudinally) in one or more circumferential directions, potentially, significantly reducing and/or preventing stenosis.
- Preventing and/or reducing damage to the artery due to repeating treatment 2-3 times (or more) at the same axial position/radial direction, such as due to a mistake.
- Prevent and/or reduce interference with implanted electronic medical devices (e.g., pacemakers, defibrillators).
- Clinical implications, for example, relatively lower pain during treatment as a result of relatively faster blocking of nerves, with no electric excitation of the target nerve and/or no effect on other nerves. Potentially reducing sedation and/or anesthesia.

Relatively shallow learning curve, as leverages existing operator skill sets.

Many applications and/or ability to treat a wide range of clinical disorders.

Treatment option for a wide range of patients, such as high risk populations, for example as those suffering from vascular pathologies. Ability to treat in arteries with plaques and/or stents.

Ability to obtain a partial clinical effect (vs. complete effect). Potentially suitable for patients with milder disease, such as mild hypertension.

Feedback availability during treatment, such as information on the direction and location of the applied energy, catheter and the therapeutic catheter tip:
- Easy control capability and a clear direction and location of the ultrasonic ray and/or catheter location to carry out treatment, such as according to the ultrasonic echo reflection analysis.
- Ability to control the circumferential direction of the artery tissue damage.
- Continues information (e.g., ultrasonic measurement) on the position of the catheter tip, such as from the artery wall during treatment.
- Automatic detection of unwanted and/or risky movement of the catheter during treatment.

Alternative Ways to Determine Desirable Parameters

In some embodiments of the invention, trial and error is used to figure out at least some parameters. For example, an initial set of parameters estimated to cause a relatively small area of damage can be applied to the target tissue. Alternatively, damage is applied to a region that would not be affected by the small area of damage. Based on the resulting area and/or volume of damage caused by the parameter settings (e.g., according to imaging), one or more settings can be adjusted to achieve a desired effect in the target tissues. Such a process can be followed iteratively until the desired effect is achieved. Such a process is potentially useful in certain situations, for example, if the rate of blood flow is unclear.

In some embodiments of the invention, one or more equations (e.g., a simplified physical and/or mathematical model) are developed for obtaining at least some parameters, for example, as described in detail in the sections "EXEMPLARY DEVELOPMENT OF AN EQUATION" parts A and/or B. In some embodiments, the equations are used to derive parameters according to experimental results. In some embodiments, different equations are developed for different experiments, such as for targeting different types of tissues in different anatomical areas. In some embodiments, parameters are extrapolated based on experimental results.

Exemplary Development of an Equation—Part A

Inventors followed the process as described in FIGS. 1A and/or 1B to conduct experiments in 10 pigs (e.g., results displayed with reference to FIG. 12A). Experiments were performed using a catheter having a diameter of 3 mm. The data collected from the process was analyzed and turned into parameters that affect treatment; the intensity of ultrasound energy, the frequency of ultrasound energy, and the flow rate of blood in the artery. An equation was developed associating the parameters with the resulting area of damaged tissue, such as the minimum radial distance from the artery wall.

The equation is based on the results of the conducted experiments that showed the effect initiating about 3 mm from the intima, in the most distant location of the peri-adventitia. As the acoustic intensity profile increased, the effect increased towards the intima. The experiments were conducted for a period of about 30 seconds. The equation can be adapted for other time periods in a similar manner.

The function that associates the radial distance (the distance from the arterial wall to the start of the damaged area) to the ultrasound treatment parameters is:

$$x(f,I)[mm]=(C6+a*\mathrm{Exp}(\mathrm{flow}*b)-C2*\log(C3*I[W/cm^2]))/(C4*f[MHz]+C5)$$

Where:
I=Excitation intensity [w/cm^2]
f=Working excitation frequency [MHz]

x=Minimal radial distance from the artery wall [mm]
flow=blood flow rate in the artery [ml/min]

Calculated coefficients in order to adjust the model assumptions, neglects and unknown variables to the experimental results:

a=3.7 (2 . . . 4)
b=−1134(−2500 . . . 0)
C2=93 (90 . . . 100)
C3=2.2 (1 . . . 4)
C4=2.1 (1 . . . 4)
C5=47.4 (45 . . . 50)
C6=400 (0 . . . 1000)

*the numbers in ( . . . ) are the limits of the parameters estimation based on the results of the experiments conducted.

The physical model (for parts A and/or B, below) is based on several assumptions and/or simplifications. The Arrhenius thermal damage equation was used as the basis for estimating the thermal damage area in the artery wall, using a time value of 30 seconds and an effective temperature higher than 55 degrees Celsius. The blood flow in the artery was assumed to be exponentially related to cooling of the artery wall by convection.

The equations were developed by plotting the experimental results (e.g., as summarized in FIG. 12A for the renal arteries (shown in FIG. 13A) and for the carotid arteries (shown in FIG. 13B). The plots graphically illustrate the extent of thermal damage (e.g., the distance from the intima to the start of the damage on the 'y-axis) as a function of the intensity of the applied acoustic energy (on the 'x-axis) and as a function of the frequency of the applied acoustic energy (on the 'z-axis'). The coefficients of the equation were adjusted in order to align the equation to the plots.

Exemplary Development of an Equation—Part B

In another set of experiments, inventors followed the process as described in FIGS. 1A and/or 1B to conduct experiments in 12 pigs (e.g., results shown in FIGS. 12B-12D). Experiments were performed using a catheter having a diameter of 2 mm, at frequencies of 10 Mhz and/or 20 Mhz. Ultrasound was emitted at intensities ranging from 10-35 watt/cm$^2$, for time periods ranging from 10-30 seconds. The anatomical target sites were the left and/or right renal arteries.

FIG. 12B summarizes the experimental data for an ultrasound emission frequency of 10 Mhz. FIG. 12C summarizes the experimental data at 20 Mhz. FIG. 12D shows graphs visually displaying the data of FIGS. 12B-12C.

FIG. 12E illustrates variables describing the resulting area of damaged tissue, useful in helping to understand the results shown in FIGS. 12B-12D. The left side of the figure illustrates a cross section of an artery (all measurements in millimeters). 'MED' represents the thickness of the media layer of the arterial wall. 'L' represents the minimum distance of the affected region from the lumen wall. 'W' represents the maximal width of the effected region. 'Th' represents the thickness of the affected region. 'S' represents the severity of the affected region (e.g., as defined by a trained professional), defined as: 0=no thermal damage, 0.5=thermal damage to nerves only, 1=thermal damage to connective tissue in surrounding artery, 2=thermal damage to media (represents possible future risk of arterial stenosis).

Equations associating the parameters of ultrasound energy (frequency and intensity) to the thermal effect in tissue were developed by fitting the thermal damage parameters based on the histological analysis. Exemplary graphs are shown in FIGS. 13C-13H. Exemplary fitting coefficients (e.g., for duration of 30 seconds) are shown in the table below. Although coefficients correspond to a duration of 30 seconds, this is not intended to be limiting, and a similar analysis can be conducted for any other data points. It is emphasized that the coefficients in the table cannot be compared with each other. Each coefficient is distinct with reference to each formula. For example, the coefficient '$b_1$' in formula 2 is different than the coefficient '$b_1$' in formulas 3-7.

One possible function that associates the radial distance 'L' to the ultrasound treatment parameters of intensity (watt/cm$^2$) and frequency (Mhz) is shown as:

$$L(I, f) = \frac{c_1 - c_2 \log(c_3 I)}{c_4 f + c_5} \quad \text{equation (1)}$$

Equation 1 contains 5 unknowns, but can be simplified to only 3 independent values, such as shown in equation 2. Some relationships represented by equation 2 are graphically illustrated by FIG. 13C.

$$L(I, f) = \frac{b_1 - \log(I)}{b_2 f + b_3}. \quad \text{equation (2)}$$

The relatively stronger flow of blood related to the relatively smaller diameter catheter in this group of experiments (2 mm vs 3 mm) is taken into consideration automatically by the proper choice of the first parameter in equation (2).

One possible function that associates the width 'W' to intensity and frequency is represented by equation 3. Some relationships represented by equation 3 are graphically illustrated by FIG. 13D.

$$W(I,f) = (b_1 + b_2 f)I + (b_3 + b_4 f)I^2 \quad \text{equation (3)}$$

One possible function that associates the severity of the thermal effect 'S' to intensity and frequency is represented by equation 4. Some relationships represented by equation 4 are graphically illustrated by FIG. 13E.

$$S(I,f) = (b_1 + b_2 f)I + (b_3 + b_4 f)I^2 \quad \text{equation (4)}$$

Some possible functions that associate the standard deviations of 'L', 'W' and 'S' to intensity and frequency include respective equations 5-7. Some relationships represented by equations 5-7 are graphically illustrated by respective FIGS. 13F-H.

$$\sigma_L(I, f) = \frac{b_1 + b_2 I}{b_3 f + b_4}. \quad \text{equation (5)}$$

$$\sigma_W(I, f) = \frac{b_1 + b_2 I}{b_3 f + b_4}. \quad \text{equation (6)}$$

$$\sigma_S(I, f) = \frac{b_1 + b_2 I^2}{b_3 f + b_4}. \quad \text{equation (7)}$$

Table of exemplary coefficients corresponding to exemplary equations 2-7.

| Parameter | Formula | $b_1$ | $b_2$ | $b_3$ | $b_4$ |
|---|---|---|---|---|---|
| L | (2) | 6.22 | 0.080 | 0.665 | — |
| W | (3) | 0.1374 | −0.0044 | −0.0065 | 0.00056 |

-continued

Table of exemplary coefficients corresponding to exemplary equations 2-7.

| Parameter | Formula | $b_1$ | $b_2$ | $b_3$ | $b_4$ |
|---|---|---|---|---|---|
| S | (4) | −0.0082 | 0.0039 | 0.00014 | $-1.9 \cdot 10^{-5}$ |
| $\sigma_L$ | (5) | −0.069 | 0.012 | −0.016 | 0.40 |
| $\sigma_W$ | (6) | −1.87 | 0.45 | −0.29 | 10.13 |
| $\sigma_S$ | (7) | 1.66 | 0.0070 | −0.53 | 18.18 |

The equations (parts A and B) illustrate that the frequency can be adjusted to control the area of damage. For example, a relative increase in frequency can result in one or more of: the treatment region being relatively closer to the wall edge, the width of the treatment region being relatively increased, the severity of the damage being relatively increased. The relative decrease in frequency can result in one or more of: the treatment region being relatively further to the wall, the width is relatively reduced, the severity of the damage is relatively reduced.

The equations further illustrate that the intensity can be adjusted to control the area of treatment region. For example, a relatively increase in intensity can result in one or more of: the treatment region being relatively further closer to the wall edge, the width of the treatment region being relatively increased, the severity of the damage being relatively increased. The relative decrease in intensity can result in one or more of: the treatment region being relatively further from the wall, the width is relatively reduced, the severity of the damage is relatively reduced.

As can be seen, various application times can be used as well.

In an exemplary embodiment of the invention equations can be used to calibrate the system. For example, the system can use the equations to provide an initial set of parameters. Optionally, treatment is synchronized to adjustments. For example, a thermal effect can be applied to a test region, or a small part of the target region. Feedback such as imaging can be performed to estimate the distance from the treated region to the arterial wall, the width of the region and/or the severity of the thermal effect (e.g., as described in co-filed PCT application PCT/IB2011/054639). The actual measured values can be compared to the expected values. One or more parameters such as frequency and/or intensity can be adjusted relatively higher or relatively lower. The process can be repeated in a feedback-loop, thereby achieving the desired thermal effect to the desired area of tissue at the desired location.

Experimental Results

FIG. 12A is a table summarizing experimental results of selective thermal effects (e.g., damage) to arterial wall tissues, performed by the inventors, in accordance with some embodiments of the invention.

Experiments were performed in a total of 10 pigs, with multiple locations treated in the carotid and renal arteries. The pigs were under general anesthesia. The frequencies of ultrasound used were 10 Mhz, 15 Mhz and 20 Mhz. The intensity of acoustic ultrasound applied to the target tissue ranged from 1-10 watts/square centimeter to over 71 watts/square centimeter. The treatment duration was 30 seconds per location. The ultrasonic catheter used had a transducer with dimensions of 1.5 mm×6 mm×0.8 mm. The size of the catheter was 9 French. The length of the catheter was 55 cm when inserted into the renal artery, and a catheter having a length of 95 cm was used for the carotid artery.

In the set of experiments performed, the acoustic intensity was applied for about 30 seconds.

In the set of experiments performed, the thermal damaged initiated in the peri-adventitia, increasing towards the intima. The tables illustrate that the area of damage from the peri-adventitia inwards, for example, PA=damage localized to the peri-adventitia, M=damage from the peri-adventitia to the media, IEM=damage from the peri-adventitia to the internal elastic media. The area damaged (e.g., on a cross sectional histological slide through the artery) was summarized as S=small, M=medium and L=large. The definition of the damage (S,M,L), reflects the percentage of tissue with damage in the relative sector with the pathology; S=1-20% damage, M=21-60% damage, L=>61% of damage. The damage was localized by sectors in a clockwise manner. The percentage effect represents the proportion of the damage inside the defined sector. For example, "S" represents a string-like damage zone, while "L" represents that most or all of the sector area was affected.

In the experiments performed, nerves in the peri-adventitia were damaged, for example, Y=damaged nerve, N=no damaged nerves. The extent of damage and/or the identification of damaged nerves was conducted by a trained pathologist. In the experiments performed, the location of damage in the arterial wall was selective. "Points" refers to the location (e.g., center of a treatment region) in the arterial wall by using an arbitrary clock as measurement, for example, 12 o'clock=0 degrees, 6 o'clock=180 degrees. The transducer was directed towards the affected sector.

In the experiments performed, multiple lesions were selectively made in a single blood vessel in a pig.

Experiment in the Aorta #1

Study subject: a female domestic pig, 71.7 Kg had been treated with an ultrasonic treatment system on its renal left artery.
Anatomical target: nerves in the surrounding of the ostium of the right renal artery.
Anatomical position of catheter: aorta artery, proximity to the ostium of right renal artery.
Length of ultrasonic treatment catheter: 55 cm
Transducer frequency: 20 MHz
Time component of intensity profile: 30 seconds
Acoustic intensity component of intensity profile: 52 Watts/cm^2
Results: mild thermal effect was demonstrated at the peri adventitia.

FIG. 14A represents a 2× magnification of the location at the aorta artery circumference that was treated with the ultrasonic system, 6.0 mm proximal from the renal right ostium artery. The marked area represents the border of the thermal effect seen in the priadventitia, which manifests in an irreversible tissue, and vessels necrosis, (T=Thermal).

FIG. 14B represents a 4× magnification of the thermal area.

Schematic Description of Pathology Analysis:

FIG. 14C represents a top view of all the artery layers (see index box as follows), at the relevant depth (6.0 mm from the renal right ostium). The artery is planned clockwise for the pathology definition.

The thermal effect seen in the artery is represented by the black area in the peri-adventitia, at sector 9.

Experiment in the Aorta #2

Study subject: a female domestic pig, 71.7 Kg had been treated with an ultrasonic treatment system on its renal left artery.

Anatomical target: nerves in the surrounding of the ostium of the right renal artery.
Anatomical position of catheter: aorta artery, proximity to the ostium of right renal artery.
Length of ultrasonic treatment catheter: 55 cm
Transducer frequency: 20 MHz
Time component of intensity profile: 30 seconds
Acoustic intensity component of intensity profile: 67 Watts/cm^2
Results: nerves at the ostium of the aorta were treated.

Figure 15A:
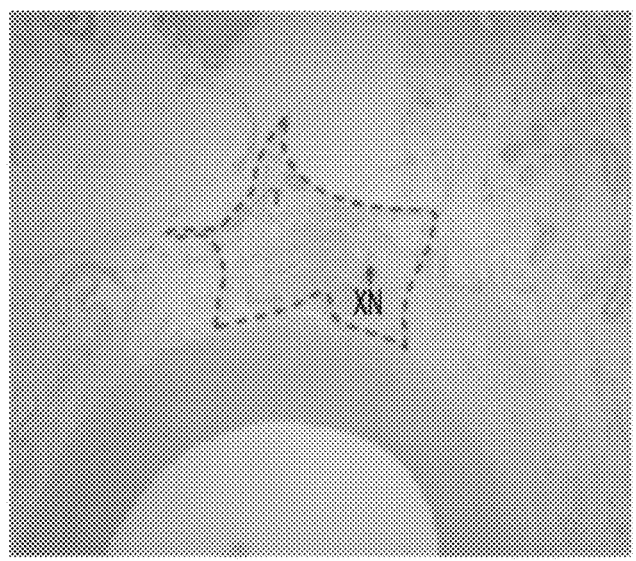

FIG. 15A represents a 2× magnification of the location at the aorta artery circumference that was treated with the ultrasonic system, 6.5 mm proximal from the renal right ostium artery. The marked area represents the border of the thermal effect seen in the priadventitia, which manifests in an irreversible tissue, and vessels necrosis, (T=Thermal). Furthermore the nerve which was affected by the ultrasonic treatment is marked with XN, which represents unviable nerves, expressed by necrosis of the nerve.

Figure 15B:
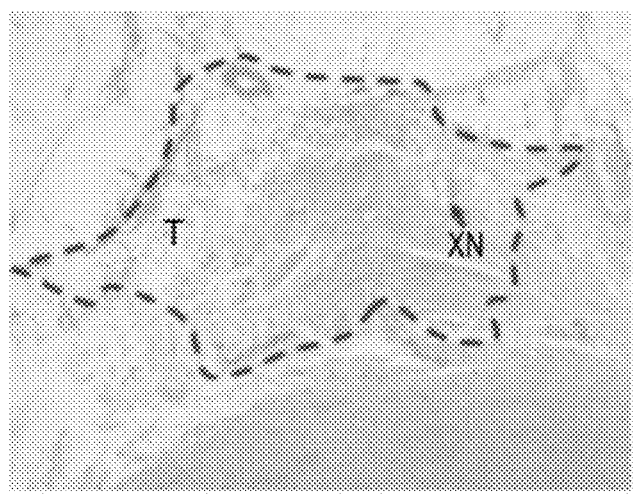

FIG. 15B represents a 4× magnification of the thermal area and the localization of the thermal necrotic nerve.

Figure 15C:
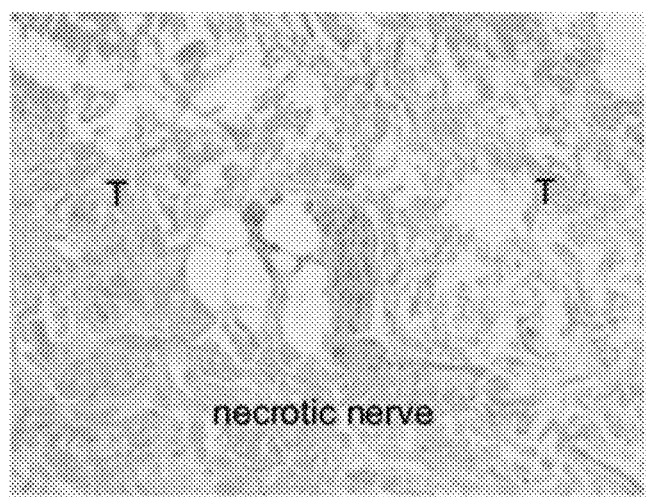
Figure 15D:
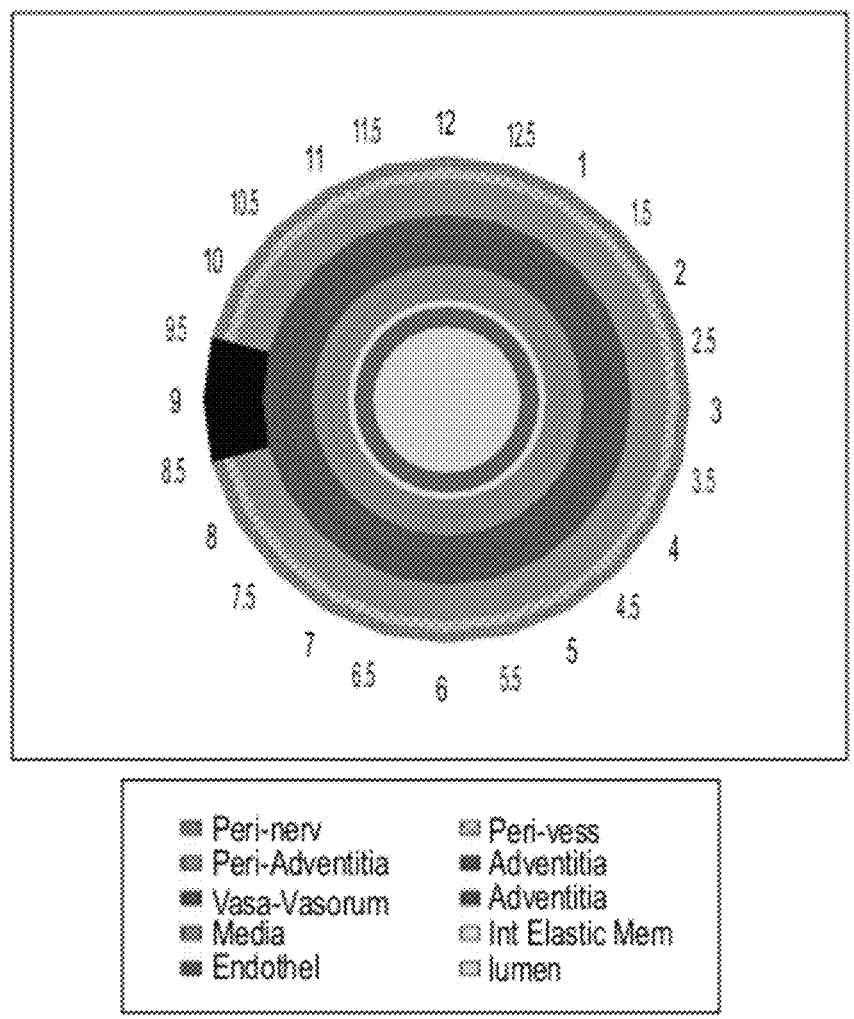

FIG. 15C represents a 10× magnification of the necrotic nerve surrounded by tissue with thermal effect.

Schematic Description of Pathology Analysis:

FIG. 15 D represents top view of all the artery layers (see index box as follows), at the relevant depth (6.5 mm from the renal right ostium). The artery is planned clockwise for the pathology definition.

The thermal effect seen in the artery is represented by the black area in the peri-adventitia, at sector 9.

Experiment in the Carotid Artery #1

Study subject: a female domestic pig, 72.8 Kg had been treated with an ultrasonic treatment system on its carotid left artery.
Anatomical target: nerves in the wall of the right common carotid artery.
Anatomical position of catheter: Right common carotid artery.
Length of ultrasonic treatment catheter: 95 cm
Transducer frequency: 20 MHz
Time component of intensity profile: 30 seconds
Acoustic intensity component of intensity profile: 34 Watts/cm^2
Results: thermal effect was demonstrated from the media layer throughout the priadventitia of the right common carotid artery.

FIG. 16A represents a 2× magnification of the location of the thermal effect at the circumference of the right common carotid artery. The marked area represents the border of the thermal effect seen in the media throughout the priadventitia layer, which manifests in pyknosis of the smooth muscle cells and focal collagen condensation.

FIG. 16B represents a 4× magnification of the thermal area

Schematic Description of Pathology Analysis:

FIG. 16C represents top view of all the artery layers (see index box as follows), at the relevant depth. The artery is planned clockwise for the pathology definition. The thermal effect seen in the artery is represented by the black area in the peri-adventitia, at sector 1-3.

Experiment in the Carotid Artery #2

Study subject: a female domestic pig, 78.0 Kg had been treated with an ultrasonic treatment system on its carotid left artery.

Anatomical target: nerves in the wall of the left common carotid artery.
Anatomical position of catheter: left common carotid artery.
Length of ultrasonic treatment catheter: 95 cm
Transducer frequency: 20 MHz
Time component of intensity profile: 30 seconds
Acoustic intensity component of intensity profile: 13.2 Watts/cm^2
Results: nerves surrounding the left common carotid artery were treated FIG. 17A represents a digital scan of the 28.5 mm from the aorta arch slide. The thermal effect is manifested in an irreversible tissue, and vessels necrosis in less than 25% of the peri adventitia in the artery circumference. Furthermore nerves which were affected by the ultrasonic treatment are found to be necrotic.

Schematic Description of Pathology Analysis:

FIG. 17B represents top view of all the artery layers (see index box as follows), at the relevant depth (6.5 mm depth from the aorta). The artery is planned clockwise for the pathology definition.

The thermal effect seen in the artery is represented by the black area in the peri-adventitia, at sector 3.

Experiment in the Renal Artery #1

Figure 18A:
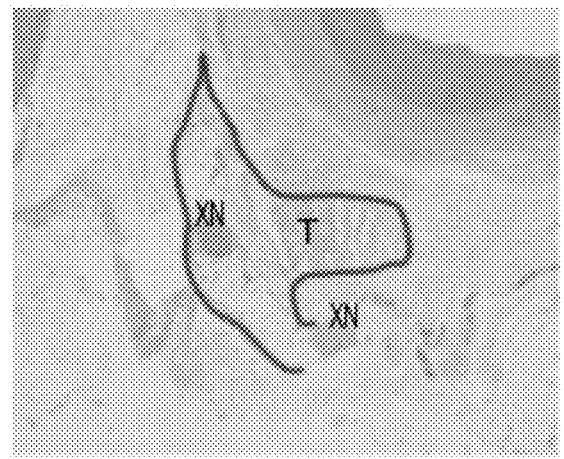

Study subject: a female domestic pig, 68.2 Kg had been treated with an ultrasonic treatment system on its renal left artery.
Anatomical target: nerves in the wall of the left renal artery.
Anatomical position of catheter: left renal artery.
Length of ultrasonic treatment catheter: 55 cm
Transducer frequency: 10 Mhz
Time component of intensity profile: 30 seconds
Acoustic intensity component of intensity profile: 26 Watts/cm^2
Results: nerves surrounding the left renal artery were treated FIG. 18A represents a 2× magnification of the 6.5 mm depth from the aorta slide. The marked area represents the border of the thermal effect seen in the priadventitia, which manifests in an irreversible tissue, and vessels necrosis, (T=Thermal). Furthermore the nerves which were affected by the ultrasonic treatment are marked with XN, which represents unviable nerves. Both nerves in the surrounding of thermal area are necrotic.

Figure 18B:
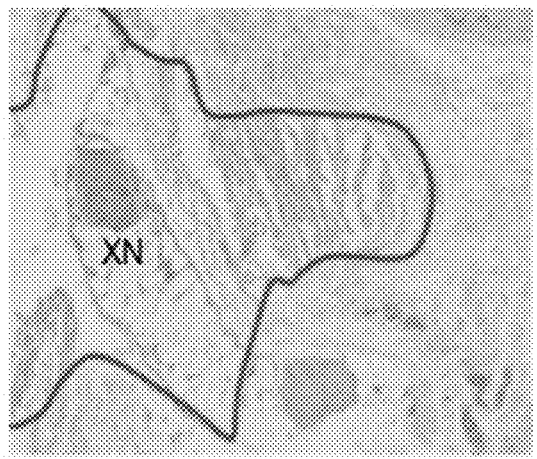

FIG. 18B represents a 4× magnification of the thermal area, and the localization of the thermal necrotic nerves.

Figure 18C:
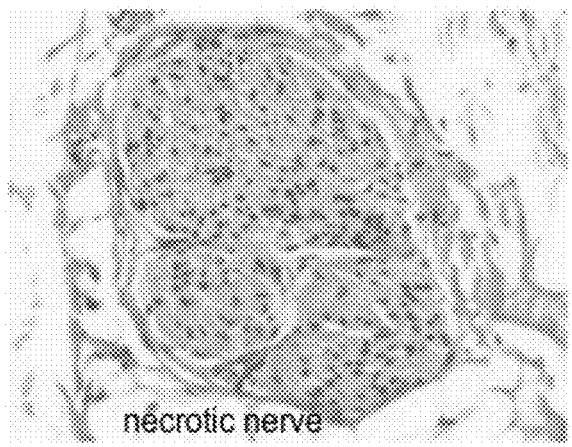

FIG. 18C represents a 10× magnification of the necrotic nerves inside the thermal effect zone.

Figure 18D:
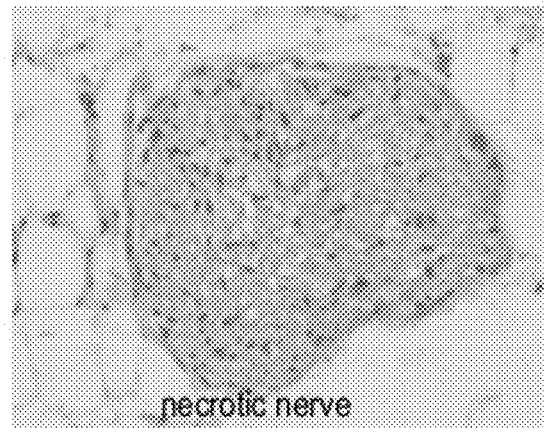

FIG. 18D represents a 10× magnification of the necrotic nerve outside the thermal effect zone. Both nerves' necrosis caused by the thermal ultrasonic treatment.

Figure 18E:
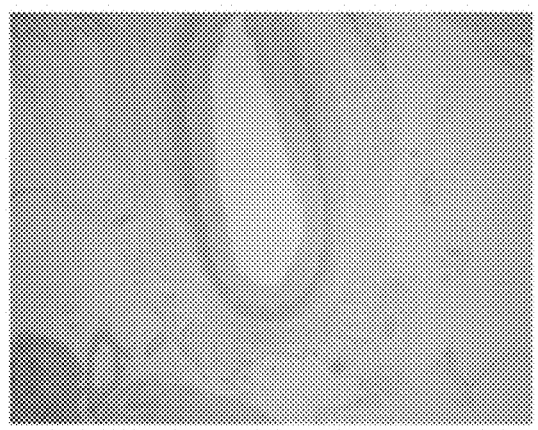
Figure 18F:
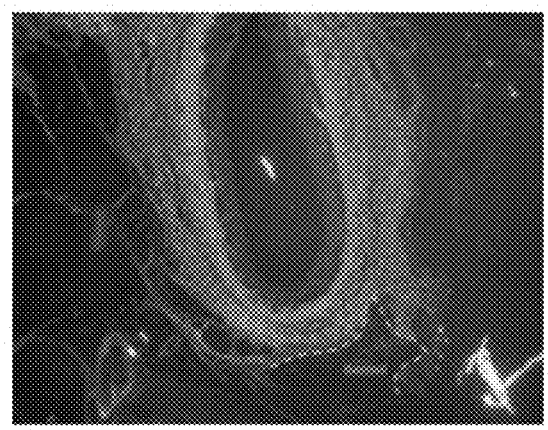

FIG. 18E represents a 2× magnification of the 6.5 mm depth from the aorta slide stained in PSR, before applying the polarizer lens.

Figure 18G:
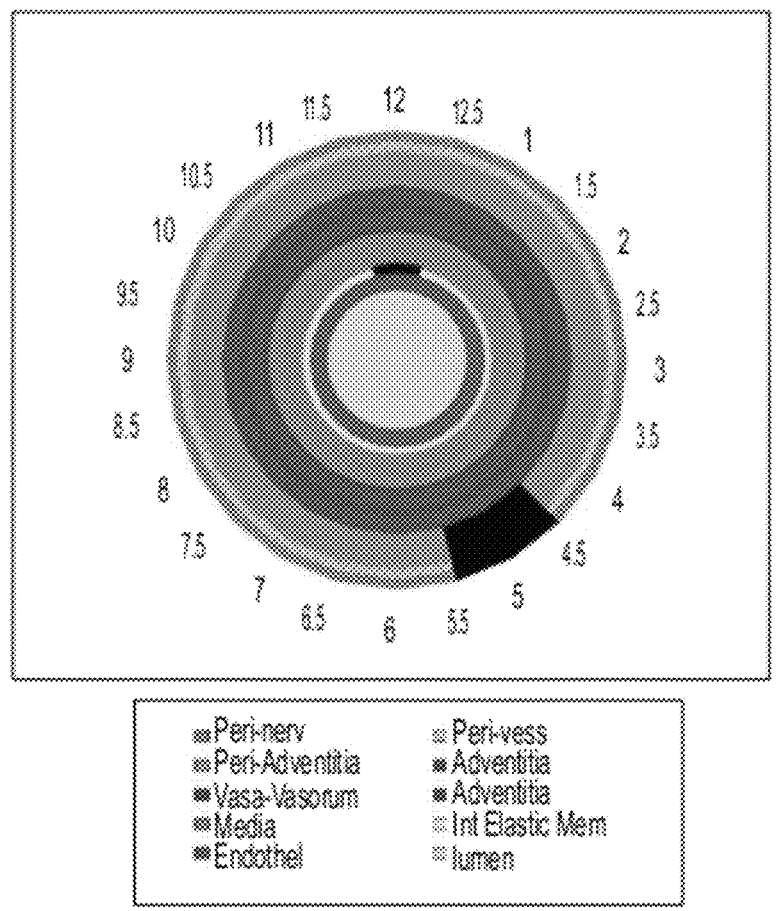

FIG. 18G represent a 2× magnification of the 6.5 mm depth from the aorta slide, examined under polarizer light, representing a distinctive negative birefringence caused by collagen denaturation as consequence of the ultrasonic treatment. The marked area represents the border of the thermal effect seen in the priadventitia.

Schematic Description of Pathology Analysis:

FIG. 18G represents top view of all the artery layers (see index box as follows), at the relevant depth (6.5 mm depth from the aorta). The artery is planned clockwise for the pathology definition.

The thermal effect seen in the artery is represented by the black area in the peri-adventitia, at sector 5.

Pathology Analysis: Pathology Report Prepared by a Trained Pathologist

The table below represents the pathology report for the experiment. The table contains columns with the artery layers, different potential pathologies relevant to the artery layer, slide ID with a categorical scoring of lesions (as detailed below), and a sector (S) column for the localization of the pathology damage in clockwise manner.

| Slide ID: PIG No. | N05-R-L3 | N05-R-L3 + 0.5 | Sector | Status |
|---|---|---|---|---|
| Lumen | Free thrombus | 0 | | |
| Endothelium | Pyknosis | 0 | | |
| Endothelium | Attached thrombus | 0 | | |
| Endothelium | Fibrin deposition | 0 | | |
| Endothelium | Erosion | 4 | 1-12 | |
| Int. Elastic Lamina | Distorted | 0 | | |
| Int. Elastic Lamina | Rupture | 1 | 11-1 | |
| Media | Inflammation | 0 | | |
| Media | Pyknosis* | 1 | 11-1 | |
| Media | Necrosis | 0 | | |
| Media | Damage width (%) | 40- | 11-1 | |
| Vasa-Vasorum | Thrombus | 0 | | |
| Vasa-Vasorum | Fibrin | 0 | | |
| Vasa-Vasorum | Necrosis | 0 | | |
| Adventitia | Pyknosis | 0 | | |
| Adventitia | Necrosis | 0 | | |
| Adventitia | Inflammation | 0 | | |
| P. Adventitia vessels | Necrosis | 1 | 5 | THERMAL |
| P. Adventitia vessels | Thrombus | 0 | | |
| Peri Adventitia | Inflammation | 0 | | |
| Peri Adventitia | Necrosis | 1 | 5 | |
| P. Adventitia nerves | Degeneration/ vacuolation | 0 | | |
| P. Adventitia nerves | Inflammation | 0 | | |
| P. Adventitia nerves | Necrosis | 1 | 5 | |

For lesion scoring:

Media damage width (%, maximum width given):

0: Normal
1: Minimal or involving 0-25% of the vessel circumference
2: Mild or involving 25-50% of the vessel circumference
3: Moderate or involving 50-75% of the vessel circumference
4: Marked/Severe or involving 75-100% of the vessel circumference X−: damage from the lumen towards the periphery of the vessel
X+: damage from the periphery towards the lumen of the vessel
A: Artifact on histological processing
S-Clockwise sector Experiment in the Renal Artery #2

Study subject: a female domestic pig, 65.7 Kg had been treated with an ultrasonic treatment system on its renal left artery.
Anatomical target: nerves in the wall of the right renal artery.
Anatomical position of catheter: right renal artery.
Length of ultrasonic treatment catheter: 55 cm
Transducer frequency: 20 Mhz
Time component of intensity profile: three times for a period of 30 second each
Acoustic intensity component of intensity profile: 53 Watts/cm^2, 59 Watts/cm^2 and 66 Watts/cm^2 respectively.
Results: thermal effect was demonstrated at the peri adventitia of the right renal artery.

FIG. 19A represent a 2× magnification of the 6.5 mm depth from the aorta slide. The marked area represents the border of the thermal effect seen in the priadventitia, which manifests in an irreversible tissue necrosis, (T=Thermal).

FIG. 19B represents a 4× magnification of the thermal area. No nerves were affected at this treatment.

Schematic Description of Pathology Analysis:

FIG. 19C represents top view of all the artery layers (see index box as follows), at the relevant depth (6.5 mm depth from the aorta). The artery is planned clockwise for the pathology definition.

The thermal effect seen in the artery is represented by the black area in the peri-adventitia, at sector 6-7.

Pathology Analysis: Pathology Report Prepared by a Trained Pathologist

The table below represents the pathology report for the experiment. The table contains columns with the artery layers, different potential pathologies relevant to the artery layer, slide ID with a categorical scoring of lesions (as detailed below), and a sector (S) column for the localization of the pathology damage in clockwise manner.

| Slide ID: PIG No. | N06-R-R4 | N06-R-R4 + 0.5 | Sector |
|---|---|---|---|
| Lumen | Free thrombus | 0 | |
| Endothelium | Pyknosis | 0 | |
| Endothelium | Attached thrombus | 0 | |
| Endothelium | Fibrin deposition | 1 | 12 |
| Endothelium | Erosion | 2 | 9-3 |
| Int. Elastic Lamina | Distorted | 0 | |
| Int. Elastic Lamina | Ruptured | 1 | 12 |
| Media | Inflammation | 0 | |
| Media | Pyknosis* | 1 | 12 |
| Media | Necrosis | 0 | |
| Media | Damage width (%) | <10- | 12 |
| Vasa-Vasorum | Thrombus | 0 | |
| Vasa-Vasorum | Fibrin | 0 | |
| Vasa-Vasorum | Necrosis | 0 | |
| Adventitia | Pyknosis | 0 | |
| Adventitia | Necrosis | 0 | |
| Adventitia | Inflammation | 0 | |
| P. Adventitia vessels | Necrosis | 0 | |
| P. Adventitia vessels | Thrombus | 0 | |
| Peri Adventitia | Inflammation | 0 | |
| Peri Adventitia | Necrosis | 1 | 6-7 |
| P. Adventitia nerves | Degeneration/ vacuolation | 0 | |
| P. Adventitia nerves | Inflammation | 0 | |
| P. Adventitia nerves | Necrosis | 0 | |

For lesion scoring:

Media damage width (%, maximum width given):

0: Normal
1: Minimal or involving 0-25% of the vessel circumference
2: Mild or involving 25-50% of the vessel circumference
3: Moderate or involving 50-75% of the vessel circumference
4: Marked/Severe or involving 75-100% of the vessel circumference X−: damage from the lumen towards the periphery of the vessel
X+: damage from the periphery towards the lumen of the vessel
A: Artifact on histological processing

Experiment in the Renal Artery #3

Figure 20A:
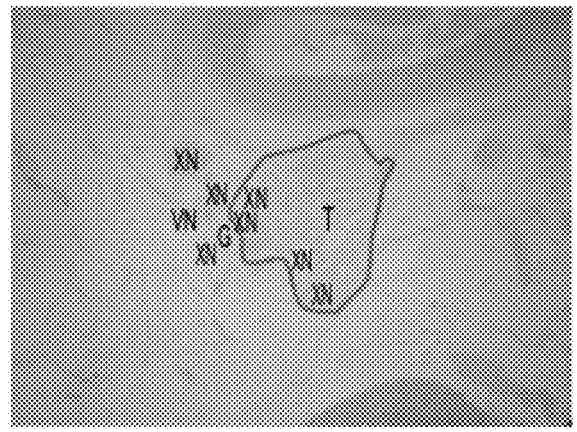

Study subject: a female domestic pig, 65.7 Kg had been treated with an ultrasonic treatment system on its renal left artery.
Anatomical target: nerves in the wall of the right renal artery.
Anatomical position of catheter: right renal artery.
Length of ultrasonic treatment catheter: 55 cm
Transducer frequency: 20 MHz
Time component of intensity profile: twice for a period of 30 second each
Acoustic intensity component of intensity profile: 40 Watts/cm^2 and 53 Watts/cm^2
Results: nerves surrounding the right renal artery were treated FIG. 20A represents a 2× magnification of the 10.5 mm depth from the aorta slide. The marked area represents the border of the thermal effect seen in the priadventitia, which manifests in an irreversible tissue, and vessels necrosis, (T=Thermal). Furthermore the nerves which were affected by the ultrasonic treatment are marked with XN, which represents unviable nerves, and VN, which represent viable nerves. In the surrounding of thermal area are present 8 nerves, including 7 unviable.

Figure 20B:
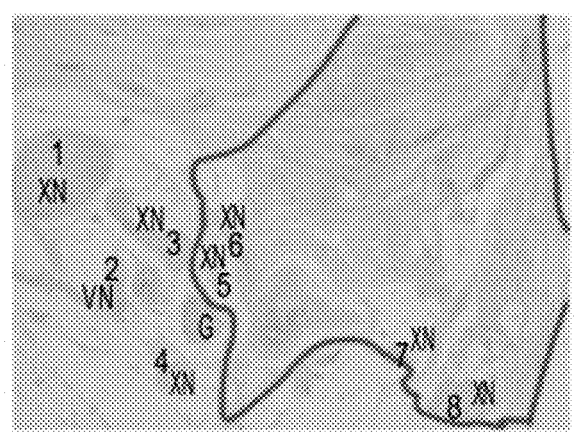

FIG. 20B represents a 4× magnification of the thermal area.

Figure 20C:
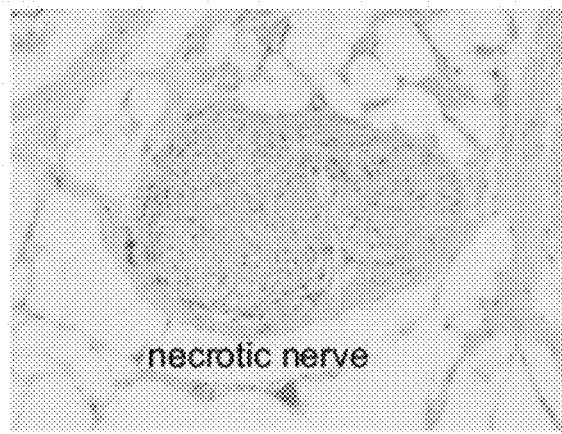
Figure 20D:
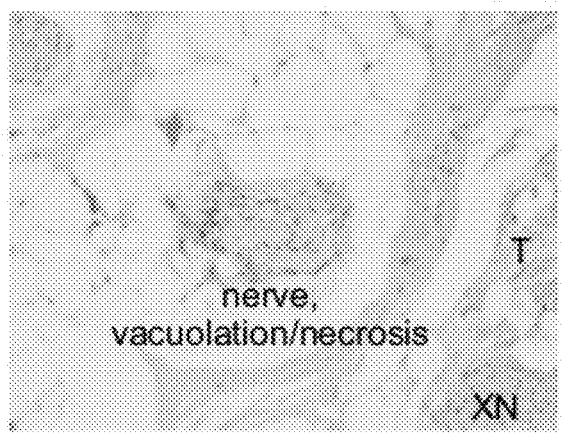
Figure 20E:
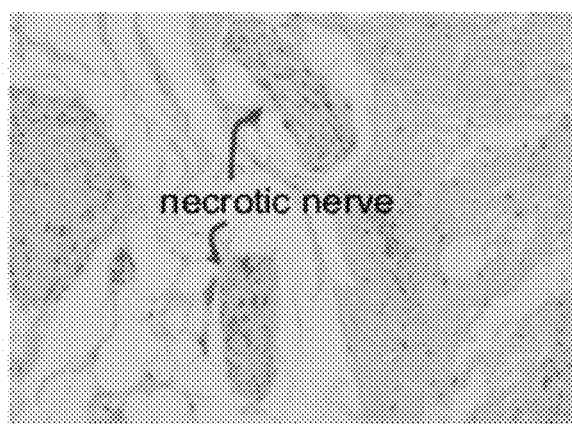
Figure 20F:
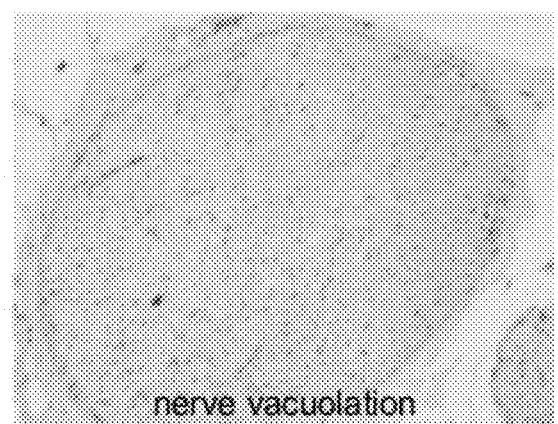
Figure 20G:
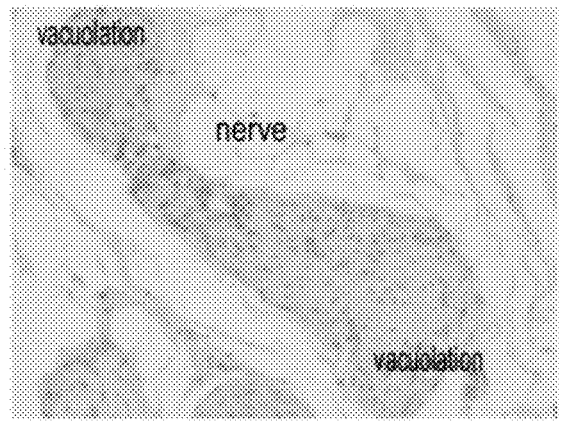
Figure 20H:
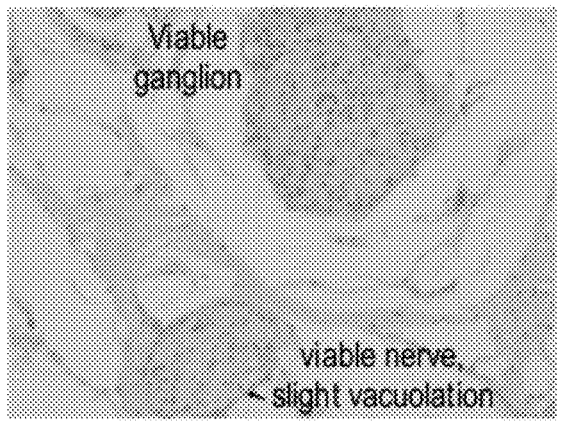
Figure 20I:
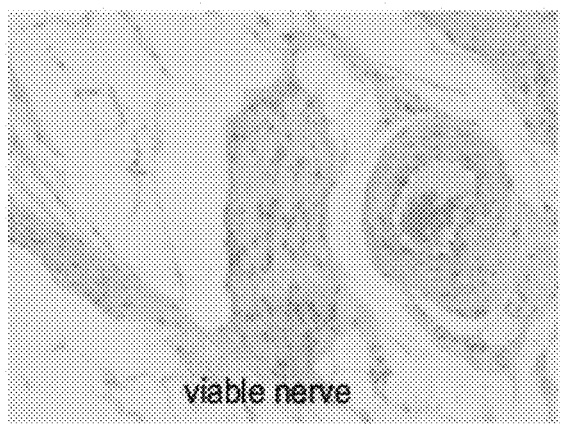

FIGS. 20C-E represents a 10× magnification of the necrotic and/or vacuolated nerves inside the thermal effect zone.

FIGS. 20F-I represents a 10× magnification of the necrotic and/or vacuolated and viable nerves outside the thermal effect zone.

Figure 20J:
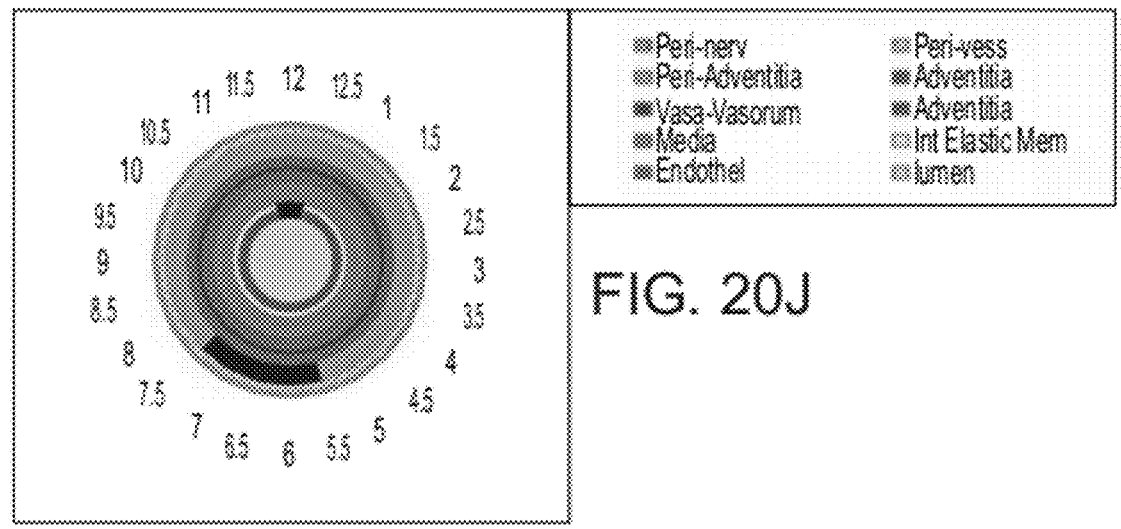

Schematic Description of Pathology Analysis:

FIG. 20J represents top view of all the artery layers (see index box as follows), at the relevant depth (10.5 mm depth from the aorta). The artery is planned clockwise for the pathology definition.

The thermal effect seen in the artery is represented by the black area in the peri-adventitia, at sector 4-5.

Renal Denervation Study #1

Goal: Inventors performed a controlled study to evaluate the clinical feasibility and/or safety of performing a renal denervation procedure in a chronic swine model, in accordance with some embodiments of the invention.
Study End Points
  Primary: A significant decrease in norepinephrine levels at 30 days following the procedure, in the treatment group compared to the control group.
  Secondary: Lack of procedure related stenosis in the treated renal arteries at 30 days following the procedure.

Experimental Materials

Equipment: An ultrasound emission element, catheter and control system as described herein and/or in the related applications was used to perform the treatments. A 10 Mhz ultrasound emission element was used in the first set of experiments. A 20 Mhz element was used in the second set of experiments.
Animals and preparation: All aspects of the study were approved by the Animal Research Committee. A total of 10 Yorkshire domestic swine (weight 70-75 Kg) were used for the first set of experiments, 4 underwent the renal denervation procedure and 6 served as control. 5 additional pigs were used for the second set of experiments, all underwent the procedure.
Animal preparation: Anatomic eligibility was confirmed by angiography prior to the treatment. No animals were disqualified. The experiment was performed under general anesthesia. Intravenous heparin was administered to achieve an intraprocedural activated clotting time (ACT)>250 seconds. At the end of the procedure the animals were euthanized.

Experimental Protocol

Ultrasonic Treatment:

In the experimental swine group, the catheter was advanced via a femoral approach to access the renal arteries. Ultrasound treatment, in accordance with some embodiments of the invention, was administered at the main arterial trunks in one or more locations. In each location, the ultrasound energy was directed in up to 4 angles of the arterial circumference (e.g., 0°, 90°, 180°, 270°—equivalent to 12, 3, 6, 9 hours in a clock model). Ablation of neural tissue was performed by ultrasonic excitation of 10 or 30 seconds in each treatment location. In actual practice, a smaller or larger number of angle may be used.

The catheter distance from the artery wall was measured using ultrasonic imaging of the system, prior to ultrasonic excitation, in accordance with some embodiments of the invention. If needed, a distancing device (e.g., as described with reference to co-filed PCT application "Separation device for ultrasound transducer", PCT/IB2011/054638) was deployed, such as a part of the safety mechanism.

Control: No ultrasonic energy was applied to the 6 swines in the control group. One control animal was cannulated and the catheter was introduced to the renal arteries without ultrasonic energy delivery.

Angiography: Angiography was performed during three time periods; prior to the procedure, immediately at the end of procedure, and at 30 days+2 days. Under angiography, each renal artery was examined by a trained physician for stenosis, constriction and/or any abnormalities in blood flow.

Biopsy: All experimental and control animals were biopsied. In vivo, open bilateral renal cortex biopsies were conducted in order to perform a norepinephrine (NE) quantitative analysis. The biopsy was taken from the cranial and caudal poles of the kidney under direct vision. Samples were sent to analysis of NE levels in the tissue using HPLC.

Histology: The renal arteries and kidneys were perfused, dissected and immersed in 4% formalin prior to histological processing. Pathological examination for any thermal or mechanical damage to the renal arteries and connective tissue, including nerves.
Procedure Parameters Procedure parameters are described for the first set of experiments.

An average of about 6.5+0.5 ultrasonic treatments were performed in the right renal artery in two locations along the artery, and about 4.5+1.0 ultrasonic treatments were performed in the left artery, in 1-2 focal locations along the artery. In an exemplary embodiment of the invention, a number of treatments can be performed in a number of locations. For example, 1, 2, 4, 8 or other smaller, intermediate or larger treatment locations are available. For example, 1, 2, 4, 6, 8, 12 or other smaller, intermediate or larger numbers of treatments can be performed in an artery.

Ultrasonic ablations were applied in one of two time durations, 10 seconds or 30 seconds. In an exemplary embodiment of the invention, the treatment time is about 1 second, about 5, 10, 15, 20, 25, 30, 35, 50, 60, 100 seconds or other smaller, intermediate or larger time periods are used.

The average total procedure time was about 35.2+13.3 minutes. The maximal temperature measured by the sensor close to the ultrasonic transducer was about 44.25+1.0 degrees Celsius in the right renal artery, and about 45.2+3.4 degrees Celsius in the left renal artery. The temperatures are considered safe.

Table summarizing the treatment parameters

| Animal ID | Number of excitations in right renal artery | Number of treated locations in right renal artery | Number of excitations in left renal artery | Number of treated locations in left renal artery | Duration of treatment (seconds) |
|---|---|---|---|---|---|
| 7917 | 6 | 2 | 4 | 1 | 30 |
| 7918 | 7 | 2 | 6 | 2 | 30 |
| 7920 | 6 | 2 | 4 | 1 | 10 |
| 7921 | 7 | 2 | 4 | 1 | 10 |

Results

Norepinephrine (NE): Renal tissue NE content was used as a chemical marker of the sympathetic nervous system activity. Denervation of the sympathetic nervous system potentially causes a reduction in NE release from the sympathetic nerves terminals, indicating reduced sympathetic activity.

The mean reduction in NE concentration (normalized and averaged over different parts of the kidney) in renal tissue in the treated animals in comparison to the control group was, on the average, greater than 50% after 30 days. Longer treatment durations generally caused a greater reduction.

Angiography: Neither perfusion defects nor artery constriction were depicted in the treatment group of animals, neither at the treatment time point, nor at the 30 day follow up. Mild spasm had occurred coincidentally during the treatment, with no sign of permanent spasm or abnormalities remaining or forming de-novo in the 30 days following treatment.

Histopathology: There was no stenosis in any of the renal artery vessels in all levels. All vessels were potent in all levels.

Conclusion

As illustrated by the decrease in NE levels, all 10 pigs were successfully treated by renal denervation using ultrasound energy, in accordance with some embodiments of the invention. A relatively longer treatment (e.g., 30 seconds vs. 10 seconds) resulted in a relatively larger decrease of NE levels, suggesting that longer treatment times disrupt a larger number of nerves and/or nerves to a greater degree. Furthermore, some embodiments as described herein have been shown to be safe, as no abnormalities occurred to the renal arties during and immediately post treatment, as well as at 30 days.

Renal Denervation Study #2

A second renal denervation study was performed. The study goals, study end points, experimental materials, experimental protocols and experimental procedures were substantially the same.

The main difference between the two sets of experiments was the use of the distancing device in the first set of experiments and lack of use of the distancing device in the second set of experiments. In the second set, a steerable catheter was used. To maintain the ultrasonic emission element away from the arterial wall, the side of the catheter substantially opposite the ultrasonic emission element was forced against the arterial wall.

Results: FIG. 23 is a graph comparing reductions in NE levels between the two. For the convenience of the reader, the average relative NE levels and standard deviations are reproduced in table format below.

| | | 0 days | 30 days |
|---|---|---|---|
| Average relative NE levels | | | |
| Reference (N = 6) | | 100.0% | |
| with distancing device | 10 sec (N = 4) | | 30.6% |
| | 30 sec (N = 2) | | 6.8% |
| no distancing device | 10 sec (N = 6) | | 65.7% |
| | 30 sec (N = 6) | | 59.1% |
| Stdev | | | |
| Reference | | 24.7% | |
| with distancing device | 10 sec | | 13.9% |
| | 30 sec | | 6.4% |
| no distancing device | 10 sec | | 20.4% |
| | 30 sec | | 18.7% |

On histological examination using H&E staining, the areas of thermal damage in the experiment with the distancing device and without the distancing device did not appear to be substantially different. Furthermore, even without the distancing device, the areas of thermal damage between 10 seconds and 30 seconds were not substantially different. It is hypothesized that the similar size in thermal damage areas and the relatively higher reductions in NE levels in the animals treated using the distancing device versus those treated without the distancing device are due to differences in tissue cooling due to blood flow controlled by the distancing device. It is hypothesized that increased time did not result in more visible damage in animals treated with the distancing device due to the decrease in blood cooling caused by the device. Nerves outside of the areas of the thermal damage region were not visibly damaged using H&E staining. For example, reduction of NE levels to 6.8% suggests that 93% of nerves were destroyed, a level much higher than can be explained by the visible damage.

The results show that without the distancing device, the reduction in NE results were not statistically different between the 10 second and 30 second treatment (65.7% vs 59.1%).

Furthermore, the results show that use of the distancing device resulted in relatively lower NE levels than without the distancing device. For 10 seconds 30.6% vs 65.7%, for 30 seconds 6.8% vs 59.1%.

Conclusion

The results provide support that thermal regions can be formed and/or NE levels can be reduced in a time insensitive manner, for example, by controlling blood flow along the arterial wall. Without being bound to theory, inventors believe that the reduction in NE was time insensitive due to the relative increase in blood flow next to the arterial wall without the distancing device, as compared to the reduced blood flow next to the arterial wall with the distancing device. The increased cooling of the arterial wall by the blood is believed to have prevented additional US energy from causing additional damage to renal nerves past a threshold.

Furthermore, the results provide support that nerves can be selectively damaged outside the thermal damage region (resulting in lower NE levels) without being visibly detectable (e.g., using H&E staining). Without being bound to theory, inventors believe that the non-visible damage to nerves was caused by a temperature high enough to cause nerve damage, but not visible enough to cause collagen denaturation (which is visible on H&E staining).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

GENERAL

It is expected that during the life of a patent maturing from this application many relevant ultrasound transducers will be developed and the scope of the term transducer is intended to include all such new technologies a priori.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Reference is now made to the following examples, which together with the above descriptions illustrate some embodiments of the invention in a non limiting fashion.

What is claimed is:

1. A method of treating a subject suffering from a nerve related disorder, said method comprising:
   selecting a thermal effect on nerve tissue within a damage region, said region comprising one or both of a lumen wall or nearby surrounding tissues; selecting parameters of unfocused ultrasound to be irradiated to achieve said thermal effect, said parameters comprising an intensity between 10 Watt/cm$^2$ and 35 Watt/cm$^2$, a frequency between 10 Mhz and 20 Mhz, and a treatment duration between 10 and 30 seconds;
   selecting a size of an acoustic element configured to emit said unfocused ultrasound, said acoustic element having a width between 0.2 mm and 2 mm and a length between 1 mm and 10 mm;
   irradiating, from within said lumen, said region with unfocused ultrasound, said irradiating performed at a distance of at least 1 mm from said inner wall so that blood flow cools said wall enough to allow said damage region to be located no closer than 0.2 mm from said inner wall, and to prevent damage to said inner wall; said damage region encompassing a volume having dimensions ranging between 0.2-6.8 mm in a radial direction, between 0.2-5.75 mm in a direction tangential to said lumen, between 0.1 mm and 10 mm in an axial direction, said region being located between 0.2 mm and 10 mm from an inner wall of said lumen, wherein said lumen is a lumen of a blood vessel with blood flowing therein.

2. The method of claim 1, wherein said nerve related disorder comprises hypertension.

3. The method of claim 1, wherein said lumen is selected from the group consisting of: renal artery, aorta, renal artery ostium.

4. The method according to claim 1, wherein said selecting parameters comprises selecting parameters in accordance with that said region comprises at least one nerve and wherein said causing damage comprises causing damage to said at least one nerve.

5. The method according to claim 1, wherein said selecting parameters comprises selecting parameters in accordance with that said region does not include an intima of said lumen.

6. The method according to claim 1, wherein said selecting parameters comprises selecting parameters suitable to cause damage from within said lumen.

7. The method of claim 1, further comprising repeating said causing damage to one or more additional damage regions, said regions being spaced apart.

8. The method of claim 7, wherein said spaced apart regions are distributed around a circumference of said lumen.

9. The method of claim 7, wherein said spaced apart regions are distributed longitudinally along said lumen.

10. The method of claim 7, wherein said spaced apart regions comprise 2-8 locations.

11. The method according to claim 1, wherein said selecting parameters comprises selecting parameters suitable to cause damage without causing stenosis as an aftermath of said treatment.

12. The method according to claim 1, wherein said selecting parameters comprises selecting parameters suitable to cause damage comprises causing damage without causing damage to an intima.

13. The method according to claim 1, wherein said selecting parameters comprises selecting parameters suitable to cause damage without causing damage to an intima and a media.

14. The method according to claim 1, wherein said region is confined to one or more tissue layers selected from peri-adventitia, adventitia, media.

15. The method according to claim 1, wherein said selecting parameters comprises selecting parameters suitable to thermally damage said nerve tis sue.

16. The method according to claim 1, wherein said causing a damage comprises heating said region.

17. The method according to claim 1, wherein said irradiating comprises irradiating said region as one unit.

18. The method according to claim 10, wherein said locations comprise at least one of a renal artery location, an ostium location, and an aorta location.

19. The method according to claim 10, wherein a location comprises multiple damage regions.

20. The method according to claim 1, wherein said selecting a size of an acoustic element comprises selecting a size suitable to disrupt a nerve along a length ranging between 0.1 mm to 30 mm by thermally damaging said nerve.

21. The method according to claim 1, wherein a beam of unfocused ultrasound causing said damage has an axial extent at least the same as said length of said acoustic element.

22. The method according to claim 1, wherein a profile of said intensity is a temporal square wave profile.

23. The method according to claim 1, wherein said selecting a size of said acoustic element comprising selecting a length of 6 mm, a width of 1.5 mm, and a thickness of 0.8 mm.

24. A method of treating a subject suffering from a nerve related disorder, said method comprising:
selecting a thermal effect on nerve tissue within a damage region, said region comprising one or both of a lumen wall or nearby surrounding tissues; selecting parameters of unfocused ultrasound to be irradiated to achieve said thermal effect, said parameters comprising an intensity between 10 Watt/cm$^2$ and 35 Watt/cm$^2$, a frequency between 10 Mhz and 20 Mhz, and a treatment duration between 10 and 30 seconds;
selecting a size of an acoustic element configured to emit said unfocused ultrasound, said acoustic element having a width between 0.2 mm and 2 mm and a length between 1 mm and 10 mm;
selecting a desired damage region encompassing a volume having dimensions ranging between 0.2-6.8 mm in a radial direction, between 0.2-5.75 mm in a direction tangential to said lumen, between 0.1 mm and 10 mm in an axial direction, and irradiating, from within said lumen, said region with unfocused ultrasound, said irradiating performed at a distance of at least 1 mm from said inner wall so that blood flow cools said wall enough to allow said damage region to be located no closer than between 0.2 mm and 10 mm from said inner wall, and to prevent damage to said inner wall,
wherein said lumen is a lumen of a blood vessel with blood flowing therein.

* * * * *